United States Patent [19]

Matsumoto et al.

[11] 3,978,229

[45] Aug. 31, 1976

[54] SYNERGISTIC COMPOSITION COMPRISING $PG_2 \alpha$ AND $PGE_2$

[75] Inventors: Kimiichiro Matsumoto; Tsuneo Fujita, both of Takatsuki; Toshitaka Sakai, Hyogo; Takeshi Tsuda, Suita, all of Japan

[73] Assignee: Ono Pharmaceutical Co., Ltd., Osaka, Japan

[22] Filed: Apr. 8, 1975

[21] Appl. No.: 566,146

[30] Foreign Application Priority Data

Apr. 11, 1974 United Kingdom............ 16242/74

[52] U.S. Cl.............................. 424/317; 424/180; 424/275; 424/285; 424/305

[51] Int. Cl.² ............... A61K 31/19; A61K 31/215; A61K 31/715

[58] Field of Search ........... 424/317, 318, 305, 180, 424/275, 285

[56] References Cited

OTHER PUBLICATIONS

Southern – The Prostaglandins – Futura Publishing Co., (1972), pp. 17 & 18.

*Primary Examiner*—Sam Rosen
*Attorney, Agent, or Firm*—Albert H. Graddis; Frank S. Chow

[57] ABSTRACT

A synergistic composition comprising as active ingredients a $PGF_2 \alpha$ compound or its cyclodextrin clathrate thereof and a $PGE_2$ compound or its cyclodextrin clathrate thereof, at a weight ratio of from about 1:0.33 to about 1:1.

9 Claims, No Drawings

SYNERGISTIC COMPOSITION COMPRISING PGF$_{2\alpha}$ AND PGE$_2$

This invention relates to new associations of prostaglandin compounds, to their use in human and veterinary medicine and to pharmaceutical compositions containing them.

Prostaglandins are derivatives of prostanoic acid which has the following formula:

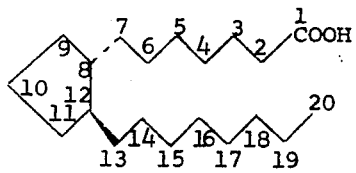

I the dotted line, in accordance with accepted rules of organic nomenclature denoting the α-configuration for the attachment of the group to the cyclopentane ring indicated by the numeral 8, i.e. the group behind the general plane of the ring system, and the solid thickened line denoting the β-configuration where the group lies in front of the plane. Various types of prostaglandins are known, the types depending inter alia on the structure and substituents on the alicyclic ring. For example, the alicyclic rings of prostaglandins F(PGF), E(PGE) and A(PGA) have the structures:

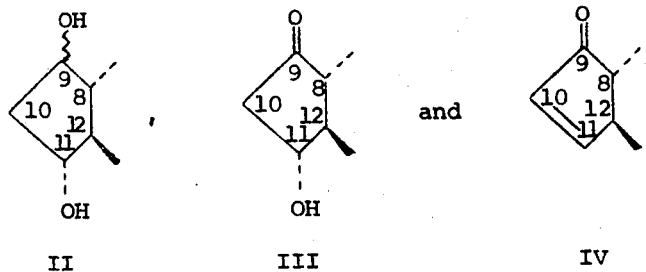

II          III         IV respectively, the wavy line in formula II denoting α- or α-configuration.

Such compounds are sub-classified according to the position of double bond(s) in the side chain(s) attached to the 8- and 12positions of the alicyclic ring. Thus PG$_1$ compounds have a trans-double bond between C$_{13}$–C$_{14}$ (trans-Δ$^{13}$), PG$_2$ compounds have a cis-double bond between C$_5$–C$_6$ and a trans-double bond between C$_{13}$–C$_{14}$ (cis-Δ$^5$, trans-Δ$^{13}$), and PG$_3$ compounds have cis-double bonds between C$_5$–C$_6$ and C$_{17}$–C$_{18}$ and a trans-double bond between C$_{13}$–C$_{14}$ (cis-Δ$^5$, trans-Δ$^{13}$, cis-Δ$^{17}$). For example, prostaglandin F$_{1\alpha}$ (PGF$_{1\alpha}$) and prostaglandin E$_1$ (PGE$_1$) are characterized by the following structures V and VI.

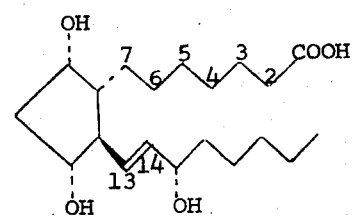

V

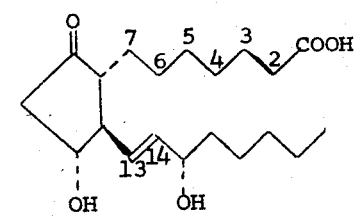

VI respectively. The structures of PGF$_{2\alpha}$ and PGE$_2$, as members of the PG$_2$ group, correspond to those of formulae V and VI respectively with a cis-double bond between the carbon atoms in positions 5 and 6. Compounds in which the double bond between the carbon atoms in positions 13 and 14 of members of the PG$_1$ group is replaced by ethylene are known as dihydro-prostaglandins, e.g. dihydro-prostaglandin-F$_{1\alpha}$ (dihydro-PGF$_{1\alpha}$) and dihydro-prostaglandin-E$_1$ (dihydro-PGE$_1$). When there is a double bond between the carbon atoms in positions 2 and 3 the compounds are known as cis- or trans-Δ$^2$-prostaglandins.

Moreover, when one or more methylene groups are added to, or eliminated from, the aliphatic group attached to the 12-position of the alicyclic ring of the prostaglandins the compounds are known, in accordance with the usual rules of organic nomenclature, as ω-homo-prostaglandins (methylene group added) or ω-nor-prostaglandins (methylene group eliminated) and, when more than one methylene group is added or eliminated, the number is indicated by di-, tri- etc. before the prefix "homo" or "nor."

Prostaglandins are generally known to possess pharmacological properties, for example they stimulate smooth muscle, have hypotensive, diuretic, bronchodilating and antilipolytic activities, and also inhibit blood platelet aggregation and gastric acid secretion, and are, accordingly, useful in the treatment of hypertension, thrombosis, asthma and gastro-intestinal ulcers, in the induction of labour and abortion in pregnant female mammals, in the prevention of arteriosclerosis, and as diuretic agents. They are fat-soluble substances obtainable in very small quantities from various tissues of animals which secrete the prostaglandins in the living body.

For example, PGEs have an inhibitng effect on gastric acid secretion and may, accordingly, be used in the treatment of gastric ulcers. They also inhibit the release of free fatty acid induced by epinephrine and as a result they reduce the concentration of free fatty acid in blood, and are, accordingly, useful in the prevention of arteriosclerosis and hyper-lipemia. $PGE_1$ inhibits blood platelet aggregation and also removes the thrombus and prevents thrombosis. PGEs and PGFs have a stimulating effect on smooth muscle and increase the intestinal peristalsis; these actions indicate therapeutic utility on post-operative ileus and as purgatives. Furthermore, PGE's and PGF's may be used as oxytocics, as abortifacients in the first and second trimesters; in the post-labour expulsion of the placenta, and as oral contraceptive because they regulate the sexual cycle of female mammals. PGEs have vasodilator and diuretic activities. PGEs are useful for improvement in patients suffering from cerebral vascular disease because they increase the cerebral blood flow, and are are useful in the treatment of asthmatic conditions in patients because of their bronchodilating activity.

In particular, $PGF_{2\alpha}$ compounds (i.e. prostaglandin compounds wherein the alicyclic ring has the structure depicted in formula II wherein the 9-position hydroxy group is in $\alpha$-configuration, and there is a cis-double bond between $C_5$–$C_6$ and a trans-double bond between $C_{13}$–$C_{14}$) and $PGE_2$ compounds (i.e. prostaglandin compounds wherein the alicyclic ring has the structure depicted in formula III and there is a cis-double bond between $C_5$–$C_6$ and a trans-double bond between $C_{13}$–$C_{14}$) may be used as oxytocics, as abortifacients in the first and second trimesters, in the post-labour expulsion of the placenta and as oral contraceptives because they regulate the sexual cycle of female mammals; they may also be used to induce menstruation in the treatment of dysmenorrhoea. Undesired side-effects may be encountered both with the PGFs and the PGEs. Similar properties are exhibited by the 13,14-dihydro derivatives of $PGF_{2\alpha}$ - and $PGE_2$-compounds. As a result of research and development, it has now been found that when a $PGE_1$ compound, a dihydro-$PGE_1$ compound, a $PGE_2$ compound or a 13,14-dihydro-$PGE_2$ compound is administered in association with, and preferably simultaneously with, a $PGF_{1\alpha}$ compound, a dihydro-$PGF_{1\alpha}$ compound, a $PGF_{2\alpha}$ compound or a 13,14-dihydro-$PGF_{2\alpha}$ compound, the dose of $PGF_{1\alpha}$ compound, dihydro-$PGF_{1\alpha}$ compound, $PGF_{2\alpha}$ compound or 13,14-dihydro-$PGF_{2\alpha}$ compound required for effectiveness as an oxytocic, abortifacient in the first or second trimester, in the post-labour expulsion of the placenta, as an oral contraceptive and in the induction of menstruation, is substantially reduced, thereby reducing the amount of $PGF_{1\alpha}$ compound, dihydro-$PGF_{1\alpha}$ compound, $PGF_{2\alpha}$ compound or 13,14-dihydro-$PGF_{2\alpha}$ compound which needs to be administered and reducing the incidence and severity of undesired side-effects. The amounts of $PGE_1$ compound, dihydro-$PGE_1$ compound, $PGE_2$ compound or 13,14-dihydro-$PGE_2$ compound required to produce this potentiating effect are substantially smaller than the doses of $PGE_1$ compound, dihydro-$PGE_1$ compound, $PGE_2$ compound or 13,14-dihydro-$PGE_2$ compound which, administered alone, are required to produce the same effects. In addition, as a result of clinical research, it has been found that the sensation of pelvic prostration due to intolerable pain, which is observed when $PGE_2$ alone is administered intravaginally at the dose required for effectiveness as an abortifacient, is not encountered when $PGE_2$ and $PGF_{2\alpha}$ are administered simultaneously. The ratios by weight of $PGF_{1\alpha}$ compound, dihydro-$PGF_{1\alpha}$ compound, $PGF_{2\alpha}$ compound or 13,14-dihydro-$PGF_{2\alpha}$ compound to $PGE_1$ compound, dihydro-$PGE_1$ compound, $PGE_2$ compound or 13,14-dihydro-$PGE_2$ compound required to produce this potentiating effect are from about 1:0.001 to about 1:2000, more particularly from about 1:0.01 to about 1:1000, and preferably from about 1:0.02 to about 1:500, and ratios greater than 1:2000 do not usually exhibit performance greater than those achieved at ratios of about 1:2000. The total amount of $PGE_{1\alpha}$ compound, dihydro-$PGF_{1\alpha}$ compound, $PGF_{2\alpha}$ compound or 13,14-dihydro-$PGF_{2\alpha}$ compound and $PGE_1$ compound, dihydro-$PGE_1$ compound, $PGE_2$ compound or 13,14-dihydro-$PGE_2$ compound administered in association is generally less than one half of the amount of the individual PG compound administered alone which is required to produce the same pharmacodynamic effect. For example, when 16(R)-methyl-$PGF_{2\alpha}$ and 16(R)-methyl-$PGE_2$ are simultaneously administered, the required amount of each prostaglandin is one fifth of the amount of the same prostaglandin compound which, administered alone, is required to produce the same pharmacodynamic effect. The required amount of each $PGF_{1\alpha}$ compound, dihydro-$PGF_{1\alpha}$ compound, $PGF_{2\alpha}$ compound or 13,14-dihydro-$PGF_{2\alpha}$ compound and $PGE_1$ compound, dihydro-$PGE_1$ compound, $PGE_2$ compound or 13,14-dihydro-$PGE_2$ compound is generally 1/3 to 1/25 of the amount of each prostaglandin compound which, administered alone, is required to produce the same pharmacodynamic effect.

In the present specification, it is to be understood that the terms '$PGF_{1\alpha}$ compound, dihydro-$PGF_{1\alpha}$ compound, $PGF_{2\alpha}$ compound or 13,14-dihydro-$PGF_{2\alpha}$ compound' and '$PGE_1$ compound, dihydro-$PGE_1$ compound, $PGE_2$ compound or 13,14-dihydro-$PGE_2$ compound' include not only the prostaglandin compounds having a free carboxylic acid group but also their alkyl esters wherein the alkyl group contains from 1 to 12 carbon atoms and may be straight- or branched-chain, and their non-toxic salts, and alcohol and aldehyde derivatives of the prostaglandin compounds, i.e., compounds in which the carboxy radical is replaced by the hydroxymethylene (i.e. —$CH_2OH$) group or formyl (i.e. —CHO) group, respectively. Furthermore, it is to be understood that the prostaglandin compounds may be in the 'natural' form or its enantiomeric form, or mixtures thereof, more particularly the racemic form consisting of equimolecular mixtures of natural and its enantiomeric form.

According to the present invention, there is provided a method for the production of an oxytocic, abortifacient in the first or second trimester, post-labour placental expulsion, contraceptive, or menstruation-inducing effect in female mammals which comprises the administration of (1) a $PGF_{1\alpha}$ compound, a dihydro-PGE$_{1\alpha}$ compound, a PGF$_{2\alpha}$ compound or a 13,14-dihydro-PGF$_{2\alpha}$ compound characterised by the presence of an alicyclic ring of the formula:

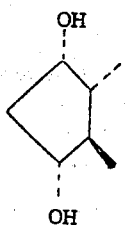

VII and by the reference of (a) a trans-double bond between C$_{13}$–C$_{14}$ and an ethylene group in C$_5$–C$_6$ (i.e. a PGF$_{1\alpha}$ compound), or (b) ethylene groups in C$_5$–C$_6$ and C$_{13}$–C$_{14}$ (i.e. a dihydro-PGF$_{1\alpha}$ compound), or (c) a cis-double bond between C$_5$–C$_6$ and a trans-double bond between C$_{13}$–C$_{14}$ (i.e. a PGF$_{2\alpha}$ compound) or (d) a cis-double bond between C$_5$–C$_6$ and an ethylene group in C$_{13}$–C$_{14}$ (i.e. a 13,14-dihydro-PGF$_{2\alpha}$ compound), in association with, and preferably simultaneously with, (2) a PGE$_1$ compound, a dihydro-PGE$_1$ compound, a PGE$_2$ compound or a 13,14-dihydro-PGE$_2$ compound characterised by the presence of an alicyclic ring of the formula:

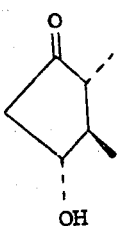

VIII and by the presence of (a), a trans-double bond between C$_{13}$–C$_{14}$ and an ethylene group in C$_5$–C$_6$, (i.e. a PGE$_1$ compound), or (b) ethylene groups in C$_5$–C$_6$ and C$_{13}$–C$_{14}$ (i.e. a dihydro-PGE$_1$ compound), or (c) a cis-double bond between C$_5$–C$_6$ and a trans-double bond between C$_{13}$–C$_{14}$ (i.e. a PGE$_2$-compound), or (d) a cis-double bond between C$_5$–C$_6$ and an ethylene group in C$_{13}$–C$_{14}$ (i.e. a 13,14-dihydro-PGE$_2$ compound), the amounts of each individual prostaglandin compound hereinbefore defined in (1) and (2) being insufficient to produce the hereinbefore defined pharmacodynamic effects when the individual prostaglandin compound is administered alone and the combined amount of the prostaglandin compounds hereinbefore defined in (1) and (2) being sufficient to produce the hereinbefore defined pharmacodynamic effects. More particularly, the present invention provides a method wherein the ratio by weight administered of the prostaglandin compound hereinbefore defined in (1) to the prostaglandin compounds hereinbefore defined in (2) is from about 1:0.001 to about 1:2000, more particularly from about 1:0.01 to about 1:1000, and preferably from about 1:0.02 to about 1:500.

As prostaglandin compounds hereinbefore defined in (1) there may be mentioned: PGF$_{2\alpha}$, ω-hexahomo-PGF$_{2\alpha}$, 15(S)-methyl-PGF$_{2\alpha}$, 16(R)-methyl-PGF$_{2\alpha}$, 17(S)-methyl-PGF$_{2\alpha}$, 17(R)-methyl-PGF$_{2\alpha}$, 18-methyl-PGF$_{2\alpha}$, 19-methyl-PGF$_{2\alpha}$, 15,16-dimethyl-PGF$_{2\alpha}$, 15(S), 16(R)-dimethyl-PGF$_{2\alpha}$, 16,16-dimethyl-PGF$_{2\alpha}$, 17-ethyl-PGF$_{2\alpha}$, 16-cyclohexyl-ω-trinor-PGF$_{2\alpha}$, 13,14-dihydro-PGF$_{2\alpha}$, 15-methyl-13,14-dihydro-PGF$_{2\alpha}$, 16-methylene-PGF$_{2\alpha}$, 16-methylene-PGF$_{2\alpha}$ methyl ester, 16,16-ethano-PGF$_{2\alpha}$, trans-Δ$^{16}$-PGF$_{2\alpha}$ methyl ester, 16,17-methano-PGF$_{2\alpha}$, 16-(3-trifluoromethylphenoxy)-ω-tetranor-PGF$_{2\alpha}$, 16-phenoxy-ω-tetranor-PGF$_{2\alpha}$, 15-methyl-16-phenylthio-ω-tetranor-PGF$_{2\alpha}$, 9α,11α,15α-trihydroxy-16-phenylthio-ω-tetranorprost-cis-5,-trans-13-dienaldehyde, 16-(3-trifluoromethylphenoxy)-9α,11α,15α-trihydroxy-ω-tetranorprosta-cis-5,trans-13-dienaldehyde, 9α,11α,15α-trihydroxy-16-phenoxy-ω-tetranorprosta-cis-5,trans-13-dienaldehyde, 9α,11α,15α-trihydroxy-16-(3-trifluoromethylphenoxy)-ω-tetranorprost-cis-5-enaldehyde, 15-(2-benzo[b]thienyl)-ω-pentanor-PGF$_{2\alpha}$ methyl ester, 15-(2-benzofuranyl)-ω-pentanor-PGF$_{2\alpha}$ methyl ester, 9α,11α,15α-trihydroxy-15-(2-benzo[b]thienyl)-ω-pentanorprosta-cis-5,trans-13-dienaldehyde, 9α,11α,15α-trihydroxy-15-(2-benzofuranyl)-ω-pentanorprosta-cis-5,trans-13-dienaldehyde, 15-(2-benzofuranyl)-ω-pentanor-PGF$_{2\alpha}$ alcohol, 17-phenyl-ω-trinor-16,16,17,17-tetradehydro-PGF$_{2\alpha}$ methyl ester and 16-(cyclohex-1-enylthio)-ω-tetranor-PGF$_{2\alpha}$ methyl ester.

As prostaglandin compounds hereinbefore defined in (2) there may be mentioned: PGE$_2$, ω-hexahomo-PGE$_2$, 16(R)-methyl-PGE$_2$, 17(R)-methyl-PGE$_2$, 18-methyl-PGE$_2$, 3,16(R)-dimethyl-PGE$_2$, 16,16-dimethyl-PGE$_2$, 16-ethyl-PGE$_2$, 17-ethyl-PGE$_2$, 13,14-dihydro-PGE$_2$, 15-methyl-13,14-dihydro-PGE$_2$, 16(R)-methyl-13,14-dihydro-PGE$_2$, 16(R)-methyl-13,14-dihydro-PGE$_2$ methyl ester, 15,16(R)-dimethyl-13,14-dihydro-PGE$_2$, 16-cyclohexyl-ω-trinor-13,14-dihydro-PGE$_2$, 16-methylene-PGE$_2$ methyl ester, trans-Δ$^{16}$-PGE$_2$ methyl ester, 16,16-ethano-PGE$_2$ methyl ester, 16(ε)-methyl-20-hydroxy-PGE$_2$, 16,16-propano-ω-nor-PGE$_2$, 16,16-propano-ω-nor-PGE$_2$ methyl ester and 16,16-propano-ω-dihomo-PGE$_2$.

Preferably the PGF compound administered in the aforesaid method is a PGF$_{2\alpha}$ compound or a 13,14-dihydro-PGF$_{2\alpha}$ compound, and the PGE compound administered therewith is a PGE$_2$ compound or a 13,14-dihydro-PGE$_2$ compound. Advantageously the PGF compound is PGF$_{2\alpha}$, 15(ε)-methyl-13,14-dihydro-PGF$_{2\alpha}$ or 16(R)-methyl-PGF$_{2\alpha}$, and the PGE compound is PGE$_2$ or 16(R)-methyl-PGE$_2$.

Other PGF compounds of importance are 13,14-dihydro-PGF$_{2\alpha}$, 17(S)-methyl-PGF$_{2\alpha}$, 15(S), 16(R)-dimethyl-PGF$_{2\alpha}$, 16-methylene-PGF$_{2\alpha}$ methyl ester, trans-Δ$^{16}$-PGF$_{2\alpha}$ methyl ester, 16-(3-trifluoromethylphenoxy)-ω-tetranor-PGF$_{2\alpha}$, 16-(3-trifluoromethylphenoxy)-9α,11α,15α-trihydroxy-ω-tetranorprost-cis-5,trans-13-dienaldehyde, 9α,11α,15α-trihydroxy-16-phenylthio-ω-tetranorprost-cis-5,-trans-13-dienaldehyde, 16-phenoxy-ω-tetranor-PGF$_{2\alpha}$, 9α,11α,15α-trihydroxy-15-(2-benzofuranyl)-ω-pentanorprost-cis-5,trans-13-dienaldehyde and 9α,11α,15α-trihydroxy-16-phenoxy-ω-tetranorprost-cis-5,trans-13-dienaldehyde, and other PGE compounds of importance are 16,16-dimethyl-PGE$_2$, 16(R)-methyl-13,14-dihydro-PGE$_2$ methyl ester, trans-Δ$^{16}$-PGE$_2$ methyl ester and 16(ε)-methyl-13,14-dihydro-PGE$_2$.

The hereinbefore described potentiating effect has been demonstrated by standard laboratory screening tests, for example in the following tests:-

Test 1.

Anti-nidatory effect in the female rat

Test method: Non-pregnant female Wistar-strain rats, each weighing about 200 g. were mated with male rats of the same strain in the evening. This day was deemed as day 0 of pregnancy if sperm were observed in a vaginal smear test carried out next morning.

The test compounds were injected subcutaneously twice daily during the peri-nidatory period on days 3, 4 and 5 of pregnancy. Where two test compounds were administered to the same animal, the test compounds were injected into different sites.

The animals were sacrificed on day 13 of pregnancy for examination of the uterus and for measurement of the uterine weight. The results obtained are set out in the following Table I. The test compounds identified in Table I were as follows:-

Test Compound

A = $PGF_2\alpha$
B = $PGE_2$
C = 15($\epsilon$)-methyl-13,14-dihydro-$PGF_2\alpha$
D = 16(R)-methyl-$PGE_2$
E = 16(R)-methyl-$PGF_2\alpha$
F = 17(S)-methyl-$PGF_2\alpha$
G = 13,14-dihydro-$PGF_2\alpha$
H = 16($\epsilon$)-methyl-13,14-dihydro-$PGE_2$
I = 15(S),16(R)-dimethyl-$PGF_2\alpha$
J = 16,16-dimethyl-$PGE_2$
K = 16-methylene-$PGF_2\alpha$ methyl ester

TABLE I

| Test Compound | Dose (μg./kg. animal body weight, s.c., b.i.d.) | | Total dose (μg./kg. animal body weight s.c. b.i.d.) | Ratio (Test Compound/Test Compound) | Number of implant sites Mean±S.E. | Number of rats without implant sites/Number of rats treated | Inhibition of nidation (%) | Number of rats with resorbed sites (resorbed/implants) | Total uterine foetal weight (g.) Mean±S.E. |
|---|---|---|---|---|---|---|---|---|---|
| Control | (vehicle) | | — | — | 10.0±0.8 | 0/6 | 0 | 0 | 2.43±0.24 |
| A | 1000 | | 1000 | — | 8.7±1.5 | 2/10 | 20.0 | 1 (1/11) | 1.82±0.29 |
| A | 2000 | | 2000 | — | 1.4±1.4* | 6/7 | 85.7 | 0 | 0.62±0.23* |
| B | 1000 | | 1000 | — | 10.0±0.7 | 0/4 | 0 | 0 | 2.22±0.38 |
| B | 2000 | | 2000 | — | 5.5±1.8 | 5/10 | 50.0 | 0 | 1.28±0.30* |
| A+B | 250(A) | 750(B) | 1000 | 1:3 | 9.0±3.2 | 1/4 | 25.0 | 3 (4/12, 4/15, 9/9) | 2.01±0.58 |
| A+B | 500(A) | 100(B) | 600 | 1:0.2 | 9.8±1.8 | 0/4 | 0 | 0 | 2.27±0.46 |
| A+B | 500(A) | 250(B) | 750 | 1:0.5 | 7.0±2.9 | 2/5 | 40.0 | 2 (4/12, 3/12) | 1.68±0.57 |
| A+B | 500(A) | 500(B) | 1000 | 1:1 | 2.8±2.8* | 3/4 | 75.0 | 1 (4/11) | 0.76±0.46* |
| A+B | 750(A) | 100(B) | 850 | 1:0.13 | 4.8±2.9 | 3/5 | 60.0 | 2 (4/12, 12/12) | 0.94±0.39* |
| A+B | 750(A) | 250(B) | 1000 | 1:0.33 | 0* | 4/4 | 100 | — | 0.38±0.05* |
| A+B | 750(A) | 500(B) | 1250 | 1:0.67 | 0* | 4/4 | 100 | — | 0.35±0.03* |
| A+B | 1000(A) | 1000(B) | 2000 | 1:1 | 0* | 4/4 | 100 | — | 0.34±0.05* |
| C | 250 | | 250 | — | 7.8±2.7 | 1/4 | 25.0 | 2 (1/9, 1/13) | 1.77±0.51 |
| C | 500 | | 500 | — | 2.8±1.8* | 6/8 | 75.0 | 0 | 0.91±0.32* |
| C | 1000 | | 1000 | — | 0* | 4/4 | 100 | — | 0.44±0.05* |
| D | 500 | | 500 | — | 2.8±1.6* | 2/4 | 50.0 | 2 (1/6, 4/5) | 0.72±0.29* |
| D | 1000 | | 1000 | — | 0* | 4/4 | 100 | — | 0.34±0.07* |
| C+D | 100(C) | 33(D) | 133 | 1:0.33 | 6.5±2.5 | 1/4 | 25.0 | 0 | 1.47±0.43 |
| C+D | 100(C) | 66(D) | 166 | 1:0.66 | 4.3±2.5* | 2/4 | 50.0 | 1 (5/10) | 0.82±0.34* |
| C+D | 100(C) | 100(D) | 200 | 1:1 | 6.5±2.8 | 1/4 | 25.0 | 2 (12/12, 1/10) | 1.54±0.50 |
| C+D | 200(C) | 66(D) | 266 | 1:0.33 | 2.3±2.3* | 3/4 | 75.0 | 0 | 0.71±0.04* |
| C+D | 200(C) | 133(D) | 333 | 1:0.67 | 0* | 4/4 | 100 | — | 0.37±0.04* |
| E | 100 | | 100 | — | 6.5±3.8 | 2/4 | 50.0 | 2 (2/14, 4/12) | 1.67±0.79 |
| E | 250 | | 250 | — | 0* | 4/4 | 100 | — | 0.38±0.08* |
| E | 500 | | 500 | — | 0* | 4/4 | 100 | — | 0.28±0.04* |
| E | 1000 | | 1000 | — | 0* | 4/4 | 100 | — | 0.28±0.03* |
| E+D | 60(E) | 20(D) | 80 | 1:0.33 | 7.3±2.4 | 1/4 | 25.0 | 3 (2/10, 10/10, 9/9) | 0.91±0.36* |
| E+D | 60(E) | 40(D) | 100 | 1:0.67 | 2.5±2.5* | 3/4 | 75.0 | 0 | 0.74±0.46* |

*=P <0.05

TABLE Ia

| Test Compound | Dose (μg./kg. animal body weight, s.c., b.i.d.) | | Total dose (μg./kg. animal body weight s.c. b.i.d.) | Ratio (Test Compound)/Test Compound | Number of implant sites Mean±S.E. | Number of rats without implant sites/Number of rats treated | Inhibition of nidation (%) |
|---|---|---|---|---|---|---|---|
| F | 250 | | 250 | — | 9.0±0.9 | 0/4 | 0 |
| F | 500 | | 500 | — | 1.5±1.5* | 3/4 | 75.0 |
| F | 1000 | | 1000 | — | 0* | 4/4 | 100 |
| F+B | 250(F) | 250(B) | 500 | 1:1 | 3.7±3.7 | 2/3 | 66.7 |
| G | 500 | | 500 | — | 9.0±1.5 | 1/7 | 14.3 |
| G | 1000 | | 1000 | — | 2.5±2.5* | 3/4 | 75.0 |
| H | 1000 | | 1000 | — | 9.2±1.2 | 0/5 | 0 |
| H | 2000 | | 2000 | — | 1.3±0.8* | 2/4 | 50.0 |
| G+H | 250(G) | 1000(H) | 1250 | 1:4 | 6.5±2.3 | 1/4 | 25.0 |
| G+H | 500(G) | 1000(H) | 1500 | 1:2 | 0* | 4/4 | 100 |
| I | 500 | | 500 | — | 7.0±2.4 | 1/4 | 25.0 |
| I | 1000 | | 1000 | — | 2.5±2.5* | 3/4 | 75.0 |
| J | 500 | | 500 | — | 8.5±1.8 | 0/4 | 0 |
| J | 1000 | | 1000 | — | 2.3±2.3* | 3/4 | 75.0 |
| I+J | 250(I) | 250(J) | 500 | 1:1 | 0* | 4/4 | 100 |
| K | 500 | | 500 | — | 8.8±3.0 | 1/4 | 25.0 |
| K | 1000 | | 1000 | — | 1.0±1.0* | 3/4 | 75.0 |

TABLE Ia-continued

| Test Compound | Dose (μg./kg. animal body weight, s.c., b.i.d.) | | Total dose (μg./kg. animal body weight s.c. b.i.d.) | Ratio (Test Compound) /Test Compound | Number of implant sites Mean±S.E. | Number of rats without implant sites/Number of rats treated | Inhibition of nidation (%) |
|---|---|---|---|---|---|---|---|
| K+J | 250(K) | 250(J) | 500 | 1:1 | 6.0±1.8 | 1/5 | 20.0 |
| K+J | 500(K) | 250(J) | 750 | 1:0.5 | 0* | 4/4 | 100 |

*=P <0.05

Test 2

Luteolytic effect in female hamster

Test Method:

Non-pregnant female May and Baker strain golden hamsters, each weighing about 100 g., were mated with male hamsters of the same strain in the evening. This day was deemed as Day 0 of pregnancy if sperm were observed in a vaginal smear test carried out next morning.

The test compounds were injected subcutaneously on day 4 of pregnancy. Where two compounds were administered to the same animal, the test compounds were injected into different sites.

The animals were sacrificed on day 7 of pregnancy for examination of the uterus and for measurement of the uterine weight. The results obtained are set out in Table 2.

The test compounds identified in Table 2 are as identified in Test 1.

TABLE 2

| Test Compound | Dose (μg./kg. animal body weight, s.c.) | | Ratio (Test Compound/Test Compound) | Weight of uterus (g.) | Number of animals pregnant/Number of animals treated |
|---|---|---|---|---|---|
| A | 100 | | — | 1.386 | 6/6 |
| B | 500 | | — | 1.078 | 5/6 |
| A+B | 100(A) | 500(B) | 1:5 | 0.398 | 0/6 |
| A+B | 50(A) | 500(B) | 1:10 | 0.435 | 0/6 |

The prostaglandin compounds utilised in the method of the present invention containing a free carboxylic acid may be used in the form of non-toxic salts, i.e. salts the cations of which are relatively innocuous to the animal organism when used in therapeutic doses so that the beneficial properties of the prostaglandin compounds are not vitiated by side effects ascribable to those cations. Preferably the salts are water-soluble. Suitable salts include alkali metal, e.g. sodium or potassium, and ammonium salts and pharmaceutically-acceptable (i.e. non-toxic) amine salts. Amines suitable for forming such salts with carboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 1 to 3 carbon atoms. The salts may be prepared by reacting stoichiometric quantities of the prostaglandin compound and the appropriate base, e.g. an alkali metal hydroxide or carbonate, ammonium hydroxide, ammonia or an amine, in a suitable solvent. The salts may be isolated by concentration of the solution or, if sufficiently insoluble in the reaction medium, by filtration, if necessary after removal of part of the solvent.

The prostaglandin compounds utilised in the method of the present invention which are alkyl esters may be obtained by reacting the corresponding carboxylic acid with (i) diazoalkane compounds, e.g. diazomethane, (ii) alcohols or thiols in the presence of cyclohexylcarbodiimide as condensing agent, or (iii) alcohols following the formation of a mixed acid anhydride by adding a tertiary amine and then a pivaloyl halide or an arylsulphonyl halide (cf. our British Pat. Nos. 1,362,956 and 1,364,125).

The prostaglandin alcohols utilised in the method of the present invention, i.e. compounds in which the carboxy radical of the prostaglandin is replaced by the hydroxymethylene group, may be prepared from the corresponding acids by application of the method described by Pike, Lincoln and Schneider in J. Org. Chem. 34, 3552–3557 (1969), for example by converting the acids into their methyl esters and then the esters into oximes, and reducing the oximes with lithium aluminium hydride to form oxime alcohols, and hydrolyzing them with, for example, acetic acid. PGF alcohols can also be obtained directly by reducing methyl esters of the PGF compounds with lithium aluminium hydride.

The prostaglandin aldehydes utilised in the method of the present invention, i.e. compounds in which the carboxy radical of the prostaglandin is replaced by the formyl group, may be prepared from the 11-(2-tetrahydropyranyl)- or 11,15-bis-(2-tetrahydropyranyl)-derivatives of esters of PGF compounds by (1) reduction by means of diisobutylaluminium hydride, (2) if desired, oxidation of the hydroxy group at the C-9 position to an oxo group, and (3) hydrolysis of the resulting aldehydes under mild acidic conditions.

The prostaglandin compounds utilised in the method of the present invention which are carboxylic acids or alkyl esters or alcohol or aldehyde derivatives may, if desired, be used in the form of cyclodextrin clathrates. The clathrates may be prepared by dissolving the cyclodextrin in water and/or an organic solvent which is miscible with water and adding to the solution the prostaglandin compound in a water-miscible organic solvent. The mixture is then heated and the desired cyclodextrin clathrate product isolated by concentrating the mixture under reduced pressure or by cooling and separating the product by filtration or decanting. The ratio of organic solvent to water may be varied according to the solubilities of the starting materials and products. Preferably the temperature is not allowed to exceed 70°C. during the preparation of the cyclodextrin clathrates. $\alpha$, $\beta$ or $\gamma$-Cyclodextrins or mixtures thereof may be used in the preparation of the cyclodextrin clathrates. Conversion into their cyclodextrin clathrates serves to increase the stability of the prostaglandin compounds. Use in the form of cyclodextrin clathrates is preferable for the $PGE_1$ compounds, dihydro-$PGE_1$ compounds, $PGE_2$ compounds and 13,14-dihydro-$PGE_2$ compounds, e.g. $PGE_2$, because of their instability. The $PGF_{1\alpha}$ compounds, dihydro-$PGE_{1\alpha}$ compounds, $PGF_{2\alpha}$ compounds and 13,14-dihydro-$PGF_{2\alpha}$ compounds, e.g. $PGF_{2\alpha}$, are generally sufficiently stable to render it unnecessary to convert them into cyclodextrin clathrates, but they may also, if desired, be used in the form of cyclodextrin clathrates.

According to a further feature of the present invention, there are provided pharmaceutical compositions which comprise, as active ingredient, at least one $PGF_{1\alpha}$ compound, dihydro-$PGF_{1\alpha}$ compound, $PGF_{2\alpha}$ compound or 13,14-dihydro-$PGF_{2\alpha}$ compound as hereinbefore defined, or cyclodextrin clathrate thereof, and at least one $PGE_1$ compound, dihydro-$PGE_1$ compound, $PGE_2$ compound or 13,14-dihydro-$PGE_2$ compound as hereinbefore defined, or cyclodextrin clathrate thereof, in a ratio by weight of the PG compounds of from about 1:0.001 to about 1:2000, more particularly from about 1:0.01 to about 1:1000, and preferably from about 1:0.02 to about 1:500, together with a pharmaceutical carrier or coating. In clinical practice the prostaglandin compounds will normally be administered orally, rectally, vaginally or parenterally.

Solid compositions for oral administration include compressed tablets, pills, dispensible powders and granules. In such solid compositions, the active ingredients are admixed with at least one inert diluent such as calcium carbonate, potato starch, alginic acid or lactose. The compositions may also comprise, as is normal practice, additional substances other than inert diluents, e.g. lubricating agents, such as magnesium stearate. The two prostaglandin compounds may, if desired, be incorporated in separate layers in tablets, pills and granules. Liquid compositions for oral administration include pharmaceutically-acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing at least one of the PGF and one of the PGE compounds with or without the addition of diluents or excipients.

Solid compositions for vaginal administration include pessaries formulated in manner known per se and containing at least one of the PGF and one of the PGE compounds.

Solid compositions for rectal administration include suppositories formulated in manner known per se and containing at least one of the PGF and one of the PGE compounds.

Solid compositions for vaginal or rectal administration, e.g. pessaries and suppositories, may, if desired, contain the two prostaglandin compounds in separate zones.

Preparations according to the invention for parenteral administration include sterile aqueous or non-aqueous solutions, suspensions, or emulsions. Examples of non-aqueous solvents or suspending media are propylene glycol, polyethylene glycol, vegetable oils such as olive oil and injectable organic esters such as ethyl oleate. These compositions may also include adjuvants such as preserving, wetting, emulsifying and dispersing agents. They may be sterilised, for example by filtration through a bacteria-retaining filter, by incorporation of sterilising agents in the composition or by irradiation. They may also be manufactured in the form of sterile solid compositions, which can be dissolved in sterile water or some other sterile injectable medium immediately before use.

The percentage of the two active ingredients in the compositions of the invention may be varied, it being necessary that it should constitute a proportion such that a suitable dosage for the pharmacodynamic effect desired shall be obtained. Obviously several unit dosage forms may be administered at about the same time. In general, the preparations should normally contain at least 0.0005% by weight of active substances when required for administration by injection; for oral administration the preparations will normally contain at least 0.1% by weight of the active substances. The dose employed depends upon the desired pharmacodynamic effect, the route of administration and the duration of the treatment.

In the adult, the total doses of prostaglandin compound are generally between 5$\mu$g. and 50 mg./kg. body weight by oral, intravaginal or intracervical administration as oxytocics, between 5$\mu$g. and 50 mg./kg. body weight by intravaginal or intracervical administration as abortifacients in the first or second trimester, between 5$\mu$g. and 50 mg./kg. body weight by oral, intravaginal or intracervical administration for post-labour expulsion of the placenta, between 5$\mu$g. and 50 mg./kg. body weight by oral, intravaginal or intracervical administration as contraceptives and between 5$\mu$g. and 50mg./kg. by oral, intravaginal or intracervical administration in the induction of menstruation.

The following Examples illustrate pharmaceutical compositions according to the present invention.

EXAMPLE 1

Witepsol S-58 (a pessary-base supplied by Dynamit Nobel A.G.) (979 mg.) was melted at below 40°C. and there was then added to it the $\beta$-cyclodextrin clathrate of $PGE_2$ (221 mg. containing 17 mg. of $PGE_2$). After mixing to form a suspension, the suspension was poured into a pessary mould. $PGF_{2\alpha}$ (25 mg.) was then dissolved in ethanol (0.2 ml.) and mixed with further Witepsol S-58 (875 mg.) which had been melted at 40° to 50°C. After mixing to form a suspension, the suspension was poured into the pessary mould and cooled until the suspension became solid. There was thus obtained a two-layer pessary suitable for vaginal administration containing, in one layer, the $\beta$-cyclodextrin clathrate of $PGE_2$ (221 mg. containing 17 mg. of $PGE_2$) and, in the other layer, $PGF_{2\alpha}$ (25 mg.).

A pessary prepared as hereinbefore described in the Example was administered intracervically to a 27-year-old woman (gravidity 2, parity 2) at the 20th week of pregnancy followed by 2 hours later by the administration by the same route of a second, similar pessary. The pregnancy was completely terminated in 2 hours following the second administration. No undesirable side-effects were observed.

By proceeding in a similar manner as described in the foregoing Example two-layer pessaries can be obtained suitable for vaginal administration containing i. in one layer 1250 μg. of 15-methyl-13,14-dihydro-PGF$_{2\alpha}$, and in the other layer 25 μg. of 16(R)-methyl-PGE$_2$ in the form of the β-cyclodextrin clathrate;

ii. in one layer 250 μg. of 16(R)-methyl-PGF$_{2\alpha}$, and in the other layer 25 μg. of 16(R)-methyl-PGE$_2$ in the form of the β-cyclodextrin clathrate;

iii. in one layer 50 μg. of 16-(3-trifluoromethylphenoxy)-9α,11α,15α-trihydroxy-ω-tetranorprosta-cis-5,trans-13-dienaldehyde, and in the other layer 25 μg. of 16(R)-methyl-13,14-dihydro-PGE$_2$ methyl ester in the form of the β-cyclodextrin clathrate, and iv. in one layer 1250 μg. of 13,14-dihydro-PGF$_{2\alpha}$, and in the other layer 25 μg. of 16(R)-methyl-PGE$_2$ in the form of the β-cyclodextrin clathrate.

EXAMPLE 2

15-Methyl-13,14-dihydro-PGF$_{2\alpha}$ (2500 μg.) and 16(R)-methyl-PGE$_2$ (50 μg.) were dissolved in ethanol (1 ml.) and the solution obtained was added to an aqueous solution (12 ml.) containing sodium carbonate (50 mg.). Aqueous sodium chloride solution (0.9 w/v, 2 ml.) was then added to give a final volume of 15 ml. The solution was then sterilized by passage through a bacteria-retaining filter and placed in 1.5 ml. portions in 5 ml. ampoules, to give 250 μg. of 15-methyl-13,14-dihydro-PGF$_{2\alpha}$ and 5 μg. of 16(R)-methyl-PGE$_2$ (in the form of their sodium salts) per ampoule. The contents of the ampoules were freeze-dried and the ampoules sealed. The contents of an ampoule in a suitable volume, e.g. 2 ml., of sterile water or physiological saline gave a solution ready for administration by injection.

By proceeding in a similar manner as described in this Example ampoules were obtained containing:

i. 50 μg. of 16(R)-methyl-PGF$_{2\alpha}$ and 5 μg. of 16(R)-methyl-PGE$_2$, ii. 10 μg. of 16-(3-trifluoromethylphenoxy)-9α,1-1α,15α-trihydroxy-ω-tetranorprosta-cis-5,trans-13-dienaldehyde and 5 μg. of 16(R)-methyl-13,14-dihydro-PGE$_2$ methyl ester, and iii. 250 μg. of 13,14-dihydro-PGF$_{2\alpha}$ and 5 μg. of 16(R)-methyl-PGE$_2$, the amounts of PGF and PGE compounds initially dissolved in the ethanol in (i), (ii) and (iii) being 10 times that ultimately present in each sealed ampoule.

EXAMPLE 3

15-Methyl-13,14-dihydro-PGF$_{2\alpha}$ (50000 μg.) and 16(R)-methyl-PGE$_2$ (1000 μg.) were dissolved in ethanol (10 ml.), mixed with mannitol (18.5 g.), sieved through a 30-mesh sieve, dried at 30°C. for 90 minutes and again sieved through a 30-mesh sieve. Aerosil (microfine silica; 200 mg.) was added and the powder obtained was machine-filled into 100 No. 2 hard gelatin capsules to give capsules each containing 500 μg. of 15-methyl-13,14-dihydro-PGF$_{2\alpha}$ and 10 μg. of 16(R)-methyl-PGE$_2$, which after swallowing of the capsule is released into the stomach.

By proceeding in a similar manner as described in this Example capsules were obtained containing:

i. 100 μg. of 16(R)-methyl-PGF$_{2\alpha}$ and 10 μg. of 16(R)-methyl-PGE$_2$, ii. 20 μg. of 16-(3-trifluoromethylphenoxy)-9α,1-1α,15α-trihydroxy-ω-tetranorprosta-cis-5,trans-13-dienaldehyde and 10 μg. of 16(R)-methyl-13,14-dihydro-PGE$_2$ methyl ester, and iii. 500 μg. of 13,14-dihydro-PGF$_{2\alpha}$ and 10 μg. of 16(R)-methyl-PGE$_2$, the amounts of PGF and PGE compounds initially dissolved in the ethanol in (i), (ii) and (iii) being 100 times that ultimately present in each capsule.

The prostaglandin compounds used in the method and pharmaceutical compositions of the present invention may be prepared by known methods. (By the term 'known methods' as used in the present specification is meant methods heretofore used or described in the chemical literature).

Certain of the prostaglandin compounds hereinbefore disclosed are novel compounds whose preparation has not been hitherto published. The novel prostaglandin compounds may be prepared as described in the following Procedures. In these Procedures, 'TLC', 'NMR' and 'IR' represent respectively 'Thin layer chromatography', 'Nuclear magnetic resonance spectrum' and 'Infra-red absorption spectrum'.

PROCEDURE A

Synthesis of 16-methylene-PGF$_2$ (1) Ethyl 2-n-butylacrylate 2-n-Butylacrylic acid (26 g.), ethanol (30 ml.), toluene-p-sulphonic acid (3 g.) and hydroquinone (260 mg.) were dissolved in thiophene-free benzene (350 ml.). The solution was heated under reflux with stirring and the resulting water was removed from the reaction system.

After the reaction was complete, the reaction mixture was diluted with diethyl ether and washed with aqueous sodium bicarbonate solution, water and saturated aqueous sodium chloride solution. The solution was dried over magnesium sulphate and concentrated in vacuo. The residue was distilled under reduced pressure to give pure ethyl 2-n-butylacrylate (24 g; 76%) having the following physical characteristics:

b.p. 77°C./21 mm.Hg; IR (liquid film); ν: 1715, 1630 cm$^{-1}$; NMR (CDCl$_3$ solution); δ: 6.03 (1H, s), 5.42 (1H, s), 4.10 (2H, q), 2.45–1.94 (2H, t).

(2) Dimethyl 2-oxo-3-methylene-n-heptylphosphonate

A 2N solution (400 ml.) of n-butyllithium in diethyl ether was added dropwise to a solution of dimethyl methylphosphonate (110 g.) in pure anhydrous tetrahydrofuran (700 ml.) with stirring under nitrogen, while the reaction temperature was kept within the range of −50° to −60°C. After 10 minutes, a solution of ethyl 2-n-butylacrylate (prepared as described in (1) above; 60 g.) in tetrahydrofuran (150 ml.) was added dropwise to the reaction mixture at −65° to −70°C. and stirred for 4 hours at the same temperature. The reaction mixture was further stirred overnight at 0°C, acidified with acetic acid and concentrated under reduced pressure. Diethyl ether and water were added to the residue in order to remove the water soluble materials. The ethereal solution was dried over magnesium sulphate and concentrated. The residue was distilled under reduced pressure to give pure dimethyl 2-oxo-3-methylene-n-heptylphosphonate (67 g; 69%), having the following physical characteristics:- b.p. 100°–125°C./0.1 mm Hg; IR (liquid film); ν: 1730, 1675, 1630 cm⁻¹; NMR (CDCl₃ solution); δ: 6.18 (1H, s), 4.92 (1H, s), 3.73 (6H, d), 3.90 (2H, d), 2.55–2.04 (2H, t).

(3) 2-Oxa-3-oxo-6-syn-(3-oxo-4-methylene-oct-trans-1enyl)-7-anti-acetoxy-cis-bicyclo[3,3,O]octane A solution of dimethyl 2-oxo-3-methylene-n-heptylphosphonate (prepared as described in (2) above; 12g.) in pure, anhydrous tetrahydrofuran (30 ml.) was added dropwise to a solution of sodium hydride (0.96 g.) in pure anhydrous tetrahydrofuran (300 ml.) with stirring under nitrogen at laboratory room temperature. After the solution became clear, a solution of 2-oxa-3-oxo-6-syn-formyl-7-antiacetoxy-cis-bicyclo[3-,3O]octane (12.7 g.) in pure anhydrous tetrahydrofuran (200 ml.) was added dropwise. The reaction mixture was stirred for 2 hours at 20° to 30°C, acidified with acetic acid and filtered through a pad of silica gel. The filtrate was concentrated under reduced pressure. The residue was subjected to column chromatography on silica gel (1000 g.) using benzene-ethyl acetate (4:1) as eluent to give pure 2-oxa-3-oxo-6-syn-(3-oxo-4-methyleneoct-trans-1-enyl)-7-anti-acetoxy-cis-bicyclo[3,3,O]octane (6.7 g; 52%), having the following physical characteristics:-

IR (liquid film); ν: 2950, 2925, 2860, 1775, 1740, 1665, 1615, 1420, 1370, 1240, 1175, 1110, 1075, 985 cm⁻¹; NMR (CDCl₃ solution); δ: 6.85–6.65 (2H, m), 5.98 (1H, s), 5.81 (1H, s), 5.30–4.85 (2H, m), 2.02 (3H, s), 0.90 (3H, t); TLC (silica gel, developing solvent benzene-ethyl acetate = 4:1); Rf = 0.49.

(4) 2-Oxa-3-oxo-6-syn-(3α-hydroxy-4-methyleneoct-trans-1-enyl)-7-anti-acetoxy-cis-bicyclo[3,3,O]octane Sodium borohydride (2.4 g.) was added dropwise to a solution of 2-oxa-3-oxo-6-syn-(3-oxo-4-methyleneoct-trans-1-enyl)-7-anti-acetoxy-cis-bicyclo[3,3,O]octane (prepared as described in (3) above; 6.7 g.) in methanol (100 ml.) with stirring at −40° to −30°C. After 20 minutes, the reaction mixture was acidified with acetic acid, concentrated and the residue was extracted with ethyl acetate. The extracts were washed with aqueous sodium bicarbonate solution and saturated aqueous sodium chloride solution. The ethyl acetate solution was concentrated under reduced pressure and the residue was subjected to column chromatography on silica gel (350 g.) using diethyl ether-ethyl acetate-n-hexane (200:8:15) as eluent to give pure 2-oxa-3-oxo-6-syn-(3α-hydroxy-4-methyleneoct-trans-1-enyl)-7-anti-acetoxy-cis-bicyclo[3,3,O]octane (1.8 g; 26.8%), having the following physical characteristics:-

IR (liquid film); ν: 3450, 2960, 2930, 2850, 1765, 1735, 1415, 1365, 1240, 1170, 1070-1030, 970, 900 cm⁻¹; NMR (CDCl₃ solution); δ: 5.80-5.55 (2H, m), 5.35–4.75 (2H, m), 5.10 (1H, s), 4.90 (1H, s), 4.70–4.45 (1H, m), 2.03 (3H, s), 0.90 (3H, t); TLC (silica gel, developing solvent dichloromethanemethanol = 19:1); Rf = 0.57.

[1.1 g. of pure 3β-isomer and 1.34 g. of a mixture of the 3α- and 3β-isomers were also obtained].

(5) 2-Oxa-3-hydroxy-6-syn-(3α-hydroxy-4-methyleneoct-trans-1-enyl)-7-anti-hydroxy-cis-bicyclo[3,3,O]octane A solution of diisobutylaluminium hydride (4.3 g.) in toluene (20 ml.) was added dropwise to a solution of 2-oxa-3-oxo-6-syn-(3α-hydroxy-4-methyleneoct-trans-1-enyl)-7-anti-acetoxy-cis-bicyclo[3,3,O]octane (prepared as described in (4) above; 1.7 g.) in toluene (80 ml.) under nitrogen with stirring at −60°C. The reaction mixture was then stirred for 30 minutes and methanol was added. The reaction temperature was elevated to laboratory temperature and water (30 ml.) was added with stirring. The reaction mixture was filtered to remove the resulting crystalline materials and the filtrate was concentrated to give 2-oxa-3-hydroxy-6-syn-(3α-hydroxy-4-methyleneoct-trans-1-enyl)-7-anti-hydroxy-cis-bicyclo[3,3,O]octane (1.28g.; 86%) having the following physical characteristics:-

IR (liquid film); ν: 3350, 2950, 2920, 2860, 1650, 1495, 1450, 1380, 1340, 1290, 1250, 1220, 1105, 1070, 1010, 975, 910 cm⁻¹; NMR (CDCl₃ solution); δ: 5.80-5.35 (2H, m), 5.10 (1H, s), 4.85 (1H, s), 4.75–4.30 (2H, m), 4.30-3.55 (2H, m), 0.90 (3H, t);

TLC (silica gel, developing solvent dichloromethanemethanol = 19:1); Rf = 0.27.

(6) 16-Methylene-PGF$_{2\alpha}$

Sodium hydride (480 mg.) was added to anhydrous dimethyl sulphoxide (10 ml.) and the mixture was stirred with heating at 65° to 70°C, for about 1 hour to obtain sodiomethylsulphinylcarbanide. The product was allowed to cool to room temperature and then added dropwise to a solution of 4-carboxy-n-butyl-triphenylphosphonium bromide (5.1 g.) in pure anhydrous dimethyl sulphoxide (15 ml.) under nitrogen at 15° to 18°C.

The solution became scarlet in the middle of the addition. Then the mixture was stirred vigorously together with a solution of 2-oxa-3-hydroxy-6-syn-(3α-hydroxy-4-methyleneoct-trans-1-enyl)-7-anti-hydroxy-cis-bicyclo[3,3,O]octane (prepared as described in (5) above; 610 mg.) in pure anhydrous dimethyl sulphoxide (15 ml.) at laboratory temperature for two hours. The reaction mixture was poured into ice-water (500 ml.) and the neutral substance was removed by extraction with an ethyl acetate-diethyl ether (1:1) mixture. The aqueous layer was acidified to pH 3.0 with saturated aqueous oxalic acid solution and extracted with ethyl acetate. The extract was washed with water and saturated aqueous sodium chloride solution. The ethyl acetate solution was dried over sodium sulphate and concentrated under reduced pressure. Ethyl acetate was added to the residue and the solution was filtered to remove the resulting crystalline materials. The filtrate was concentrated under reduced pressure. The residue was subjected to column chromatography on silica gel (50 g.) using a chloroform-tetrahydrofuran (5:1) mixture and ethyl acetate as eluents to obtain crude 16-methylene prostaglandin F$_{2\alpha}$ (407 mg.). The crude material was subjected again to column chromatography on silica gel (20 g.) using an ethyl acetate-cyclohexane (5:3) mixture as eluent to obtain pure 16-methylene-PGF$_{2\alpha}$ (252 mg; 31.8%), having the following physical characteristics:-

IR (liquid film); ν: 3450, 3000, 2960, 2930, 2860, 1710, 1450–1400, 1245, 1200, 1120, 1090, 1055, 1030, 975, 910cm⁻¹; NMR (acetone deuteride solution); δ: 5.72-5.50 (2H, m), 5.50–5.25 (2H, m), 5.13 (1H, s), 4.95 (4H, broad s), 4.89 (1H, s), 4.65–4.47 (1H, m), 4.30–4.08 (1H, m), 4.08–3.80 (1H, m), 0.92 (3H, t);

TLC (silica gel, developing solvent chloroform-tetrahydrofuran-acetic acid = 10:2:1); Rf = 0.16; Specific rotation (ethanol solution, C = 1.06); $[\alpha]_D^{23} = -11.3°$.

PROCEDURE B

Synthesis of 16-methylene-$PGF_{2\alpha}$ methyl ester

A solution of 16-methylene-$PGF_{2\alpha}$ (prepared as described in Procedure A; 500 mg.) in diethyl ether (10 ml.) was cooled to 0°C, and maintained at that temperature while an excess of diazomethane in diethyl ether was added until bubbles ceased to envolve. The solution was then kept at 0°C, for 10 minutes, the ether evaporated and the residue subjected to column chromatography on silica gel using an ethyl acetate-cyclohexane (2:3) mixture as eluent to give 16-methylene-$PGF_{2\alpha}$ methyl ester (425 mg; 79.6%) having the following physical characteristic:-

TLC (silica gel, developing solvent chloroform-tetrahydrofuran-acetic acid = (10:2:1); Rf = 0.36.

PROCEDURE C

Synthesis of 16-methylene-$PGE_2$ methyl ester (1) 11,15-Bis-trimethylsilyl 16-methylene prostaglandin $F_{2\alpha}$ methyl ester a. N-Trimethylsilyldiethylamine (1.93 ml; 10 mmole) was added, under an atmosphere of nitrogen, to a solution of 16-methylene-prostaglandin $F_{2\alpha}$ methyl ester (prepared as described in Procedure B; 380 mg; 1 mmole) in dry acetone (20 ml.) and the reaction mixture was stirred for 4 hours at 30°C. The ether was then evaporated and the residue subjected to column chromatography on silica gel using a cyclohexane-ethyl acetate (6:1) mixture as eluent, to give 11,15-bis-trimethylsilyl-16-methylene-prostaglandin $F_{2\alpha}$ methyl ester (390 mg; 74.5%) having the following physical characteristic:-

TLC (silica gel, developing solvent cyclohexane-ethyl acetate = 2:1); Rf =0.74.

b. Bis (trimethylsilyl)acetamide (0.21 ml; 9.2 mmole) was added, under an atmosphere of nitrogen, to a solution of 16-methylene-prostaglandin $F_{2\alpha}$ methyl ester (prepared as described in Procedure B; 35 mg; 0.92 mmole) in dry acetone (2 ml.) and the reaction mixture was stirred for 5 hours at 30°C. The ether was then evaporated and the residue subjected to column chromatography on silica gel using a cyclohexane-ethyl acetate (6:1) mixture as eluent, to give 11,15-bis-trimethylsilyl-16-methylene-$PGF_{2\alpha}$ methyl ester (34.3 mg; 71%), identical to the product of (a) above.

(2) 11,15-Bis-trimethylsilyl-16-methylene-$PGE_2$ methyl ester

Dry pyridine (1.2 ml.) and chromium trioxide (600 mg.) were added to dry methylene chloride (40 ml.) and the mixture was stirred for 20 minutes at laboratory temperature. Celite (3 g.) was then added. The mixture was cooled to 10°C, and maintained at that temperature while a mixture of 11,15-bis-trimethylsilyl-16-methylene-prostaglandin $F_{2\alpha}$ methyl ester (prepared as described in (1) above; 238 mg; 0.455 mmole) and dry methylene chloride (10 ml.) was added. After stirring for 10 minutes, isopropanol (1 ml.) was added and the mixture was stirred for a further 10 minutes. $NaHSO_4 \cdot H_2O$ (3 g.) was then added and stirring continued for a further 10 minutes. The reaction mixture was then filtered through a sintered glass filter covered with magnesium sulphate. The filtrate was concentrated and subjected to column chromatography on silica gel using a cyclohexane-ethyl acetate (6:1) mixture as eluent, to give 11,15-bis-trimethylsilyl-16-methylene-$PGE_2$ methyl ester (153 mg; 65%), having the following physical characteristic:-

TLC (silica gel, developing solvent cyclohexane-ethyl acetate = 5:1); Rf = 0.49.

(3) 16-Methylene-$PGE_2$ methyl ester

Saturated aqueous oxalic acid solution (10 ml.) was added to a solution of 11,15-bis-trimethylsilyl-16-methylene-prostaglandin $E_2$ methyl ester (prepared as described in (2) above; 150 mg; 0.287 mmole) in ethyl acetate (30 ml.). After vigorous stirring for 5 minutes at laboratory temperature, the mixture was transferred to a separating funnel and washed with water followed by saturated aqueous sodium chloride solution. The organic solution was then dried over sodium sulphate, concentrated and subjected to column chromatography on silica gel using a cyclohexane-ethyl acetate (3:2) mixture as eluent to give 16-methylene-$PGE_2$ methyl ester (85.5 mg; 80%) having the following physical characteristic:-

TLC (silica gel, developing solvent chloroform-tetrahydrofuran-acetic acid = 10:2:1); Rf = 0.45.

PROCEDURE D

Synthesis of 16,16-ethano-$PGF_{2\alpha}$ (1) Ethyl, 2,2-ethanohexanoate

Method A.

To a suspension of 55 g. (1.48 mol) of sodium hydride in 1000 ml. of dimethyl sulphoxide (dried and distilled from calcium hydride) was added in small portions solid trimethyloxosulphonium iodide (330 g, 1.48 mol) at 20° to 30°C. An exothermic reaction took place with evolution of hydrogen. The flask was surrounded by a water bath and the mixture was stirred for 45 minutes, by which time the evolution of hydrogen had ceased. 100 g. (0.45 mol) of ethyl 2-bromohexanoate (Beil. 2,325) in 200 ml. of dimethyl sulphoxide was added dropwise to the resulting methylide at 20° to 30°C. Stirring was continued for another 2.5 hours. The mixture was poured into water (5 l.), extracted with diethyl ether, the ethereal extract washed with water, dried ($MgSO_4$) and concentrated to give crude ethyl 2,2-ethanohexanoate (61 g). The product was then distilled under reduced pressure. The fraction boiling at 90° to 94°C./25 mm.Hg. was collected. The yield of ethyl 2,2-ethanohexanoate was 19 g. (25%).

TLC (developing solvent toluene); ethyl 2-bromohexanoate: Rf=0.71; ethyl 2,2-ethanohexanote: Rf = 0.59; NMR($CDCl_3$ solution); δ: 4.02 (2H, q), 1.89–1.23 (2H, m), 1.20–1.05 (2H, dd), 0.95 (3H, t), 0.63–0.55 (2H, dd); IR (neat): ν: 3100, 2950, 2850, 1730, 1470, 1380, 1350, 1220, 1180, 1160, 1100, 1040, 870 $cm^{-1}$.

Method B.

To a suspension of 55 g. (1.48 mol) of sodium hydride in 1000 ml. of dimethylsulphoxide (dried and distilled from calcium hydride) was added in small portions solid trimethyloxosulphonium iodide (330 g, 1.48 mol) at 20°C. to 30°C. An exothermic reaction took place with evolution of hydrogen. The flask was surrounded by a water bath and the mixture was stirred for 45 minutes, by which time the evolution of hydrogen had ceased. 230 g. (1.48 mol) of ethyl 2-methylenehexanoate [J. Org. Chem., 37, 1257 (1972)] in 500 ml. of dimethyl sulphoxide was added dropwise to the resulting methylide at 20° to 30°C. Stirring was continued for another 2.5 hours. The mixture was poured into water (5 liters), extracted with diethyl ether, the ethereal extract washed with water, dried (MgSO$_4$) and concentrated to give crude ethyl 2,2-ethanohexanoate. The crude product was then distilled under reduced pressure to give 70 g. of the pure title compound, b.p. 91° to 94°C./25 mm.Hg;

TLC (developing solvent toluene); Rf = 0.56; NMR (CDCl$_3$ solution); δ: 4.02 (2H, q), 1.89–1.23 (2H, m), 1.20–1.05 (2H, dd), 0.95 (3H, t), 0.63–0.55 (2H, dd); IR (neat); ν: 3100, 2950, 2850, 1730, 1470, 1380, 1350, 1220, 1180, 1160, 1100, 1040, 870 cm$^{-1}$.

(2) Dimethyl 2-oxo-3,3-ethano-n-heptylphosphonate

To 34 g. (0.27 mol) of dimethyl methylphosphonate in 200 ml. of dry tetrahydrofuran, cooled to −60°C, was added dropwise 210 ml. (0.27 mol) of a 1.45M solution of n-butyllithium in diethyl ether. The mixture was stirred at −60°C, for 15 minutes. 20 g. (0.12 mol) of ethyl 2,2-ethanohexanoate (prepared as described in (1) above) in 80 ml. of dry tetrahydrofuran were added at −60°C. and the mixture stirred at −60°C. for 2 hours and then at 0°C. overnight. After warming to room temperature, the mixture was acidified to pH 4 with acetic acid. The formed solid was removed by filtration and the filtrate was evaporated under reduced pressure. The residue was dissolved in 500 ml. of diethyl ether and the insoluble inorganic material was dissolved in 100 ml. of water and separated. The aqueous phase was extracted with diethyl ether and the combined organic phases were washed with saturated aqueous sodium chloride solution, dried (MgSO$_4$) and concentrated. The product was distilled under reduced pressure. The fraction boiling at 100° to 115°C./0.05 mm.Hg was collected. 19 g. of dimethyl 2-oxo-3,3-ethano-n-heptylphosphonate were obtained.

NMR (CDCl$_3$ solution); δ: 3.62 (6H, d), 2.80 (2H, d), 1.70–1.10 (8H, m), 0.95 (3H, t), 0.80–0.70 (2H, dd); IR (neat); ν: 3080, 2950, 2850, 1690, 1460, 1360, 1260, 1040, 880, 810 cm$^{-1}$.

(3) 2-Oxa-3-oxo-6-syn-(3-oxo-4,4-ethanooct-trans-1-enyl)-7-anti-acetoxy-cis-bicyclo[3,3,O]octane 2.5 g. (0.106 mol) of sodium hydride were suspended in 800 ml. of dry tetrahydrofuran and 27 g. (0.109 mol) of dimethyl 2-oxo-3,3-ethano-n-heptylphosphonate (prepared as described in (2) above) in 50 ml. of dry tetrahydrofuran were added dropwise at 30°C. The mixture was stirred at room temperature for 30 minutes, after which time no further hydrogen was evolved. 23 g. (0.109 mol) of 2-oxa-3-oxo-6-syn-formyl-7-anti-acetoxy-cis-bicyclo[3,3,O]octane in 100 ml. of dry tetrahydrofuran were added in one portion, and stirring at room temperature was continued for 1 hour. Glacial acetic acid was then added to neutralise (pH 7) the excess base and the solvent was removed in vacuo. The residue was subjected to column chromatography on 1 kg. of silica gel and the product was eluted with benzene-ethyl acetate (3:1) to give 18.8 g. (51%) of the title compound.

TLC (developing solvent ethyl acetate-benzene=1.4);Rf =0.55; NMR(CDCl$_3$ solution); δ: 6.75–6.45 (1H, dd), 6.40–6.15 (1H, d), 5.06 (2H, m), 3.10–3.06 (complex), 2.03 (3H, s), 2.00–1.03 (complex), 0.95 (3H, t); 0.85–0.65 (2H, m); IR (neat); ν: 3100, 2950, 2850, 1780, 1740, 1680, 1630, 1380, 1250, 1180, 1080, 980 cm$^{-1}$.

(4) 2-Oxa-3-oxo-6-syn-(3-hydroxy-4,4-ethanooct-trans-1-enyl)-7-anti-acetoxy-cis-bicyclo[3,3,O]octane To a solution cooled to −30°C. of 9.0 g. (0.027 mol) of 2-oxa-3-oxo-6-syn-(3-oxo-4,4-ethanooct-trans-1-enyl)-7-anti-acetoxy-cis-bicyclo[3,3,O]octane (prepared as described in (3) above) in methanol (100 ml.) were added in small portions 3.2 g. (0.081 mol) of sodium borohydride. The mixture was stirred at −30°C. for 1.5 hours and then acetic acid was added unitl the pH was 3. The solvent was distilled off in vacuo, and the residue was dissolved in 100 ml. of ethyl acetate. The solution was washed with a saturated sodium bicarbonate aqueous solution, dried (MgSO$_4$) and concentrated in vacuo to give 8.9 g. of the title compound.

TLC (devloping solvent methylene chloride-methanol = 19:1); Rf of bicyclo-octane starting material = 0.84; Rf of bicyclo-octane product = 0.62; NMR(CDCl$_3$ solution); δ: 5.13 (2H, m), 5.05–4.87 (2H, m), 3.75 (1H, m), 2.83–2.16 (complex), 2.03 (3H, s), 1.77 (1H, m), 1.45–1.11 (complex), 0.96 (3H, t), 0.45–0.30 (4H, m); IR (neat); ν: 3450, 3100, 2950, 2850, 1780, 1740, 1380, 1250, 1180, 1030, 980 cm$^{-1}$.

(5) 2-Oxa-3-hydroxy-6-syn-(3-hydroxy-4,4-ethanooct-trans-1-enyl)-7-anti-hydroxy-cis-bicyclo[3,-3,O]octane A solution of 1.69 g. (0.119 mol) of diisobutyl-aluminum hydride in toluene (25 g./100 ml.) was added dropwise to a stirred solution of 8.0 g. (0.024 mol) of 2-oxa-3-oxo-6-syn-(3-hydroxy-4,4-ethanooct-trans-1-enyl)-7-anti-acetoxy-cis-bicyclo[3,3,O]octane (prepared as described in (4) above) in 100 ml. of toluene and 50 ml. of dry tetrahydrofuran cooled to −60°C. The homogeneous solution was stirred for 15 minutes at −60°C., and then 40 ml. of methanol were added. After warming and stirring up to 0°C., 70 ml. of water were added, and the solution was stirred for 1 hour at room temperature. The resulting solid was removed by filtration and the filtrate concentrated in vacuo. The residue was dissolved in 100 ml. of ethyl acetate, washed with saturated brine, dried (MgSO$_4$) and concentrated to give 6.8 g. of the title compound.

TLC (developing solvent ethyl acetate); Rf of bicyclo-octane starting material = 0.82 Rf of bicyclo-octane products = 0.39 and 0.35 (The less polar product on TLC was the C-15 epimer); NMR(CDCl$_3$ solution); δ; 5.75–5.40 (3H, m), 4.75–4.40 (1H, m), 4.10–3.75 (2H, m), 2.95–1.10 (complex), 0.95 (3H, s), 0.35''0.05 (4H, m); IR (neat); ν: 3450, 3100, 2950, 2850, 1450, 980 cm$^{-1}$.

(6) 16,16-Ethano-PGF$_{2\alpha}$

A mixture of 8.3 g. (0.345 mol) of sodium hydride and 150 ml. of dry dimethyl sulphoxide was stirred at 75°C. until gas evolution ceased (ca. 1.5 hours). After cooling to room temperature, the solution of sodiomethylsulphinylcarbanide was ready for use.

76 g. (0.175 mol) of 4-carboxy-n-butyltriphenylphosphonium bromide were dissolved in 150 ml. of dry dimethyl sulphoxide and the solution cooled to 25°C. Then 150 ml. (0.345 mol) of the solution of sodimethylsulphinylcarbanide (prepared as described above) were added with stirring at 20° to 30°C. to give a red solution. 6.8 g. (0.023 mol) of 2-oxa-3-hydroxy-6-syn-(3-hydroxy-4,4-ethanooct-trans-1-enyl)-7-anti-hydroxy-cis-bicyclo[3,3,O]octane (prepared as described in (5) above) in 20 ml. of dimethyl sulphoxide were added in one portion. The mixture was stirred at room temperature for 1 hour and then poured into 1000 ml. of ice-water. The solution was adjusted to pH 9–10 with solid potassium carbonate. Extraction with ethyl acetate-diethyl ether (1:1) removed the neutral components. The aqueous phase was then acidified to pH 3 with solid oxalic acid and extracted with ethyl acetate. The acidic extracts were washed with water and saturated brine, dried (MgSO$_4$) and concentrated. The product was purified by column chromatography on 360 g. of silica gel using ethyl acetate-cyclohexane (3:1) as eluent to give pure 16,16-ethano-PGF$_{2\alpha}$ (350 mg.).

TLC (developing solvent chloroform-tetrahydrofuran-acetic acid = 10:2:1); Rf = 0.18

The Rf value of the C-15 epimer was 0.29; NMR (CDCl$_3$ solution); δ: 5.65–5.20 (4H, m), 5.20–4.80 (4H, m), 4.25–3.75 (3H, m), 2.50–1.06 (complex), 0.95 (3H, t), 0.65–0.15 (4H, m); IR (neat); ν: 3350, 3100, 2950, 2850, –2600, 1710, 1420, 1240, 1220, 1100, 1010, 980, 910 cm$^{-1}$.

PROCEDURE E

Syntheseis of trans-Δ$^{16}$-PGF$_{2\alpha}$ methyl ester (1) Ethyl 2-trans-n-hexenoate A mixture of 176 g. of malonic acid, 176 ml. of pyridine and 108 ml. of butanal was stirred at room temperature for 22 hours, at 40° to 45°C. for 20 hours and at 60° to 65°C. for 3 hours, successively. The reaction mixture was acidified with 250 ml. of 6N sulphuric acid. Diethyl ether was added and the aqueous layer separated. The aqueous layer was extracted with diethyl ether, and the combined organic layers were washed with 6N sulphuric acid, dried over calcium chloride and concentrated under reduced pressure to give 112 g. of 2-trans-n-hexenoic acid having the following physical characteristic:

NMR (CDCl$_3$ solution); δ: 12.4 (1H, s), 7.5–6.9 (1H, m), 6.2–5.7 (1H, d), 2.5–2.0 (2H, q), 1.85–1.2 (2H, m) and 0.95 (3H, t).

2-trans-n-Hexenoic acid (112 g.) was dissolved in a mixture of 400 ml. of benzene and 117 ml. of ethanol, 11.2 g. of p-toluenesulphonic acid were added an the mixture was refluxed overnight. The reaction mixture was diluted with 600 ml. of diethyl ether, washed and saturated aqueous sodium bicarbonate solution, dried over magnesium sulphate and concentrated under reduced pressure. Distillation of the crude product gave 105 g. of ethyl 2-trans-n-hexenoate having the following physical characteristics:

b.p. 71°–72°C./20 mm.Hg; NMR (CDCl$_3$ solution); δ: 7.2–6.65 (1H, m), 6.0–5.5 (1H, d); 4.4–3.9 (2H, q) and 2.4–1.9 (2H, q).

(2) Dimethyl 2-oxo-3-trans-n-heptenylphosphonate 730 ml. of 2N n-butyllithium in diethyl ether were added to a solution of dimethyl methylphosphonate (202 g.) in anhydrous tetrahydrofuran (1.3 litres) with stirring under an atmosphere of nitrogen, while the reaction temperature was kept within the range of –60° to –65°C. After 15 minutes, a solution of 73 g. of ethyl 2-trans-n-hexenoate (prepared as described in (1) above) in 440 ml. of tetrahydrofuran was added dropwise to the reaction mixture at –65° to –70°C. and stirred for 4 hours at the same temperature. The reaction mixture was further stirred overnight at 0°C. acidified with acetic acid to pH 4 and concentrated under reduced pressure. Diethyl ether and water were added to the residue in order to remove the water soluble materials. The ethereal layer was dried over magnesium sulphate and concentrated. The residue was distilled under reduced pressure to give 50 g. of dimethyl 2-oxo-3-trans-n-heptenylphosphonate having the following physical characteristics:- b.p. 116°–125°C./0.3 mm.Hg; NMR (CDCl$_3$ solution); δ: 7.3–6.8 (1H, m), 6.5–6.1 (1H, d), 3.9–3.7 (6H, d), 3.5–3.0 (2H, d) and 2.5–2.0 (2H, q).

(3) 2-Oxa-3-oxo-6-syn-(3-oxo-octa-trans-1,trans-4-dienyl)-7-anti-acetoxy-cis-bicyclo[3,3,0]octane A solution of 25 g. of dimethyl 2-oxo-3-trans-n-heptenylphosphonate (prepared as described in (2) above) in 60 ml. of anhydrous tetrahydrofuran was added dropwise to a solution of 4.9 g. of sodium hydride (content; 65.1%) in 800 ml. of anhydrous tetrahydrofuran with stirring under an atmosphere of nitrogen at ambient temperature. After the solution became clear, a solution of 25 g. of 2-oxa-3-oxo-6-syn-formyl-7-anti-acetoxy-cis-bicyclo[3,3,0]octane (prepared as described by E. J. Corey et al, J. Amer. Chem. Soc., 92, p.397) in 200 ml. of anhydrous methylene chloride was added dropwise. The reaction mixture was stirred for 2 hours at 20° to 30°C., acidified with acetic acid and filtered through a pad of silica gel. The filtrate was concentrated under reduced pressure. The residue was subjected to column chromatography on silica gel using benzene-ethyl acetate (4:1) as eluent to give 16 g. of 2-oxa-3-oxo-6-syn-(3-oxo-octa-trans-1, 1,trans-4-dienyl)-7-anti-acetoxy-cis-bicyclo[3,3,0]octane having the following physical characteristics:-

NMR (CDCl$_3$ solution); δ: 7.2–6.1 (4H, m), 5.3–4.9 (2H, m) and 2.02 (3H, s); TLC (silica gel, developing solvent benzene-diethyl ether-methanol = 5:1:1); Rf = 0.51.

(4) 2-Oxa-3-oxo-6-syn-(3α-hydroxyocta-trans-1,trans-4-dienyl)-7-anti-acetoxy-cis-bicyclo[3,3,0]octane 9.45 g. of sodium borohydride were added dropwise to a solution of 31 g. of 2-oxa-3-oxo-6-syn-(3-oxo-octa-trans-1,trans-4-dienyl)-7-anti-acetoxy-cis-bicyclo[3,3,0]-octane (prepared as described in (3) above) in 300 ml. of methanol with stirring at –40° to –30°C. After 20 minutes, the reaction mixture was acidified with acetic acid, concentrated and the residue was extracted with ethyl acetate. The extracts were washed with aqueous sodium bicarbonate solution and saturated aqueous sodium chloride solution. The ethyl acetate layer was concentrated under reduced pressure and the residue was subjected to column chromatography on silica gel using diethyl ether-ethyl acetate-n-hexane (200:8:12) as eluent to give 8.0 g. of 2-oxa-3-oxo-6-syn-(3α-hydroxyocta-trans-1,trans-4-dienyl)-7-anti-acetoxy-cis-bicyclo[3,3,0]octane and 12.0 g. of 2-oxa-3-oxo-6-syn-(3β-hydroxyocta-trans-1,trans-4-dienyl)-7-anti-acetoxy-cis-bicyclo[3,3,0]octane having the following physical characteristics:-

NMR (CDCl$_3$ solution); δ: 5.8–5.4 (4H, m), 5.3–4.7 (2H, m), 4.7–4.3 (1H, m) and 2.0 (3H, s); IR (liquid film); ν: 3450, 2960, 2930, 1770, 1740, 1240, 1170, 970 cm$^{-1}$. TLC (silica gel, developing solvent diethyl ether × 3); 3α-hydroxy compound: Rf = 0.70; 3β-hydroxy compound: Rf = 0.64.

(5) 2-Oxa-3-hydroxy-6-syn-(3α-hydroxyocta-trans-1,trans-4-dienyl)-7-anti-hydroxy-cis-bicyclo[3,3,0]octane.

90 ml. of a solution of diisobutylaluminium hydride (25% w/v) in toluene were added dropwise to a solution of 6.3 g. of 2-oxa-3-oxo-6-syn-(3α-hdyroxyocta-trans-1,trans-4-dienyl)-7-anti-acetoxy-cis-bicyclo[3,3,-0]octane (prepared as described in (4)above ) in 120 ml. of toluene under an atmosphere of nitrogen with stirring at –60°C. The reaction mixture was then stirred for 30 minutes and methanol was added. The reaction temperature was elevated to ambient temperature and 50 ml. of water were added with stirring. The reaction mixture was filtered to remove the resulting crystalline materials and the filtrate was concentrated. The residue was purified by column chromatography on silica gel to give 4.4 g. of the title compound having the following physical characteristics:-

NMR (CDCl$_3$ solution); δ: 6.05–5.15 (5H, m), 4.8–4.2 (3H, m) and 4.2–3.0 (3H, m); IR (liquid film); ν: 3350, 2940, 2860 cm$^{-1}$; TLC (silica gel, developing solvent methylene chloridemethanol chloride-methanol 9:1); Rf = 0.30.

(6) Trans-$\Delta^{16}$-PGF$_{2\alpha}$ methyl ester 4.9 g. of sodium hydride (content; 65.1%) were added to 30 ml. of anhydrous dimethyl sulphoxide and the mixture was stirred at 65° to 70°C. for about 1 hour to obtain sodiomethylsulphinylcarbanide. The product was allowed to cool to room temperature and was then added dropwise to a solution of 30 g. of 4-carboxy-n-butyltriphenylphosphonium bromide in 46 ml. of anhydrous dimethyl sulphoxide under an atmosphere of nitrogen at 15° to 18°C. The solution became scarlet in the middle of the addition. The mixture was then stirred vigorously with a solution of 3 g. of 2-oxa-3-hydroxy-6-syn-(3α-hydroxyocta-trans-1,trans-4-dienyl)-7-anti-hydroxy-cis-bicyclo[3,3,0]octane (prepared as described in (5) above) in 40 ml. of anhydrous dimethyl sulphoxide at ambient temperature for two hours. The reaction mixture was poured into 1.5 litres of ice-water and the neutral substances were removed by extraction with ethyl acetate-diethyl ether (1:1). The aqueous layer was acidified to pH 5 to 6 with saturated aqueous oxalic acid solution and extracted with ethyl acetate. The organic layer was washed with water and saturated aqueous sodium chloride solution, dried over sodium sulphate and concentrated under reduced pressure at a low temperature, preferably below 15°C, to give crude trans-$\Delta^{16}$-PGF$_{2\alpha}$ having the following physical characteristics:-

TLC (silica gel, developing solvent methylene chloride-methanol = 12:1); Rf = 0.22

The crude trans-$\Delta^{16}$-PGF$_{2\alpha}$ was dissolved in 40 ml. of diethyl ether, cooled to 0°C. and maintained at that temperature while an excess of diazomethane in diethyl ether was added until bubbling ceased. The solution was then kept at 0°C. for 10 minutes, the diethyl ether was evaporated off and the residue was subjected to column chromatography on silica gel using ethyl acetate-cyclo-hexane (1:1) as eluent to give 1.0 g. of trans-$\Delta^{16}$-PGF$_{2\alpha}$ methyl ester having the following physical characteristics:-

NMR (CDCl$_3$ solution); δ: 5.75–5.26 (6H, m), 4.65–4.45 (1H, m), 4.3–4.05 (1H, m), 4.05–3.75 (1H, m), 3.67 (3H, s), 3.3–2.5 (3H, broad s) and 0.9 (3H, t); IR (liquid film); ν: 3350, 3000, 2950, 2930, 2860, 1738, 1720, 1435, 970 cm$^{-1}$; TLC (silica gel, developing solvent methylene chloride-methanol = 12:1); Rf = 0.41.

PROCEDURE F

Synthesis of trans-$\Delta^{16}$-PGE$_2$ methyl ester 1 ml. of N-trimethylsilyldiethylamine was added under an atmosphere of nitrogen to a solution of 100 mg. of trans-$\Delta^{16}$-PGF$_{2\alpha}$ methyl ester (prepared as described in Procedure E) in 5 ml. of dry acetone and the reaction mixture was stirred for 30 minutes at 30°C. The solvent was then evaporated to give the crude 11,15-bis-trimethylsilyl ether of trans-$\Delta^{16}$-PGF$_{2\alpha}$ methyl ester having the following physical characteristic:-

TLC (silica gel), developing solvent cyclohexane-ethyl acetate = 2:1); Rf = 0.66.

1.1 ml. of dry pyridine and 720 mg. of chromium trioxide were added to 20 ml. of dry methylene chloride and the mixture was stirred for 20 minutes at ambient temperature. 3 g. of infusorial earth were then added. The mixture was cooled to 10°C. and maintained at that temperature while a solution of the crude 11,15-bis-trimethylsilyl ether of trans-$\Delta^{16}$-PGF$_{2\alpha}$ methyl ester (prepared as described above) in 10 ml. of dry methylene chloride was added. After stirring for 10 minutes, 2 ml. of allyl alcohol were added and the mixture was stirred for a further 10 minutes. 3 g. of sodium bisulphate monohydrate were then added and stirring continued for a further 10 minutes. The reaction mixture was then filtered through a sintered glass filter covered with magnesium sulphate. The filtrate was concentrated and gave the crude 11,15-bis-trimethylsilyl ether of trans-$\Delta^{16}$-PGE$_2$ methyl ester, having the following physical characteristic:-

TLC (silica gel, developing solvent cyclohexane-ethyl acetate = 2:1); Rf = 0.71.

5 ml. of saturated aqueous oxalic acid solution were added to a solution of the crude 11,15-bis-trimethylsilyl ether of trans-$\Delta^{16}$-PGE$_2$ methyl ester (prepared as described above) in 15 ml. of ethyl acetate. After vigorous stirring for 5 minutes at ambient temperature, the mixture was poured into a separating funnel and washed with water, followed by saturated aqueous sodium chloride solution. The organic solution was then dried over sodium sulphate, concentrated and subjected to column chromatography on silica gel using cyclohexane-ethyl acetate (3:2) as eluent to give 30 mg. of trans-$\Delta^{16}$-PGE$_2$ methyl ester having the following physical characteristics:-

NMR (CDCl$_3$ solution); δ: 5.95–5.5 (4H, m), 5.46–5.24 (2H, m), 4.67–4.44 (1H, m), 4.3–3.8 (2H, m) 3.66 (3H, s), 3.35–2.95 (1H, broad s), and 0.91 (3H, t); IR (liquid film); ν: 3400, 3005, 2950, 2930, 2860, 1740, 970 cm$^{-1}$; TLC (silica gel, developing solvent methylene chloride-methanol = 10:1); Rf = 0.35.

PROCEDURE G

Synthesis of 16,17-methano-PGF$_2$ (1) Ethyl 2,3-methanohexanoate 15.6 g. of sodium hydride (content 65.1%, 0.423 mol) were suspended in 800 ml. of dimethyl sulphoxide, and there were added, with stirring, 154 g. (0.7 mol) of trimethyloxosulphonium iodide in small portions at 20° to 30°C. over a period of 20 minutes. An exothermic reaction took place with the evolution of hydrogen. After stirring for 10 minutes, there was added, dropwise, a solution of 60 g. (0.423 mol) of ethyl hex-trans-2-enoate in 70 ml. of dimethyl sulphoxide at 20° to 30°C. The reaction mixture was stirred at 40°C. for 3 hours and then poured into 2 litres of ice-water and extracted with diethyl ether. The aqueous layer was treated with 60 ml. of concentrated hydrochloric acid and extracted with diethyl ether. The combined ethereal layer was washed with water, dried with magnesium sulphate and concentrated under reduced pressure. Distillation of the crude product gave 23.2 g.

of ethyl 2,3-methanohexanoate having the following physical characteristics:- b.p. 57° to 60°C./6 mm.Hg; NMR (CDCl$_3$ and CCl$_4$ solution); δ: 4.05 (2H, q), 0.95 (3H, t) and 0.70–0.48 (2H, dd); IR (liquid film); ν: 2950, 1720, 1450, 1405, 1370, 1330, 1265, 1200, 1180, 1100, 1040, 860 cm$^{-1}$.

(2) Dimethyl 2-oxo-3,4-methanoheptylphosphonate

70 g. (0.565 mol) of dimethyl methylphosphonate were dissolved in 500 ml. of anhydrous tetrahydrofuran and there were added 280 ml. of a solution of 2N butyl-lithium (0.56 mol) in diethyl ether at −60° to −70°C. After stirring for 15 minutes, there was added a solution of 40 g. (0.256 mol) of ethyl 2,3-methanohexanoate (prepared as described in (1) above) in 100 ml. of tetrahydrofuran. The reaction mixture was stirred for 2 hours at −60° to −70°C. and then at 0°C. overnight. The reaction mixture was then acidified with acetic acid and concentrated under reduced pressure to one-third of its original volume. The crude product was diluted with diethyl ether, washed with water, dried with magnesium sulphate and concentrated under reduced pressure. Distillation of the crude product gave 27.6 g. of the title compound having the following physical characteristics:- b.p. 117 to 125°C./0.28 mm.Hg; NMR (CDCl$_3$ solution); δ: 3.75 (6H, d), 3.15 (2H,d) and 1.05–0.06 (5H, m); IR (liquid film); ν: 3070, 2950, 2850, 1695, 1450, 1400, 1360, 1260, 1195, 1040 cm$^{-1}$.

(3) 2-Oxa-3-oxo-6-syn-(3-oxo-4,5-methanoocta-trans-1-enyl)-7-anti-acetoxy-cis-bicyclo[3,3,0]octane A solution of 27.6 g. (0.99 mol) of dimethyl 2-oxo-3,4-methanoheptylphosphonate (prepared as described in (2) above) in 65 ml. of anhydrous tetrahydrofuran was added dropwise to a suspension of 3.4 g. of sodium hydride (content 65.1%, 0.092 mol) in 1,000 ml. of anhydrous tetrahydrofuran with stirring under an atmosphere of nitrogen at ambient temperature. After the solution became clear, a solution of 32 g. (0.15 mol) of 2-oxa-3-oxo-6-syn-formyl-7-anti-acetoxy-cis-bicyclo[3,3,0]octane (prepared as described by E. J. Corey et al, J. Amer. Chem. Soc., 92, 397 (1970)) in 200 ml. of methylene chloride was added dropwise and stirred for 2 hours at 20° to 30°C. The reaction mixture was acidified with acetic acid and filtered through a pad of silica gel. The filtrate was concentrated under reduced pressure and the residue was subjected to column chromatography on silica gel using methylene chloride as eluent to give 21.3 g. of the title compound having the following physical characteristics:-

NMR (CDCl$_3$ solution); δ: 6.75–6.46 (1H, dd), 6.48–6.10 (1H, d), 5.20–4.80 (2H, m), 2.00 (3H, s) and 1.05–0.55 (5H, m); IR (liquid film); ν: 3080, 2950, 2870, 1780, 1745, 1680, 1660, 1630, 1415, 1250, 1180, 1080, 985 cm$^{-1}$, TLC (developing solvent methylene chloride-methanol = 19.1); Rf = 0.75.

(4) 2-Oxa-3-hydroxy-6-syn-(3-hydroxy-4,5-methanoocta-trans-1-enyl)-7-anti-hydroxy-cis-bicyclo[3,3,0]octane 100 ml. of a solution of diisobutylaluminium hydride (10 w/v %) in toluene was added dropwise to a solution of 3.0 g. (9.37 mol) of 2-oxa-3-oxo-6-syn-(3-oxo-4,5-methanoocta-trans-1-enyl)-7-anti-acetoxy-cis-bicyclo[3,3,0]octane (prepared as described in (3) above) in 200 ml. of toluene under an atmosphere of nitrogen with stirring at −60°C. The reaction mixture was then stirred for 30 minutes at the same temperature and methanol was added. The reaction temperature was elevated to ambient temperature and 50 ml. of water were added with stirring. After filtration in order to remove the resulting crystalline materials, the filtrate was concentrated under reduced pressure to give 2.7 g. of the title compound having the following physical characteristics:-

NMR (CDCl$_3$ solution); δ: 5.80–5.40 (3H, m), 4.73–4.40 (1H, m), 4.10–3.65(2H, m), 0.92 (3H, s) and 0.80–0.14 (4H, m); IR (liquid film); ν: 3400, 3060, 2950, 2860, 1760, 1380, 980 cm$^{-1}$; TLC (developing solvent methylene chloride-methanol = 19:1); Rf = 0.07.

(5) 16,17-Methano-PGF$_{2\alpha}$ 4.9 g. of sodium hydride (content 65.1%, 0.133 mol) were added to 20 ml. of anhydrous dimethyl sulphoxide and the mixture was stirred with heating at 65° to 70°C. for about one hour to obtain sodiomethylsulphinylcarbanide. The product was allowed to cool to room temperature and then added dropwise to a solution of 31.4 g. (0.071 mol) of 4-carboxy-n-butyltriphenylphosphonium bromide in 60 ml. of dimethyl sulphoxide under an atmosphere of nitrogen at 15° to 20°C. The reaction mixture became scarlet in the middle of the addition. Then the reaction mixture was stirred vigorously together with a solution of 2.7 g. (9.6 mol) of 2-oxa-3-hydroxy-6-syn-(3-hydroxy-4,5-methanoocta-trans-1-enyl)-7-anti-hydroxy-cis-bicyclo[3,30]octane (prepared as described in (4) above) in 40 ml. of dimethyl sulphoxide at ambient temperature for 2 hours. The reaction mixture was poured into 1.5 litres of ice-water, treated with a small amount of potassium carbonate and extracted with an ethyl acetate-diethyl ether (1:1) mixture in order to remove neutral substances. The aqueous layer was acidified with saturated aqueous oxalic acid to pH 5 to 6 and extracted with ethyl acetate. The organic layer was washed with water and saturated aqueous chloride soluton, dried over sodium sulphate and concentrated under reduced pressure at a low temperature to obtain crude 16,17-methano-PGF$_{2\alpha}$ having the following physical characteristic:

TLC (developing solvent chloroform-tetrahydrofuran-acetic acid = 10:2:1); Rf = 0.10.

PROCEDURE H

Synthesis of 18-methyl-PGF$_{2\alpha}$ and 18-methyl-PGE$_2$ (1) Dimethyl 5-methyl-2-oxo-heptylphosphonate 123 g. of dimethyl methylphosphonate were dissolved in 700 ml. of tetrahydrofuran and the solution cooled to −78°C. To this solution a solution of n-butyllithium (prepared from 150 g. of n-butyl bromide and 18.5 g. of lithium) in 600 ml. of diethyl ether was added dropwise, keeping the temperature below −50°C., and stirred at the same temperature for 10 minutes.

A solution of 56 g. of ethyl 4-methylhexanoate in 288 ml. of tetrahydrofuran was added dropwise and the mixture stirred at the same temperature for two hours and allowed to warm to 10°C. The reaction mixture was then neutralized with acetic acid, concentrated under reduced pressure, and after the addition of water to the residue, extracted with diethyl ether. After drying the ethereal extract over sodium sulphate, the solvent was distilled off and the residue subjected to distillation under reduced pressure to give 51 g. (yield 67%) of the title compound as a colorless oil having the following physical characteristics:

b.p. 110° to 120°C./0.2 mm.Hg; IR (liquid film); ν: 2950, 2850, 1710, 1460, 1270, 1190, 1040, 820 cm$^{-1}$.

(2) 2-Oxa-3-oxo-6-syn-(3-oxo-6-methyloct-trans-1-enyl)7-anti-acetoxy-cis-bicyclo[3,3,0]octane 8.24 g. of sodium hydride (content 63.8%) were suspended in 1.23 litres of tetrahydrofuran, and a solution of 51 g. of dimethyl 5-methyl-2-oxo-heptylphosphonate [prepared as described in (1) above] in 250 ml. of tetrahydrofuran was added. Hydrogen was vigorously generated and the solution became yellow. Into the solution, a solution of 59 g. of 2-oxa-3-oxo-6-syn-formyl-7-anti-acetoxy-cis-bicyclo[3,3,0]octane [prepared as described in J. Amer. Chem. Soc. 92, 397 (1970)] in 150 ml. of tetrahydrofuran was introduced and the reaction mixture stirred at room temperature for an hour. It was then neutralized with acetic acid (15 ml.) and concentrated under reduced pressure. The residue was purified by column chromatography on silica gel using ethyl acetate-benzene (6:1) as eluent to obtain 35 g. of the title compound (yield 50%) as a pale-yellow oil having the following physical characteristics:

IR (liquid film); $\nu$: 2950, 2850, 1775, 1740, 1690, 1640, 1625, 1460, 1380, 1240, 1170, 1080, 980 cm$^{-1}$; TLC (developing solvent ethyl acetate-benzene = 2:8); Rf = 0.63.

(3) 2-Oxa3-oxo-6-syn-(3$\alpha$-hdyroxy-6-methyloct-trans-1-enyl)-7-anti-acetoxy-cis-bicyclo[3,3,0]octane 35 g. of 2-oxa-3-oxo-6-syn-(3-oxo-6-methyloct-trans-1-enyl)-7-anti-acetoxy-cis-bicyclo[3,3,0]octane (prepared as described in (2) above) were dissolved in 350 ml. of methanol, and 12.4 g. of sodium borohydride were added whilst keeping the internal temperature at −50°C. After 10 minutes, the mixture was concentrated and the resulting residue subjected to column chromatography using diethyl ether:ethyl acetate:n-hexane (2:1:1) as eluent to give 11.5 g. of the title compound (yield 33%) as a light-yellow oil having the following physical characteristics:

IR (liquid film); $\nu$: 3400, 2960, 2850, 1780, 1740, 1460, 1380, 1250, 1180, 1080, 1050, 980 cm$^{-1}$; TLC (developing solvent ethyl acetate-benzene = 2:8); Rf = 0.33.

(4) 2-Oxa-3-oxo-6-syn- (3$\alpha$-hydroxy-6-methyloct-trans-1-enyl)-7-anti-hydroxy-cis-bicyclo[3,3,0]octane 11.5 g. of 2-oxa-3-oxo-6-syn-(3$\alpha$-hydroxy-6-methyloct-trans-1-enyl)-7-anti-acetoxy-cis-bicyclo[3,3,0]octane (prepared as described in (3) above) were hydrolysed with an equimolar amount of potassium carbonate in methanol at 25°C. to give 9.7 g. of the title compound (100% yield) as a light-yellow oil having the following physical characteristics:

IR (liquid film); $\nu$: 3400, 2930, 2850, 1780, 1455, 1410, 1370, 1240, 1170, 1080, 1040, 975 cm$^{-1}$; TLC (developing solvent methylene chloride-methanol = 20:1); Rf = 0.33.

(5) 2-Oxa-3-oxo-6-syn[3$\alpha$-(2-tetrahydropyranyloxy)-6-methyloct-trans-1-enyl]-7-anti-(2-tetrahydropyranyloxy)-cis-bicyclo[3,3,0]octane 9.7 g. of 2-oxa-3-oxo-6-syn-(3$\alpha$-hydroxy-6-methyloct-trans- 1-enyl)-7-anti-hydroxy-cis-bicyclo[3,3,0]octane (prepared as described in (4) above) were dissolved in methylene chloride to which dihydropyran (ten times the molar quantity of the starting compound) and a small amount of p-toluenesulphonic acid as a catalyst had been added, and the reaction mixture was stirred at 25°C. for 15 minutes to give 15.5 g. of the title compound (yield 100%) as a light-yellow oil having the following physical characteristics:

IR (liquid film); $\nu$: 2950, 2860, 1780, 1460, 1440, 1380, 1240, 1180 - 1130, 1080, 1030, 980 cm$^{-1}$; TLC (developing solvent methylene chloride-methanol = 20:1); Rf = 0.83.

(6) 2-Oxa-3-hydroxy-6-syn-[3$\alpha$-(2-tetrahydropyranyloxy)-6-methyloct-trans-1-enyl]-7-anti-(2tetrahydropyranyloxy)-cis-bicyclo[3,3,0]octane 15.5 g. of 2-oxa-3-oxo-6-syn-[3$\alpha$-(2-tetrahydropyranyloxy)-6-methyloct-trans-1-enyl]-7-anti-(2-tetrahydropyranyloxy)-cis-bicyclo[3,3,0]octane (prepared as described in (5) above) were dissolved in toluene and reduced with two equimolar amounts of diisobutylaluminium hydride at −60°C. for 30 minutes to give 14.6 g. of the title compound (yield 94%) as a colourless oil having the following physical characteristics:

IR (liquid film); $\nu$: 3400, 2930, 2860, 1450, 1350, 1200, 1130, 1020, 980 cm$^{-1}$; TLC (developing solvent methylene chloride-methanol = 20:1); Rf = 0.41.

(7) 9$\alpha$-Hydroxy-11$\alpha$,15$\alpha$-bis-(2-tetrahydropyranyloxy)-18-methylprosta-cis-5,trans-13-dienoic acid 5.92 g. of sodium hydride (content 63.8%) were suspended in 65 ml. of dimethyl sulphoxide and the suspension heated to 72° to 75°C. for 45 minutes with stirring to obtain sodiomethylsulphinylcarbanide; the reaction mixture was then cooled to room temperature.

To a solution of 37.0 g. of 4-carboxy-n-butyltriphenylphosphonium bromide in 86 ml. of dimethyl sulphoxide, the sodiomethylsulphinylcarbanide solution obtained above was added dropwise whilst keeping the temperature below 20°C. After stirring for 5 minutes, a solution of 14.6 g. of 2-oxa-3-hydroxy-6-syn-[3$\alpha$-(2-tetrahydropyranyloxy)-6-methyloct-trans-1-enyl]-7-anti-(2-tetrahydropyranyloxy)-cis-bicyclo[3,3,0]octane (prepared as described in (6) above) in 74 ml. of dimethyl sulphoxide was added all at once and the reaction mixture was vigorously stirred for 2 hours.

The reaction mixture was then poured into ice-water (1.3 liters), and extracted with ethyl acetate to remove the neutral substances. The aqueous layer was neutralised with oxalic acid and the acidic layer extracted with a mixture of diethyl ether-n-pentane (1:1). The organic layer, after separation, was washed, dried and the solvent removed. The resulting residue was purified by column chromatography on silica gel using benzene:ethanol (20:1) as eluent to give 11.3 g. of the title compound (55% yield) as a light-yellow oil having the following physical characteristics:

IR (liquid film); $\nu$: 3400, 2930, 2850, -2400, 1705, 1465 - 1440, 1120, 1020, 980, 680 cm$^{-1}$; NMR (CDCl$_3$ solution); $\delta$: 6.35-5.75 (2H, O$\underline{H}$), 5.61-5.13 (4H, =C$\underline{H}$), 4.80-4.58 (2H, O-C$\underline{H}$-O), 4.25-3.36 (7H, O-C$\underline{H}$, O-C$\underline{H}_2$); TLC (developing solvent methylene chloride - methanol = 20:1); Rf =0.26.

(8) 18-Methyl-PGF$_{2\alpha}$ 230 mg. of 9$\alpha$-hydroxy-11$\alpha$,15$\alpha$-bis-(2-tetrahydropyranyloxy)-18-methylprosta-cis-5,trans-13-dienoic acid (prepared as described in (7) above) were dissolved in a mixture of 0.36 ml. of 12N hydrochloric acid, 2.8 ml. of water and 3.2 ml. of tetrahydrofuran, and stirred at room temperature for 1 hour. The reaction mixture was poured into 200 ml. of ice-water and extracted with ethyl acetate. The extracts were washed with water, dried over magnesium sulphate and concentrated under reduced pressure. The residue was purified by column chromatography on 20 g. of silica gel using cyclohexane - ethyl acetate (1:5) as eluent to give 99 mg. of 18-methyl-PGF₂ (yield 63%) as a colourless oil having the following physical characteristics:

IR (liquid film); $\nu$: 3350, 2950, 2850, -2300, 1710, 1460, 1400, 1240, 1020, 980 cm$^{-1}$; NMR (CDCl$_3$ solution); $\delta$: 5.60–5.26 (4H), 5.15–4.72 (4H), 4.18–3.80 (3H), 0.97–0.80 (6H); TLC (developing solvent ethyl acetate - formic acid = 400:5); Rf = 0.25.

(9) 18-Methyl-PGE₂

690 mg. of 9α-hydroxy-11α,15α-bis-(2-tetrahydropyranyloxy)-18-methylprosta-cis-5,trans-13-dienoic acid (prepared as described in (7) above) were dissolved in 45 ml. of diethyl ether and cooled to 0° to 5°C. Then 50 ml. of chromic acid solution (prepared by dissolving 3.2 g. of chromium trioxide, 10.8 g. of manganese sulphate and 3.56 ml. of sulphuric acid in water to make the total volume 80 ml.) were added, and the reaction mixture stirred vigorously for 1.5 hours at the same temperature. The reaction mixture was then added to diethyl ether and the aqueous layer was separated and extracted with diethyl ether. The combined ethereal extracts were well washed with water until the washing was not coloured yellow, and dried.

After concentration under reduced pressure, the residue was dissolved in 40 ml. of a mixture of acetic acid:water:tetrahydrofuran (65:35:10) and stirred at 37°C. for 2 hours. The reaction mixture was poured into 100 ml. of ice-water, extracted with ethyl acetate, washed with water, dried over sodium sulphate and concentrated under reduced pressure. The residue was purified by column chromatography on 20 g. of silica gel using cyclohexane:ethyl acetate (1:2) as eluent to give 225 mg. (yield 48%) of 18-methyl-PGE₂ as a colourless oil having the following physical characteristics:

IR (liquid film); $\nu$: 3350, 2950, -2850, -2350, 1740, 1710, 1400, 1240, 1165, 1080, 1025, 975 cm$^{-1}$; NMR (CDCl$_3$ solutionl); $\delta$: 5.72–5.17 (7H), 4.20–3.88 (2H), 2.74 (1H), 1.02–0.85 (6H); TLC (developing solvent ethyl acetate - formic acid = 400:5); Rf = 0.42.

PROCEDURE I

Synthesis of 19-methyl-PGF₂α

(1) Dimethyl 6-methyl-2-oxoheptylphosphonate 132 g. of dimethyl methylphosphonate were dissolved in 60 ml. of tetrahydrofuran and, to the solution, a solution of n-butyllithium (prepared from 160 g. of n-butyl bromide and 16.3 g. of lithium) in 600 ml. of diethyl ether was added. To the reaction mixture was added a solution of 60 g. of ether 5-methylhexanoate in 310 ml. of tetrahydrofuran. The temperature, the time and the post-treatment were carried out under the same conditions as described in Procedure H (1). 42 g. of the title compound (yield 47%) were obtained as a colourless oil having the following physical characteristics:

b.p. 110° to 122°C./0.15 mm.Hg; IR (liquid film); $\nu$: 2960, 2860, 1715, 1460, 1260, 1190, 1040, 830, 810 cm$^{-1}$.

(2) 2-Oxa-3-oxo-6-syn-(3-oxo-7-methyloct-trans-1-enyl)-7-anti-acetoxy-cis-bicyclo[3,3,0]octane Proceeding as described in Procedure H (2) but using 6.7 g. of sodium hydride, 42 g. of dimethyl 6-methyl-2-oxoheptylphosphonate (prepared as described in (1) above) and 48 g. of 2-oxa-3-oxo-6-syn-formyl-7-anti-acetoxy-cis-bicyclo[3,3,0]octane [prepared as described in J. Amer. Chem. Soc., 92, 397 (1970)], 37 g. of the title compound (yield 63.5%) were obtained as a light-yellow oil having the following physical characteristics:

IR (liquid film); $\nu$: 2950, 2850, 1775, 1740, 1690, 1660, 1635, 1460, 1380, 1240, 1170, 1080, 980 cm$^{-1}$; TLC (developing solvent ethyl acetate - benzene = 2:8); Rf = 0.61.

(3) 2-Oxa-3-oxo-6-syn-(3α-hydroxy-7-methyloct-trans-1-enyl)-7-anti-acetoxy-cis-bicyclo[3,3,0]octane Proceeding as described in Procedure H (3) but using 37 g. of 2-oxa-3-oxo-6-syn-(3-oxo-7-methyloct-trans-1-enyl)-7-anti-acetoxy-cis-bicyclo[3,3,0]octane (prepared as described in (2) above) and 13.7 g. of sodium borohydride, 10.7 g. of the title compound were obtained (yield 29%) as a colourless oil having the following physical characteristics:

IR (liquid film); $\nu$: 3400, 2690, 2860, 1775, 1735, 1460, 1380, 1260, 1180, 1090, 1055, 980 cm$^{-1}$; TLC (developing solvent ethyl acetate - benzene = 2:8; Rf = 0.32.

(4) 2-Oxa-3-oxo-6-syn-(3α-hydroxy-7-methyloct-trans-1-enyl)-7-anti-hydroxy-cis-bicyclo[3,3,0]octane 10.7 g. of 2-oxa-3-oxo-6-syn-(3α-hydroxy-7-methyloct-trans-1-enyl)-7-anti-acetoxy-cis-bicyclo[3,3,0]octane (prepared as described in (3) above) were hydrolysed with an equimolar amount of potassium carbonate in methanol at 25°C. for 15 minutes to give 8.9 g. of the title compound (yield 99%) as a light-yellow oil having the following physical characteristics:

IR (liquid film); $\nu$: 3400, 2950, 2860, 1780, 1460, 1410, 1380, 1175, 1090, 1040, 980 cm$^{-1}$; TLC (developing solvent methylene chloride - methanol = 20:1), Rf = 0.31.

(5) 2-Oxa-3-oxo-6-syn-[3α-(2-tetrahydropyranyloxy)-7-methyloct-trans-1-enyl]-7-anti-(2-tetrahydropyranyloxy)-cis-bicyclo[3,3,0]octane The same procedure as in Procedure H (5) was followed using 8.9 g. of 2-oxa-3oxo-6-syn-(3α-hydroxy-7-methyloct-trans-1-enyl)-7-anti-hydroxy-cis-bicyclo[3,3,0]-octane (prepared as described in (4) above) as starting material. The title compound was obtained in a yield of 14.0 g. (98.5%) as a pale yellow oil having the following physical characteristics:

IR (liquid film); $\nu$: 2960, 2850, 1780, 1460, 1435, 1380, 1250, 1180-1130, 1080, 1030, 970 cm$^{-1}$; TLC (developing solvent methylene chloride - methanol = 20:1); Rf = 0.83.

(6) 2-Oxa-3-hydroxy-6-syn-[3α-(2-tetrahydropyranyloxy)-7-methyloct-trans-1-enyl]-7-anti-(2-tetrahydropyranyloxy)-cis-bicyclo[3,3,0]octane 14.0 g. of 2-oxa-3-oxo-6syn-[3α-(2-tetrahydropyranyloxy)- 7-methyloct-trans-1-enyl]-7-anti-(2-tetrahydropyranyloxy)-cis-bicyclo[3,3,0]octane (prepared as described in (5) above) were dissolved in toluene and reduced with two equimolar amounts of diisobutyl-aluminium hydride at −60°C. for 30 minutes to give 13.6 g. of the title compound (yield 97%) as a colourless oil having the following physical characteristics:

IR (liquid fiml); $\nu$: 3400, 2950, 2860, 1450, 1335, 1200, 1130, 1080, 1020, 980 cm$^{-1}$; TLC (developing solvent methylene chloride - methanol = 20:1); Rf = 0.40.

(7) 9α-Hydroxy-11α,15α-bis-(2-tetrahydropyranyloxy)-19-methylprosta-cis-5,trans-13-dienoic acid Sodiomethylsulphinylcarbanide [prepared from 3.8 g. of sodium hydride (content 63.8%) and 50 ml. of dimethyl sulphoxide] was added to 22.5 g. of 4-carboxy-n-butyltriphenylphosphonium bromide in 60 ml. of dimethyl sulphoxide whilst keeping the temperature at 20° to 30°C. After stirring for 5 minutes, a solution of 9.0 g. of 2-oxa-3-hydroxy-6-syn-[3α-(2-tetrahydropyranyloxy)-7-methyloct-trans-1-enyl]-7-anti-(2-tetrahydropyranyloxy)-cis-bicyclo[3,3,0]octane (prepared as described in (6) above) in 40 ml. of dimethyl sulphoxide was added all at once and the reaction mixture was stirred for 2 hours.

The post-treatment and the purification were carried out under the same conditions as described in Procedure H (7). 6.1g. of the title compound (49% yield) were obtained as a light-yellow oil having the following physical characteristics:

IR (liquid film); $\nu$: 3400, 2930, 2850, −2350, 1705, 1465–1440, 1120, 980, 680 cm$^{-1}$; NMR (CDCl$_3$ solution); δ: 5.73–5.20 (6H, =C$\underline{H}$, O$\underline{H}$), 4.85–4.63 (2H, O-C$\underline{H}$-O), 4.26–3.34 (7H, O-C$\underline{H}$, O-C$\underline{H}_2$), 0.86 (6H, d, C$\underline{H}_3$); TLC (developing solvent methylene chloride - methanol = 20:1); Rf = 0.25.

(8) 19-Methyl-PGF$_{2\alpha}$ 500 mg. of 9α-hydroxy-11α,15α-bis-(2-tetrahydropyranyloxy)-19-methylprosta-cis-5,trans-13-dienoic acid (prepared as described in (7) above) were dissolved in a mixture of 0.36 ml. of 12N hydrochloric acid, 2.8 ml. of water and 3.2 ml. of tetrahydrofuran, and stirred at room temperature for 1 hour. The reaction mixture was then poured into 200 ml. of ice-water and extracted with ethyl acetate. The extracts were washed with water, dried over magnesium sulphate and concentrated under reduced pressure. The residue was purified by column chromatography on 20 g. of silica gel using cyclohexane:ethyl acetate (1:5) as eluent to give 188 mg. of 19-methyl-PGF$_{2\alpha}$ (yield 54%) as a colourless oil having the following physical characteristics:

IR (liquid film); $\nu$: 3330, 2950, 2850, −2300, 1705, 1450, 1400, 1240, 1020, 960 cm$^{-1}$; NMR (CDCl$_3$ solution); δ: 5.62–5.06 (8H, =C$\underline{H}$, O$\underline{H}$), 4.30–3.76 (3H, O-C$\underline{H}$), 0.86 (6H, d, C$\underline{H}_3$); TLC (developing solvent ethyl acetate - formic acid = 400:5); Rf = 0.26.

PROCEDURE J

Synthesis of 16-cyclohexyl-ω-trinor-PGF$_{2\alpha}$ (1) Dimethyl 3-cyclohexyl-2-oxobutylphosphonate 74.5 g. of dimethyl methylphosphonate were dissolved in 514 ml. of tetrahydrofuran and the solution cooled to −60°C. To this solution a solution of n-butyllithium [prepared from 40.5 g. of n-butyl bromide and 9.2 g. of lithium] in 240 ml. of diethyl ether was added dropwise. A solution of 39.5 g. of ethyl 2-cyclohexylpropionate in 130 ml. of tetrahydrofuran was added dropwise and the mixture stirred at the same temperature for 2 hours and afterwards at 0°C. overnight. The reaction mixture was then neutralized to pH 7 with acetic acid, concentrated under reduced pressure and, after the addition of water to the residue, extracted with diethyl ether. After drying the ethereal extract, the solvent was distilled off and the residue subjected to distillation under reduced pressure to obtain 40 g. (yield 30.2%) of the title compound as a colourless oil having the following physical characteristics:

b.p. 140 °C./0.2–0.3 mm.Hg; NMR (CCl$_4$ solution); δ: 3.82 (6H, d), 3.18 (2H, d), 2.80–2.30 (1H, m), 2.1–0.65 (14H, m).

(2) 2-Oxa-3-oxo-6-syn-(3-oxo-4-cyclohexylpent-trans-1-enyl)-7-anti-acetoxy-cis-bicyclo[3,3,0]octane 5.7 g. of sodium hydride (content 63.9%) were suspended in 850 ml. of tetrahydrofuran, and a solution of 40 g. of dimethyl 3-cyclohexyl-2-oxobutylphosphonate (prepared as described in (1) above) in 170 ml. of tetrahydrofuran was added. Hydrogen was vigorously generated and the solution became a clear yellow. Into the solution a solution of 32.4 g. of 2-oxa-3-oxo-6-syn-formyl-7-anti-acetoxy-cis-bicyclo[3,3,0]octane in 80 ml. of tetrahydrofuran was introduced and the reaction mixture stirred at room temperature for an hour. It was then neutralized with acetic acid and the resulting precipitate removed by filtration. The filtrate was concentrated under reduced pressure, and the residue purified by means of silica gel column chromatography using as eluent a mixture of ethyl acetate and benzene (1:6) to obtain the title compound as a pale yellow oil in an amount of 32 g. (yield 48%) having the following physical characteristics:

TLC (developing solvent benzene - ethyl acetate = 4:1); Rf = 0.55; NMR (CDCl$_3$ solution); δ: 6.78 (1H, q), 6.25 (1H, d), 5.54–4.92 (2H, m), 1.99 (3H, s); IR (liquid film); $\gamma$: 2900, 1760, 1735, 1675 cm$^{-1}$.

(3) 2-Oxa-3-oxo-6-syn-(3-hydroxy-4-cyclohexylpent-trans-1-enyl)-7-anti-acetoxy-cis-bicyclo[3,3,-0]octane 32 g. of 2-xoa-3-oxo-6-syn-(3-oxo-4-cyclohexylpent-trans-1-enyl)-7-anti-acetoxy-cis-bicyclo[3,3,0]octane (prepared as described in (2) above) were dissolved in 310 ml. of methanol, and 10.5 g. of sodium borohydride were added whilst keeping the internal temperature at −40°C. After 10 minutes, the mixture was neutralized with acetic acid and then concentrated under reduced pressure. The resulting residue was dissolved in ethyl acetate, and the solution was washed successively with a saturated aqueous solution of sodium bicarbonate and a saturated aqueous solution of sodium chloride, and then dried. The solvent was distilled off and the resulting residue subjected to column chromatography to separate the fraction having an α-hydroxy group in the product from that having a β-hydroxy group. As eluent a mixture of diethyl ether, ethyl acetate and cyclohexane (2:1:1) was used to obtain 9 g. of α-hydroxy compound and 12 g. of β-hydroxy compound, and a mixture of both in the amount of 6 g., having the following physical characteristics:

TLC (developed twice with diethyl ether); α-hydroxy compound: Rf = 0.75; β-hydroxy compound : Rf = 0.67; α-hydroxy compound is a white crystalline substance melting at 128° to 130°C.; NMR (CDCl$_3$ solution); δ: 5.60–5.30 (2H, m), 5.14–4.63 (2H, m), 4.2–3.85 (1H, m), 2.0 (3H, s); Elemental analysis : C$_{20}$H$_{30}$O$_5$ Calculated value : C, 68.54%; H, 8.63% Found : C, 68.48%; H, 8.61%.

(4) 2-Oxa-3-hydroxy-6-syn-[3α-(2-tetrahydropyranyloxy)-4-cyclohexylpent-trans-1-enyl]-7-anti-(2-tetrahydropyranyloxy)-cis-bicyclo[3,3,0]octane 9 g. of 2-oxa-3-oxo-6-syn-(3α-hydroxy-4-cyclohexylpent-trans-1-enyl)-7-anti-acetoxy-cis-bicyclo[3,3,-0]octane (prepared as described in (3) above) were stirred with a solution of 4 g. of potassium carbonate in 95 ml. of methanol at 25°C. for 30 minutes to obtain 2-oxa-8c 3-oxo-6-syn-(3α-hydroxy-4-cyclohexylpenttrans-1-enyl)-7-anti-hydroxy-cis-bicyclo[3,3,0]octane as a white crystalline solid in an amount of 6.5 g. (yield 82.2%). This diol was dissolved in 72 ml. of methylene chloride to which 66 mg. of p-toluenesulphonic acid and 5.6 g. of dihydropyran had been added, and the reaction mixture was stirred at room temperature for 15 minutes to obtain 10.5 g. of the bis-tetrahydropyranyl ether in the form of a yellow oil.

The bis-tetrahydropyranyl ether was dissolved in 100 ml. of toluene and, after cooling the solution to $-60°C$., two equimolar amounts of diisobutylaluminium hydride were added with stirring. After subjecting the said ether to reduction for 30 minutes, the title compound was obtained in a yield of 10 g. and as a pale yellow oil having the following physical characteristics:

TLC (developing solvent methylene chloride-methanol = 20:1); Rf = 0.38; NMR (CDCl$_3$ solution); δ: 5.7–5.32 (3H, m), 4.85–4.30 (3H, m), 4.2–3.2 (7H, m).

(5) 9α-Hydroxy-11α,15α-bis-(2-tetrahydropyranyloxy)-16-cyclohexyl-ω-trinorprosta-cis-5,trans-13-dienoic acid 3.74 g. of sodium hydride (content 63.9%) were suspended in 41.4 ml. of dimethyl sulphoxide and the suspension heated to 72°–75°C., with stirring, to obtain sodiomethylsulphinylcarbanide; the reaction mixture was cooled to room temperature.

To a solution of 24.3 g. of 4-carboxy-n-butyltriphenylphosphonium bromide in 54.6 ml. of dimethyl sulphoxide the obtained sodiomethylsulphinylcarbanide solution was added dropwise whilst keeping the temperature at 20° to 30°C. After stirring for 5 minutes, a solution of 10 g. of 2-oxa-3-hydroxy-6-syn-(3α-(2-tetrahydropyranyloxy)-4-cyclohexylpent-trans-1-enyl]-7-anti-(2-tetrahydropyranyloxy)-cis-bicyclo[3,3,0]octane (prepared as described in (4) above) in 20 ml. of dimethyl sulphoxide was added all at once and the reaction mixture was vigorously stirred for 2 hours.

The reaction mixture was then poured into icewater, and extracted with a mixture of diethyl ether and ethyl acetate (1:1) to remove the neutral substances. The aqueous layer was neutralized with oxalic acid and the acidic layer extracted with a mixture of diethyl ether and pentane (1:1). The organic layer after separation was washed, dried and the solvent removed. The resulting residue was purified by means of silica gel column chromatography using as eluent a benzene-ethanol mixture (100:5). The title compound was obtained as a pale yellow oil in an amount of 5 g. (yield 44.6%) having the following physical characteristics:

TLC (developing solvent methylene chloride - methanol = 20:1); Rf = 0.32; IR (liquid film); ν: 3400, 2950–2860, 2400, 1705, 1440 cm$^{-1}$; NMR (CDCl$_3$ solution); δ: 6.2–5.1 (6H, m), 4.80–4.40 (2H, m), 4.20–3.10 (7H, m).

(6) 16-Cyclohexyl-ω-trinor-PGF$_{2\alpha}$ 250 mg. of 9α-hydroxy-11α,15α-bis-(2-tetrahydropyranyloxy)-16-cyclohexyl-ω-trinorprosta-cis -5,-trans-13-dienoic acid (prepared as described in (5) above) were dissolved in a mixture of 0.23 ml. of 12N hydrochloric acid, 1.7 ml. of water and 1.9 ml. of tetrahydrofuran, and stirred at 25°C. for 3 hours. 156 mg. of sodium bicarbonate and a small amount of water were added. The reaction mixture was then extracted with ethyl acetate. The organic layer was washed with a saturated aqueous sodium chloride solution, dried evaporated to dryness under reduced pressure and the residue purified by silica gel column chromatography. As eluent a mixture of ethyl acetate and cyclohexane (3:2) was used. 62 mg. of the title compound in pure form (a colourless oil) was obtained having the following physical characteristics:

TLC (developing solvent chloroform - tetrahydrofuran -acetic acid = 10:2:1); Rf = 0.20; NMR (CDCl$_3$ solution); δ: 5.65–5.26 (4H, m), 5.05–4.56 (4H, broad s), 4.31–3.80 (3H, m), 1.0–0.7 (3H, m). Elemental analysis: C$_{23}$H$_{38}$O$_5$ Calculated value: C, 70.01%; H, 9.71% Found: C, 69.94%; H, 9.68%

PROCEDURE K

Synthesis of ω-hexahomo-PGF$_2$ and ω-hexahomo-PGE$_2$ (1) Dimethyl 2-oxo-tridecylphosphonate 84 g. of dimethyl methylphosphonate were dissolved in 400 ml. of tetrahydrofuran and cooled to $-60°C$. Under an atmosphere of nitrogen, n-butyllithium (prepared from 14 g. of lithium, 116 g. of n-butyl bromide and 510 ml. of diethyl ether) was added dropwise to the solution while maintaining the temperature below $-50°C$. and then stirred for 30 minutes. To the solution thus obtained, 38 g. of lauric acid ethyl ester in 140 ml. of tetrahydrofuran were added at below $-55°C$. and stirred for 16 hours. The reaction mixture was then neutralized with acetic acid, concentrated, dissolved in a small amount of water and extracted with diethyl ether. The extracts were washed with water, dried, concentrated and distilled to give 50 g. of the title compound having the following physical characteristic: b.p.; 164° to 168°C./ 1mm.Hg.

(2) 2-Oxa-3-oxo-6-syn-(3-oxotetradec-trans-1-enyl)-7-anti-acetoxy-cis-bicyclo[3,3,0]octane Under an atmosphere of nitrogen, 300 g. of pyridine in 3.5 liters of methylene chloride were stirred at 20°C. and 75 g. of chromium trioxide were added. After 10 minutes stirring, 375 g. of infusorial earth were added and the mixture cooled to $-2°C$. A solution of 37.5 g. of 2-oxa-3-oxo-6-syn-hydroxymethyl-7-anti-acetoxy-cis-bicyclo[3,3,0]octane in 200 ml. of methylene chloride was added and stirred at 0° to $-2°C$. for 10 minutes; sodium bisulphate was then added and the mixture stirred for 10 minutes. The reaction mixture was filtered and the filtrate was concentrated at 0°C. under reduced pressure to give 2-oxa-3-oxo-6-syn-formyl-7-anti-acetoxy-cis-bicyclo[3,3,0]octane.

8.3 g. of sodium hydride were suspended in 1.25 liters of tetrahydrofuran, stirred at 20°C., 50 g. of dimethyl 2-oxo-tridecylphosphonate (prepared as described in (1) above) were added and stirred at 30°C. for 30 minutes. To the solution, the aldehyde compound (prepared as described above) was added and stirred at 30°C. for 30 minutes; 13.8 ml. of acetic acid were added and stirring continued at 30°C. for 10 minutes. The reaction mixture was filtered and the filtrate was concentrated under reduced pressure. The residue was purified by column chromatography on silica gel using benzene-ethyl acetate (6:1) as eluent to give 37.5 g. of the title compound having the following physical characteristic:- TLC (developing solvent benzene - ethyl acetate = 5:1); Rf = 0.35.

(3) 2-Oxa-3-oxo-6-syn-(3α-hydroxytetradec-trans-1-enyl)-7-anti-acetoxy-cis-bicyclo[3,3,0]octane 37.5 g. of 2-Oxa-3-oxo-6-syn-(3-oxotetradectrans-1-enyl)-7-anti-acetoxy-cis-bicyclo[3,3,0]octane (prepared as described in (2) above) were dissolved in a mixture of 200 ml. of tetrahydrofuran and 170 ml. of methanol, cooled to $-137 35°$ to $-40°C$., and 13 g. of sodium borohydride were added in portions. After 10 minutes stirring, the reaction mixture was neutralized with acetic acid and concentrated. The residue was mixed with aqueous sodium bicarbonate solution and extracted with ethyl acetate. The extracts were dried, concentrated and separated by column chromatography on silica gel using diethyl ether-n-hexane-ethyl acetate (2:1:1) as eluent to give 12 g. of 2-oxa-3-oxo-6-syn-(3α-hydroxytetradec-trans-1-enyl)-7-anti-acetoxy-cis-bicyclo[3,3,0]octane, 10 g. of 2-oxa-3-oxo-6-syn-(3β-hydroxytetradec-trans-1-enyl)-7-anti-acetoxy-cis-bicyclo[3,3,0]octane and 5 g. of the mixture of both compounds having the following physical characteristics:

NMR (CDCl$_3$ solution); δ: 5.81–5.48 (2H, m), 5.26–4.83 (2H, m), 4.12 (1H, m), 2.01 (3H, s); IR (liquid film); ν: 3500, 2920, 2850, 1780, 1745, 1470, 1390, 1255, 1190, 1090, 985 cm$^{-1}$; TLC (developing solvent methylene chloride - methanol = 20:1); Rf = 0.62 (α-OH compound).

(4) 2-Oxa-3-oxo-6-syn-[3α-(2-tetrahydropyranyloxy)tetradec-trans-1-enyl]-7-anti-(2-tetrahydropyranyloxy)cis-bicyclo[3,3,0]octane 12 g. of 2-oxa-3-oxo-6-syn-(3α-hydroxytetradec-trans-1-enyl)-7-anti-acetoxy-cis-bicyclo[3,3,0]octane (prepared as described in (3) above) were dissolved in 100 ml. of methanol and stirred vigorously with 4.3 g. of potassium carbonate at room temperature for 10 minutes. The reation mixture was adjusted to pH 1 with 2N hydrochloric acid, poured into 500 ml. of water and extracted with ethyl acetate. The extracts were washed with water, dried and concentrated to give 10.7 g. of 2-oxa-3-oxo-6-syn-(3α-hydroxytetradec-trans-1-enyl)-7-anti-hydroxy-cis-bicyclo[3,3,0]octane having the following physical characteristic:

TLC (developing solvent methylene chloride - methanol = 20:1); Rf = 0.3.

The diol compound, thus obtained, was dissolved in 105 ml. of methylene chloride and stirred with 81 mg. of p-toluenesulphonic acid and 36 ml. of 2,3-dihydropyran at room temperature for 10 minutes. The rection mixture was washed with water, dried and concentrated to give 15.9 g. of the title compound having the following physical characteristics:

NMR (CDCl$_3$ solution); δ: 5.7–5.3 (2H,m), 5.1–4.8 (1H, m), 4.8–4.5 (2H, m), 4.1–3.15 (6H, m); IR (liquid film); ν: 3500, 2940, 2850, 1800, 1500, -1460, 1380, 1295, 1230, 1110, 1060, 1005, 900, 850 cm$^{-1}$.

(5) 2-Oxa-3-hydroxy-6-syn-[3α-(2-tetrahydropyranyloxy)tetradec-trans-1-enyl]-7-anti-(2-tetrahydropyranyloxy)cis-bicyclo[3,3,0]octane Under an atmosphere of nitrogen, 15.9 g. of 2-oxa-3-oxo-6-syn-[3α-(2-tetrahydropyranyloxy)-tetradec-trans-1-enyl)-7-anti-(2-tetrahydropyranyloxy)-cis-bicyclo[3,3,0]octane (obtained as described in (4) above) were dissolved in 363 ml. of toluene and cooled to −60°C. Maintaining the temperature at −50°C. to −60°C., 62 ml. of diisobutylaluminium hydride in toluene (25 w/v %) were added dropwise to the solution. Excess reducing agent was decomposed with methanol after the completion of the reaction. The reaction mixture was allowed to warm to −20°C., water added and filtered to remove a precipitate. Toluene was added to the filtrate, washed with water containing sodium chloride, dried and concentrated to give 15.9 g. of the title compound having the following physical characteristics:

NMR (CDCl$_3$ solution); δ: 5.90–5.38 (3H, m), 4.92–4.48 (2H, m), 4.33–3.18 (7H, m); IR (liquid film); ν: 3400, 2935, 2850, 1670, 1470, 1460, 1445, 1360, 1330, 1270, 1210, 1190, 1140, 1080, 1030, 980, 920 cm$^{-1}$; TLC (developing solvent methylene chloride - methanol = 20:1); Rf = 0.45.

(6) 9α-Hydroxy-11α,15α-bis-(2-tetrahydropyranyloxy)-ω-hexahomoprosta-cis-5, trans-13-dienoic acid Under an atmosphere of nitrogen, to the ylide (prepared from 33.6 g. of 4-carboxy-n-butyltriphenyl-phosphonium bromide, 5.5 g. of sodium hydride and 125 ml. of dimethyl sulphoxide) there were added 15.9 g. of 2-oxa-3-hydroxy-6-syn-[3α-(2-tetrahydropyranyloxy)-tetradec-trans-1-enyl]-7-anti-(2tetrahydropyranyloxy)-cis-bicyclo[3,3,0]octane (prepared as described in (5) above) in 100 ml. of dimethyl sulphoxide in one portion. The reaction mixture was stirred at 25° to 30°C. for 2 hours, and then poured into 1.1 litres of ice-water, which was adjusted to pH 10 with potassium carbonate, and extracted with diethyl ether:ethyl acetate (1:1) to remove neutral substances. The aqueous layer was adjusted to pH 3 with oxalic acid and extracted with diethyl ether:n-pentane (1:1). The organic layer was washed with water, dried, concentrated and subjected to column chromatography on silica gel using benzene:ethanol (25:1) as eluent to give 9.4 g. of the title compound having the following physical characteristics:

NMR (CDCl$_3$ solution); δ: 5.98–5.21 (6H, m), 4.82–4.50 (2H, m), 4.22–3.24 (7H, m); IR (liquid film); ν: 3450, 2940, 2850, 1740, 1720, 1480, −1440, 1360, 1270, 1210, 1190, 1140, 1085, 1030, 980, 920 cm$^{-1}$; TLC (developing solvent methylene chloride - methanol = 20:1); Rf = 0.31.

(7) ω-Hexahomo-PGF$_{2α}$ 650 mg. of 9α-hydroxy-11α,15α-bis-(2-tetrahydropyranyloxy)-ω-hexahomoprosta-cis-5, trans-13-dienoic acid (prepared as described in (6) above) were stirred with 12 ml. of a mixture of acetic acid:water:tetrahydrofuran (65:35:10) at 37° to 42°C. for 1 hour. The reaction mixture was then diluted with ethyl acetate, washed with water, dried and concentrated. The residue was treated with toluene to remove acetic acid by azeotropic distillation, and purified by column chromatography on silica gel using ethyl acetate:cyclohexane (2:1) as eluent to give 100 mg. of the title compound having the following physical characteristics:

NMR (CDCl$_3$ solution); δ: 5.65–5.20 (4H, m), 5.05–4.75 (4H, m), 4.25–3.80 (2H, m), 0.88 (3H, t); IR (liquid film); ν: 3350, 2930, 2850, 1720, 1470–1410, 1380, 1250, 1120, 1060, 980, 935 cm$^{-1}$; TLC (developing solvent chloroform-tetrahydrofuran - acetic acid = 10:2:1); Rf = 0.23; Optical Rotation: $[α]_D^{25} = +22.0°$ (c = 1.00, ethanol).

(8) 9-Oxo-11α,15α-bis-(2-tetrahydropyranyloxy)-ω-hexahomoprosta-cis-5,trans-13-dienoic acid 1.6 g. of 9α-hydroxy-11α,15α-bis-(2-tetrahydropyranyloxy)-ω-hexahomoprosta-cis-5,trans-13-dienoic acid (prepared as described in (6) above) were dissolved in 43 ml. of diethyl ether and cooled to 0° to 5°C. To the solution, a chromic acid solution (prepared from 1.7 g. of chromium trioxide, 8.35 g. of manganese sulphate, 1.93 ml. of sulphuric acid and water to make the total volume 43 ml.) was added at 0° to 5°C. and stirred for 2 hours. The reaction mixture was then extracted with diethyl ether, the combined extracts were washed sufficiently with water, dried, concentrated and purified by column chromatography on silica gel using benzene:ethanol (35:1) as eluent to give 1.03 g. of the title compound having the following physical characteristics:

NMR (CDCl$_3$ solution); δ: 5.7–5.0 (4H, m), 4.8–4.55 (2H, m), 4.2–3.3 (6H, m); IR (liquid film); ν: 2930, 2850, 1750, 1720, 1470–1440, 1360, 1330, 1270, 1210, 1140, 1080, 1045, 1030, 980, 920 cm$^{-1}$; TLC (developing solvent methylene chloride - methanol = 20:1); Rf = 0.23.

(9) ω-Hexahomo-PGE$_2$ 1.03 g. of 9-oxo-11α,15α-bis-(2-tetrahydropyranyloxy)-ω-hexahomoprosta-cis-5,trans-13-dienoic acid (prepared as described in (8) above) were dissolved in 24.5 ml. of a mixture of acetic acid:water:tetrahydrofuran (65:35:10) and stirred at 37° to 43°C. for 2 hours. The reaction mixture was then treated with ethyl acetate, washed with water, dried and concentrated. The residue was treated with toluene to remove acetic acid by azeotropic distillation, and purified by column chromatography on silica gel using ethyl acetate-cyclohexane (3:2) as eluent to give 535 mg. of the title compound having the following physical characteristics:

NMR (CDCl$_3$ solution); δ: 5.70–5.50 (2H, m), 5.50–5.30 (2H, m), 5.30–4.90 (3H, m), 4.22–3.80 (2H, m), 2.92–2.55 (1H, dd); IR (liquid film); ν: 3350, 2930, 2850, 1750, 1720, 1475–1410, 1380, 1250, 1160, 1080, 1055, 980 cm$^{-1}$; TLC (developing solvent chloroform - tetrahydrofuran - acetic acid = 10:2:1); Rf = 0.46; Optical Rotation: $[\alpha]_D^{25} = -62.2°$ (c = 1.08, ethanol).

PROCEDURE L

Synthesis of 17-ethyl-PGF$_{2\alpha}$ and 17-ethyl-PGE$_2$ (1) Dimethyl 2-oxo-4-ethylheptylphosphonate 120 g. of dimethyl methylphosphonate were dissolved in 800 ml. of tetrahydrofuran and the solution was cooled to −78°C. To this solution, a solution of n-butyllithium (prepared from 200 g. of n-butyl bromide and 22 g. of lithium) in 800 ml. of diethyl ether was added dropwise keeping the temperature below −45°C. and stirred at the same temperature for 10 minutes.

A solution of 76 g. of sec-butyl 3-ethylhexanoate in 120 ml. of tetrahydrofuran was added dropwise at −60°C. and the mixture was stirred at the same temperature for 2 hours and then at room temperature for 3 hours. The reaction mixture was then neutralized with acetic acid, concentrated under reduced pressure and, after the addition of water to the residue, extracted with diethyl ether. The ethereal extracts were washed with a saturated aqueous sodium chloride solution, dried over magnesium sulphate and concentrated under reduced pressure. Distillation of the residue gave 63.4 g. of the title compound having the following physical characteristics:

b.p. 115°–124.5°C./0.4–0.5 mm.Hg;IR (neat); ν: 2950, 1860, 1715, 1460, 1260, 1190, 1040, 820 cm$^{-1}$.

(2) 2-Oxa-3-oxo-6-syn-(3-oxo-5-ethyloct-trans-1-enyl)-7-anti-acetoxy-cis-bicyclo[3,3,0]octane 3.7 g. of sodium hydride (content 63.9%) were suspended in 700 ml. of tetrahydrofuran, and 25 g. of dimethyl 2-oxo-4-ethylheptylphosphonate (prepared as described in (1) above) were added to the suspension. Hydrogen was vigorously generated and the solution became yellow. To the solution was added a solution of 21 g. of 2-oxa-3-oxo-6-syn-formyl-7-anti-acetoxy-cis-bicyclo[3,3,0]octane [prepared as described in J. Amer. Chem. Soc., 92, 397 (1970)] in 50 ml. of tetrahydrofuran at ambient temperature and the reaction mixture was stirred at ambient temperature for 1 hour, acidified with acetic acid and the precipitate was filtered off. The filtrate was concentrated under reduced pressure and the residue was purified by column chromatography on silica gel using a mixture of ethyl acetate:benzene (1:7) as eluent to give 21.5 g. of the title compound as a pale yellow oil having the following physical characteristics:

TLC (developing solvent benzene - methanol - diethyl ether = 5:1:1); Rf = 0.71; IR (neat); ν: 2950, 2850, 1775, 1740, 1690, 1660, 1625, 1455, 1370, 1240, 1170, 1070, 980 cm$^{-1}$; NMR (CDCl$_3$ solution); δ: 6.78 (1H, q), 6.23 (1H, d), 5.25–4.86 (2H, m), 2.04 (3H, s), 0.9 (9H, t).

(3) 2-Oxa-3-oxo-6-syn-(3-hydroxy-5-ethyloct-trans-1-enyl)-7-anti-acetoxy-cis-bicyclo[3,3,0]octane To a solution of 38.5 g. of 2-oxa-3-oxo-6-syn-(3-oxo-5-ethyloct-trans-1-enyl)-7-anti-acetoxy-cis-bicyclo[3,3,0]octane (prepared as described in (2) above) in 300 ml. of methanol, 13 g. of sodium borohydride were added carefully, whilst keeping the internal temperature at −25°C. After 10 minutes, the mixture was neutralized with acetic acid and concentrated under reduced pressure, and the resulting residue was dissolved in ethyl acetate, washed with a saturated aqueous sodium bicarbonate solution and a saturated aqueous sodium chloride solution, dried over magnesium sulphate and concentrated under reduced pressure to give 38.6 g. of the title compound as a pale yellow oil having the following physical characteristics:

TLC (developing solvent methylene chloride - methanol = 20:1); Rf = 0.39; IR (neat); ν: 3460, 2960 – 2870, 1770, 1740, 1460, 1420, 1375, 1240, 1180, 1075, 1060, 975 cm$^{-1}$; NMR (CDCl$_3$ solution); δ: 5.55–5.35 (2H, m), 5.02–4.6 (3H, m), 4.15–3.75 (1H, m), 1.92 (3H, s), 1.0–0.8 (6H, t);

(4) 2-Oxa-3-hydroxy-6-syn-[3-(2-tetrahydropyranyloxy)-5-ethyloct-trans-1-enyl]-7-anti-(2-tetrahydropyranyloxy)cis-bicyclo[3,3,0]octane 11.5 g. of 2-oxa-3-oxo-6-syn-(3-hydroxy-5-ethyloct-trans-1-enyl)-7-anti-acetoxy-cis-bicyclo[3,3,0]octane (prepared as described in (3) above) were dissolved in 100 ml. of absolute methanol and stirred with 4.6 g. of potassium carbonate at room temperature for 30 minutes. The reaction mixture was then acidified with 1N hydrochloric acid and stirred for 5 minutes. Then the reaction mixture was diluted with 1 litre of ethyl acetate, washed with a saturated aqueous sodium bicarbonate solution and a saturated aqueous sodium chloride solution, dried over magnesium sulphate and concentrated under reduced pressure to give 10 g. of 2-oxa-3-oxo-6-syn-(3-hydroxy-5-ethyloct-trans-1-enyl)-7-anti-hydroxy-cis-bicyclo[3,3,0]octane as a pale yellow oil having the following physical characteristic:

TLC (developing solvent methylene chloride - methanol = 20:1); Rf = 0.24.

9.6 g. of the above diol were dissolved in 100 ml. of methylene chloride, treated with 11 ml. of dihydropyran and 100 mg. of p-toluenesulphonic acid and stirred at room temperature for 15 minutes. The reaction mixture was adjusted to pH 8 with powdered sodium bicarbonate, diluted with 700 ml. of ethyl acetate, washed with water and a saturated aqueous sodium chloride solution, dried over magnesium sulphate and concentrated under reduced pressure to give 15.6 g. of 2-oxa-3-oxo-6-syn-[3-(2-tetrahydropyranyloxy)-5-ethylocttrans-1-enyl]-7-anti-(2-tetrahydropyranyloxy)cis-bicyclo[3,3,0]octane as a yellow oil having the following physical characteristic:

TLC (developing solvent methylene chloride - methanol = 20:1); Rf = 0.79.

15.2 g. of the above bis-(2-tetrahydropyranyl)ether were dissolved in 400 ml. of toluene and, after cooling to −60°C., 48 ml. of diisobutylaluminium hydride (25% w/v) in toluene were added dropwise with stirring. After subjecting the said ether to reduction for 30 minutes at −60°C., the reaction mixture was treated with 20 ml. of methanol to decompose the excess of diisobutylaluminium hydride. Then the reaction mixture was warmed to 0°C. and 40 ml. of water were added to the mixture. The resulting precipitate was filtered off and the filtrate was extracted with diethyl ether. The organic phase was washed with a saturated aqueous sodium chloride solution, dried over magnesium sulphate and concentrated under reduced pressure to give 15.3 g. of the title compound as a light yellow oil having the following physical characteristics:

TLC (developing solvent methylene chloride - methanol = 20:1); Rf = 0.39; IR (neat); $\nu$: 3430, 2950, 2870, 1670, 1450, 1380, 1360, 1290, 1190, 1130, 1080, 1020, 980, 920, 875, 820 cm$^{-1}$; NMR (CDCl$_3$ solution); $\delta$: 5.7–5.15 (2H, m), 4.85–4.25 (3H, m), 4.2–3.15 (8H, m), 1.0–0.8 (6H, t).

(5) 9$\alpha$-Hydroxy-11$\alpha$,15-bis-(2-tetrahydropyranyloxy)-17-ethylprosta-cis-5,trans-13-dienoic acid 5.25 g. of sodium hydride (63.9% content) were suspended in 60 ml. of dimethyl sulphoxide and stirred with heating at 72° to 75°C. for 1 hour to obtain sodiomethylsulphinylcarbanide. The reaction mixture was allowed to cool to room temperature and was then added dropwise to a solution of 31 g. of 4-carboxy-n-butyltriphenylphosphonium bromide in 60 ml. of dimethyl sulphoxide, the reaction temperature being kept within the range of 20° to 30°C.

A solution of 13 g. of 2-oxa-3-hydroxy-6-syn[3-(2-tetrahydropyranyloxy)-5-ethyloct-trans-1-enyl]-7-anti-(2-tetrahydropyranyloxy)-cis-bicyclo[3,3,0]octane (prepared as described in (4) above) in 60 ml. of dimethyl sulphoxide was added and the reaction mixture was stirred vigorously at room temperature for 2 hours. The reaction mixture was then poured into 1 litre of ice-water and neutral substances were removed by extraction with a mixture of ethyl acetate-diethyl ether (1:1). The aqueous layer was acidified to pH 3 with oxalic acid and extracted with a mixture of diethyl ether:n-pentane (1:1). The organic extracts, after washing with water and a saturated aqueous sodium chloride solution, were dried over magnesium sulphate and concentrated under reduced pressure.

Purification of the residue by column chromatography on silica gel using a mixture of benzene:ethanol (100:5) as eluent gave 9.98 g. of the title compound as a pale yellow oil having the following physical characteristics:

TLC (developing solvent methylene chloride - methanol = 20:1); Rf = 0.21; IR (neat); $\nu$: 3450, 2950, 2860 - 2400, 1710, 1450, 1440, 1380, 1120, 1080, 1025, 980, 680 cm$^{-1}$;

(6) 17-Ethyl-PGF$_{2\alpha}$ and 17-ethyl-15-epi-PGF$_{2\alpha}$ 892 mg. of 9$\alpha$-hydroxy-11$\alpha$,15-bis-(2-tetrahydropyranyloxy) -17-ethylprosta-cis-5,trans-13-dienoic acid (prepared as described in (5) above) were dissolved in 25 ml. of a mixture of tetrahydrofuran:acetic acid:water (10:65:35) and stirred at 43°C. for 3 hours. The reaction mixture was then poured into 100 ml. of ice-water and extracted with ethyl acetate. The extracts were washed with water, dried over sodium sulphate and concentrated under reduced pressure. The residue was purified by column chromatography on silica gel using a mixture of cyclohexane-ethyl acetate (7:3) as eluent to give 113 mg. of 17-ethyl-PGF$_{2\alpha}$ (more polar epimer), 162 mg. of 17-ethyl-15-epi-PGF$_{2\alpha}$ (less polar epimer) and 131 mg. of a mixture of the two epimers, having the following physical characteristics:

TLC (developing solvent ethyl acetate - formic acid = 400:5); 17-ethyl-PGF$_{2\alpha}$ : Rf = 0.23; 17-ethyl-15-epi-PGF$_{2\alpha}$ : RF = 0.31; IR (neat) (both epimers); $\nu$: 3350, 2950, 2850–2300, 1705, 1450, 1400, 1240, 1025, 970 cm$^{-1}$; NMR (CDCl$_3$ solution) (both epimers); $\delta$: 5.67–5.22 (4H, m), 5.22–4.90 (4H, broad s), 4.33–3.75 (3H, m), 0.90 (6H, t).

(7) 17-Ethyl-PGE$_2$ and 17-ethyl-15-epi-PGE$_2$ 5.0 g. of 9$\alpha$-hydroxy-11$\alpha$,15-bis-(2-tetrahydropyranyloxy)-17-ethylprosta-cis-5-trans-13-dienoic acid (prepared as described in (5) above) were dissolved in 170 ml. of diethyl ether and cooled at 0°C. Then a chromic acid solution (prepared by dissolving 31 g. of manganese sulphate, 6.5 g. of chromium trioxide and 7.2 ml. of sulphuric acid in 130 ml. of water) was added, and the reaction mixture was stirred vigorously for 3 hours at 0° to -5°C. The reaction mixture was extracted with diethyl ether. The ethereal extract was washed with water thoroughly until the washing was not coloured yellow and dried over magnesium sulphate. The solution was concentrated under reduced pressure.

The residue was dissolved in 80 ml. of a mixture of tetrahydrofuran:acetic acid: water (10:65:35) and stirred at 38° to 40°C. for 3 hours. The reaction mixture was poured into 300 ml. of ice-water, extracted with ethyl acetate, washed with water, dried over magnesium sulphate and concentrated under reduced pressure. The residue was purified by column chromatography on silica gel using a mixture of cyclohexane:ethyl acetate (3:1) as eluent to give 552 mg. of 17-ethyl-PGE$_2$ (more polar epimer), 725 mg. of 17-ethyl-15-epi-PGE$_2$ (less polar epimer) and 410 mg. of a mixture of the two epimers, having the following physical characteristics:

TLC (developing solvent chloroform-tetrahydrofuran-acetic acid = 10:2:1); 17-ethyl-PGE$_2$: RF = 0.32; 17-ethyl-15-epi-PGE$_2$; Rf = 0.41; IR (neat) (both epimers); $\nu$: 3350, 2950 – 2850, –2300, 1740, 1710, 1450, 1400, 1240, 1160, 1080, 975 cm$^{-1}$; NMR (CDCl$_3$ solution) (both epimers); $\delta$: 5.80–5.18 (7H, m), 4.37–3.85 (2H,m), 2.75 (1 H, d-d), 0.91 (6H,t).

PROCEDURE M

Synthesis of
15-methyl-16-phenylthio-$\omega$-tetranor-PGF$_{2\alpha}$ (1) 2-Oxa-3-oxo-6-syn-(2-methoxycarbonyleth-trans-1-enyl)-7-anti-acetoxy-cis-bicyclo[3,3,0]octane Under an atmosphere of nitrogen and at laboratory temperature, 140 ml. of absolute methylene chloride and 16.1 ml. of absolute pyridine were stirred with 10 g. of chromium trioxide for 30 minutes. 20 g. of infusorial earth were then added to the solution. After cooling the temperature to 0°C., 214 g. of 2-oxa-3-oxo-6-syn-hydroxymethyl-7-anti-acetoxy-cis-bicyclo[3,3,0]octane [prepared as described in J. Amer. Chem. Soc., 92, 397 (1970)] in 20 ml. of methylene chloride were then added and the mixture stirred for 15 minutes at 0°C. The reaction mixture was then treated with 25 g. of sodium bisulphate and stirred for a further 10 minutes at 0°C. and filtered through a pad of magnesium sulphate. The filtrate was then concentrated under reduced pressure and below 0°C. to give 2-oxa-3-oxo-6-syn-formyl-7-anti-acetoxy-cis-bicyclo[3,3,0]octane.

369 mg. of sodium hydride (65% content) were suspended in 60 ml. of absolute tetrahydrofuran. With stirring under an atmosphere of nitrogen at room temperature, 1.82 g. of trimethyl phosphonoacetate [prepared as described in Acad. Sci. Paris, Ser. A, B 262B, 515 (1966)] were added to the suspension, and stirred for 30 minutes.

The formyl compound, obtained above, in 30 ml. of tetrahydrofuran, was added, whilst maintaining the temperature below 15°C., and stirred for 2 hours at 15°C. Then the reaction mixture was treated with 2 ml. of acetic acid to pH 5 and concentrated slightly. The product was treated with 20 ml. of water and extracted twice with 80 ml. of ethyl acetate (total volume 160 ml.). The organic layer was washed with an aqueous solution of sodium chloride, dried over magnesium sulphate and concentrated under reduced pressure. The residue was purified by column chromatography on silica gel using a mixture of ethyl acetate - benzene (1:4) as eluent to give 2.0 g. of the title compound having the following physical characteristics:-

IR (liquid film); $\nu$: 2970, 1775, 1735, 1710, 1650, 1240, 1160, 1037, 980 cm$^{-1}$; NMR (CDCl$_3$ solution); $\delta$: 6.77 (1H, d), 5.87 (1H, d), 5.00 (2H, m), 3.70 (3H, s), 3.0–1.9 (6H, m), 2.04 (3H, s); TLC (developing solvent ethyl acetate - benzene = 1:2); Rf = 0.38

(2) 2-Oxa-3-oxo-6-syn-(2-methoxycarbonyleth-trans-1-enyl)-7-anti-hydroxy-cis-bicyclo[3,3,0]octane 2.68 g. of 2-oxa-3-oxo-6-syn-(2-methoxycarbonyleth-trans-1-enyl)-7-anti-acetoxy-cis-bicyclo[3,3,0]octane (prepared as described in (1) above) in 30 ml. of absolute methanol and 1.38 g. of potassium carbonate were stirred at room temperature for 15 minutes, successively cooled in an ice-bath and neutralized with 20 ml. of 1N hydrochloric acid. 260 ml. of ethyl acetate and 27 ml. of an aqueous solution of sodium bicarbonate were added to the reaction mixture and separated into two layers. The organic layer was washed with an aqueous solution of sodium chloride, dried over magnesium sulphate and concentrated under reduced pressure to give 1.96 g. of the title compound having the following physical characteristics:-

IR (liquid film); $\nu$: 3430, 1786-1690 (broad), 1650 cm$^{-1}$ ; NMR (CDCl$_3$ solution); $\delta$: 6.82 (1H, dd), 5.90 (1H, d), 4.95 (1H, m), 3.72 (3H, s), 4.30–3.25 (2H, m), and 2.90–1.70 (6H, m); TLC (developing solvent methylene chloride - methanol = 19:1); Rf = 0.38.

(3) 2-Oxa-3-oxo-6-syn-(2-methoxycarbonyleth-trans-1-enyl)- 7-anti-(2-tetrahydropyranyloxy)-cis-bicyclo[3,3,0]octane 2.31 g. of 2-oxa-3-oxo-6-syn-(2-methoxycarbonyl-eth-trans-1-enyl)-7-anti-hydroxy-cis-bicyclo[3,3,0]octane (prepared as described in (2) above) were dissolved in 30 ml. of methylene chloride and stirred with 20 mg. of p-toluenesulphonic acid and 3 ml. of dihydropyran for 15 minutes at room temperature. The reaction mixture was neutralized with an aqueous solution of sodium bicarbonate, diluted with ethyl acetate, washed with an aqueous solution of sodium chloride, dried over magnesium sulphate and concentrated under reduced pressure. The residue was purified by column chromatography on silica gel using a mixture of ethyl acetate - benzene (1:3) as eluent to give 3.0 g. of the title compound as white crystals having the following physical characteristics:

m.p. 85°C.; IR (KBr tablet); $\nu$: 2930, 1770, 1710, 1650, 1343, 1240, 1152 cm$^{-1}$; NMR (CDCl$_3$ solution); $\delta$: 6.78 (1H, dd), 5.84 (1H, d), 4.97 (1H, m), 4.63 (1H, m), 3.71 (3H, s) and 4.30–3.20 (3H, m); TLC (developing solvent ethyl acetate - benzene = 1:2); Rf = 0.34.

(4) 2-Oxa-3-hydroxy-6-syn-(3-hydroxyprop-trans-1-enyl)- 7-anti-(2-tetrahydropyranyloxy)-cis-bicyclo[3,3,0]octane 3.10 g. of 2-oxa-3-oxo-6-syn-(2-methoxycarbonyl-eth-trans-1-enyl)-7-anti-(2-tetrahydropyranyloxy)-cis-bicyclo[3,3,0]octane (prepared as described in (3) above) were dissolved in 100 ml. of toluene and cooled to −65°C. To the solution, 23 ml. of a 25(w/v)% solution of diisobutylaluminium hydride in toluene were added and stirred for 20 minutes at −60°C. Methanol was then added to decompose excess diisobutylaluminium hydride and water was added. The precipitate was filtered off and the filtrate was dried and concentrated under reduced pressure to give 2.8 g. of the title compound having the following physical characteristics:-

IR (liquid film); $\nu$: 3390, 2930, 1350, 1120 cm$^{-1}$; NMR (CDCl$_3$ solution); $\delta$: 5.75–5.15 (3H, m) and 4.75–3.34 (8H, m); TLC (developing solvent methylene chloride - methanol = 19:1); Rf = 0.23.

(5) 2$\alpha$-(6-Methoxycarbonylhex-cis-2-enyl)-3$\beta$-(3-hydroxy-prop-trans-1-enyl)-4$\alpha$-(2-tetrahydropyranyloxy)-cyclopentan-1$\alpha$-ol 2.94 g. of sodium hydride (65% content) were suspended in 40 ml. of dimethyl sulphoxide and stirred with heating at 65°C. for 40 minutes to obtain sodiomethylsulphinylcarbanide. The reaction mixture was allowed to cool to room temperature and then added dropwise to a solution of 18.5 g. of 4-carboxy-n-butyl-triphenylphosphonium bromide in 40 ml. of dimethyl sulphoxide, the reaction temperature being kept within the range of 20°C. to 25°C.

A solution of 2.84 g. of 2-oxa-3-hydroxy-6-syn-(3-hydroxyprop-trans-1-enyl)-7-anti-(2-tetrahydropyranyl-oxy)-cis-bicyclo[3,3,0]octane (prepared as described in (4) above) in 40 ml. of dimethyl sulphoxide was added, and the mixture stirred vigorously at 25°C. for 1 hour. The reaction mixture was poured into 500 ml. of ice-water and neutral substances were removed by extraction with a mixture of ethyl acetate and diethyl ether (1:1). The aqueous layer was acidified to pH 3 with a saturated solution of oxalic acid and extracted with a mixture of diethyl ether and ethyl acetate (1:1). The extracts, after washing with water, were dried over magnesium sulphate and concentrated under reduced pressure to give crude 2$\alpha$-(6-carboxyhex-cis-2-enyl)-3$\beta$-(3-hydroxyprop-trans-1-enyl)-4$\alpha$-(2-tetrahydropyranyloxy)cyclopentane-1$\alpha$-ol having the following physical characteristics:

IR (liquid film); $\nu$: 2930, 1720, 1240, 1120 cm$^{-1}$; NMR (CDCl$_3$ solution); $\delta$: 5.70–5.25 (4H, m) and 4.62 (1H, m); TLC (developing solvent methylene chloride - methanol = 19:1); Rf = 0.23.

The crude 6-carboxy compound thus obtained was dissolved in 40 ml. of methylene chloride, cooled to 0°C. and a solution of diazomethane in diethyl ether was added until the reaction mixture was coloured pale yellow. The reaction mixture was then concentrated under reduced pressure and the residue was subjected to column chromatography on silica gel using a mixture of ethyl acetate - cyclohexane (1:1) as eluent to give 2.87 g. of the title compound having the following physical characteristics:

IR (liquid film); $\nu$: 3420, 2930, 1740, 1435, 1020 cm$^{-1}$; NMR (CDCl$_3$ solution); $\delta$: 5.75–5.20 (4H, m), 4.67 (1H, m), 4.20–3.30 (6H, m) and 3.67 (3H, s); TLC (developing solvent ethyl acetate - cyclohexane = 2:1); Rf = 0.31.

(6) 2α-(6-Methoxycarbonylhex-cis-2-enyl)-3β-(2-formyleth-trans-1-enyl)-4α-(2-tetrahydropyranyloxy)-cyclopentan-1α-ol 3.8 g. of active manganese dioxide were added to a solution of 382 mg. of 2α-(6-methoxycarbonylhex-cis-2-enyl)-3β-(3-hydroxyprop-trans-1-enyl)-4α-(2-tetrahydropyranyloxy)-cyclopentan-1α-ol (prepared as described in (5) above) in 30 ml. of methylene chloride, the mixture stirred at room temperature for 2 hours and filtered. The insoluble substance was washed thoroughly with acetone, and the filtrate and washing were combined and concentrated under reduced pressure. The residue was purified by column chromatography on silica gel using a mixture of ethyl acetate - benzene (1:4) as eluent to give 266 mg. of the title compound having the following physical characteristics:

IR (liquid film); $\nu$: 3450, 2930, 1737, 1688, 1632, 1435, 1125, 1022, 977 cm$^{-1}$; NMR (CDCl$_3$ solution); $\delta$: 9.56 (1H, d), 6.82 and 6.79 (1H, dd, respectively), 6.20 and 6.18 (1H, dd, respectively), 5.36 (2H, m), 4.58 (1H, m), 3.61 (3H, s) and 4.30–3.20 (4H, m); TLC (developing solvent ethyl acetate - benzene = 1:2); Rf = 0.27.

(7) 1α-Acetoxy-2α-(6-methoxycarbonylhex-cis-2-enyl)-3β-(2-formyleth-trans-1-enyl)-4α-(2-tetrahydropyranyloxy)-cyclopentane 380 mg. of 2α-(6-methoxycarbonylhex-cis-2-enyl)-3β-(2-formyleth-trans-1-enyl)-4α-(2-tetrahydropyranyloxy)-cyclopentan-1α-ol (prepared as described in (6) above) were dissolved in 1.61 ml. of pyridine and 1.87 ml. of acetic anhydride were added and stirred at room temperature for 5 hours. The reaction mixture was concentrated under reduced pressure, the residue was dissolved in 50 ml. of ethyl acetate and 5 ml. of 0.05N hydrochloric acid were added. After separation into two layers, the organic layer was washed with an aqueous solution of sodium chloride, dried over magnesium sulphate and concentrated under reduced pressure. The residue was purified by column chromatography on silica gel using a mixture of ethyl acetate - benzene (1:4) as eluent to give 380 mg. of the title compound having the following physical characteristics: IR (liquid film); $\nu$: 2930, 1737, 1687, 1636, 1244, 1127, 1030 cm$^{-1}$; NMR (CDCl$_3$ solution); $\delta$: 9.56 (1H, d), 6.82 and 6.79 (1H, each dd), 6.26 and 6.23 (1H, each dd), 5.34 (2H, m), 5.11 (1H, m), 4.56 (1H, m), 4.27–3.25 (3H, m), 3.67 (3H, s), 2.09 (3H, s) and 3.00–1.26 (18H, m); TLC (developing solvent ethyl acetate - benzene = 1:2); Rf = 0.50.

(8) Methyl 9α-acetoxy-11α-(2-tetrahydropyranyloxy)-15-hydroxy-16-phenylthio-ω-tetranor-prosta-cis-5,trans-13-dienoate 23 ml. of a 0.5N n-butyllithium solution in diethyl ether were added dropwise to a solution of 1.33 ml. of thioanisole in 31 ml. of tetrahydrofuran under an atmosphere of nitrogen at −20°C., and the reaction mixture was stirred at the same temperature for 1 hour. The reaction mixture thus obtained was added dropwise at −67°C. to a solution of 1.6 g. of 1α-acetoxy-2α-(6-methoxycarbonylhex-cis-2-enyl)-3β-(2-formyleth-trans-1-enyl)-4α-(2-tetrahydropyranyloxy)-cyclopentane (prepared as described in (7) above) in 20 ml. of tetrahydrofuran and the reaction mixture was stirred at that temperature for a further 20 minutes, acidified with acetic acid, diluted with water and extracted with ethyl acetate. The organic extracts were washed with aqueous sodium bicarbonate and aqueous sodium chloride solutions, dried and concentrated under reduced pressure. The residue was purified by column chromatography on silica gel using a mixture of benzene and ethyl acetate (6:1) to give 1.90 g. of the title compound having the following physical characteristics:

TLC (developing solvent benzene - ethyl acetate = 2:1); Rf = 0.31 and 0.42; IR (liquid film); $\nu$: 3430, 2930, 2850, 1730, 1580, 1435, 1370, 1250, 1025, 975, 920, 870 cm$^{-1}$; NMR (CDCl$_3$ solution); $\delta$: 7.7–7.2 (5H, m), 5.9–5.6 (2H, m), 5.6–5.3 (2H, m), 5.3–4.9 (1H, m), 4.9–4.5 (1H, m), 4.5–3.3 (5H, m), 3.73 (3H, s), 3.12 (2H, d), 2.33 (2H, t), 2.1 (3H, s).

(9) Methyl 9α-acetoxy-11α-(2-tetrahydropyranyloxy)-15-oxo-16-phenylthio-ω-tetranorprosta-cis-5,trans-13-dienoate 7.93 of pyridine and 5.0 g. of chromium trioxide were added to 119 ml. of methylene chloride and the mixture was stirred at room temperature under an atmosphere of nitrogen for 15 minutes. 21.2 g. of infusorial earth were then added. The reaction mixture was cooled to 0°C. and then at that temperature a solution of 4.4 g. of methyl 9α-acetoxy-11α-(2-tetrahydropyranyloxy)-15-hydroxy-16-phenylthio-ω-tetranorprosta-cis-5,trans-13-dienoate (prepared as described in (8) above) in 20 ml. of methylene chloride was added. After stirring for 1.5 hours, 35 g. of sodium bisulphate were added and stirring continued for a further 10 minutes. The reaction mixture was filtered on a pad of magnesium sulphate and the filtrate concentrated under reduced pressure. The residue was purified by column chromatography on silica gel using a mixture of benzene and ethyl acetate (6:1) as eluent to give 1.50 g. of the title compound having the following physical characteristics: TLC (developing solvent benzene - ethyl acetate = 2:1); Rf = 0.82; IR (liquid film); $\nu$: 3450, 2940, 2850, 1740, 1695, 1630, 1590, 1485, 1440, 1380, 1250, 1200 cm$^{-1}$; NMR (CDCl$_3$ solution); $\delta$: 7.60–7.10 (5H, m), 6.90–6.20 (2H, m), 5.55–4.95 (3H, m), 4.75–4.40 (1H, m), 4.40–3.20 (8H, m).

(10) Methyl 9α-acetoxy-11α-(2-tetrahydropyranyloxy)-15-hydroxy-15-methyl-16-phenylthio-ω-tetranorprosta-cis-5, trans-13-dienoate A methylmagnesium iodide ether solution [prepared from 64 mg. of magnesium (ribbon), 378 mg. of methyl iodide and 6 ml. of diethyl ether] was added dropwise at 0°C. to a solution of 964 mg. of methyl 9α-acetoxy-11α-(2-tetrahydropyranyloxy-15-oxo-16-phenylthio-ω-tetranorprosta-cis-5,trans-13-dienoate (prepared as described in (9) above) in 20 ml. of diethyl ether, and the reaction mixture was stirred for 1 hour. A small amount of 1N acetic acid was then added to the reaction mixture, which was extracted with ethyl acetate. The organic extracts were washed with water and an aqueous sodium chloride solution, dried over magnesium sulphate and concentrated under reduced pressure. The residue was purified by column chromatography on silica gel using a mixture of benzene and ethyl acetate (6:1) as eluent to give 415 mg. of the title compound having the following physical characteristic:

TLC (developing solvent benzene-ethyl acetate = 2:1); Rf = 0.60; IR (liquid film); ν: 3450, 2950, 2860, 1730, 1620, 1590, 1482, 1440, 1380, 1250, 1140, 1080 cm$^{-1}$; NMR (CDCl$_3$ solution); δ: 7.80–7.00 (5H, m), 5.95–4.90 (5H, m), 4.90–4.45 (1H, m), 4.40–3.10 (8H, m).

(11) 9α, 15-Dihydroxy-11α-(2-tetrahydropyranyloxy)-15-methyl-16-phenylthio-ω-tetranorprosta-cis-5,trans-13-dienoic acid 2.9 ml. of a 2N aqueous potassium hydroxide solution were added to a solution of 415 mg. of methyl 9α-acetoxy-11α-(2-tetrahydropyranyloxy)-15-hydroxy-15-methyl-16-phenylthio-ω-tetranorprosta-cis-5,trans-13-dienoate (prepared as described in (10) above) in 3.0 ml. of methanol, and the reaction mixture was stirred at 40°C. for one hour and then concentrated under reduced pressure. The residue was dissolved in ethyl acetate, adjusted to pH 2 with acetic acid and extracted with ethyl acetate. The organic extracts were washed with an aqueous sodium chloride solution, dried over magnesium sulphate and concentrated under reduced pressure to give 387 mg. of the title compound having the following physical characteristics:

TLC (developing solvent benzene - ethyl acetate = 2:1); Rf = 0.12; IR (liquid film); ν: 3400, 2940, 2860, 1720, 1590, 1480, 1440, 1380, 1280, 1250, 1210, 1140 cm$^{-1}$; NMR (CDCl$_3$ solution); δ: 7.70–6.95 (5H, m), 6.30–5.10 (7H, m), 4.85–4.45 (1H, m), 4.35–3.05 (6H, m).

(12) 9α, 11α, 15-Trihydroxy-15-methyl-16-phenylthio-ω-tetranorprosta-cis-5,trans-13-dienoic acid (15-methyl-16-phenylthio-ω-tetranor-PGF$_{2α}$ )

387 mg. of 9α,15-dihydroxy-11α-(2-tetrahydropyranyloxy)-15-methyl-16-phenylthio-ω-tetranor-prosta-cis-5,trans-13-dienoic acid (prepared as described in (11) above) were dissolved in a mixture of 3.9 ml. of tetrahydrofuran, 1.69 ml. of water and 0.23 ml. of 12N hydrochloric acid and the solution stirred at 40°C. for 1 hour. 178 mg. of sodium bicarbonate were added to the reaction mixture, which was then extracted with ethyl acetate. The organic extracts were washed with an aqueous sodium chloride solution and concentrated under reduced pressure. The residue was purified by column chromatography on silica gel using a mixture of cyclohexane and ethyl acetate (1:1) as eluent to give 57 mg. of the title compound having the following physical characteristics:

TLC (developing solvent chloroform - tetrahydrofuran - acetic acid = 10:2:1); Rf = 0.27; IR (liquid film); ν: 3370, 2930, 2640, 1715, 1590, 1482, 1440, 1410, 1380, 1250, 1100, 1035 cm$^{-1}$; NMR (CDCl$_3$ solution); δ: 7.50–7.10 (5H, m), 5.70–5.25 (4H, m), 4.80–4.40 (4H, m), 4.25–3.80 (2H, m), 3.30–2.90 (2H, m).

PROCEDURE N

Synthesis of 9α,11α,15α-trihydroxy-16-phenylthio-ω-tetranorprosta-cis-5,trans-13-dienaldehyde (1) Methyl 9α-acetoxy-11α-(2-tetrahydropyranyloxy)-15α-hydroxy-16-phenylthio-ω-tetranorprosta-cis-5,trans-13-dienoate and its 15β-hydroxy epimer 37.5 ml. of a 1.6N n-butyllithium solution in diethyl ether were added dropwise to a solution of 6.0 ml. of thioanisole in 60 ml. of tetrahydrofuran under an atmosphere of nitrogen at −10°C. and the reaction mixture was stirred at the same temperature for one hour. The reaction mixture thus obtained was added dropwise at −60°C. to a solution of 12.0 g. of 1α-acetoxy-2α-(6-methoxycarbonylhex-cis-2-enyl)-3β-(2-formyleth-trans-1-enyl)-4α-(2-tetrahydropyranyloxy)-cyclopentane (prepared as described in Procedure M) in 150 ml. of tetrahydrofuran and the reaction mixture was stirred at that temperature for a further 20 minutes, acidified with acetic acid, diluted with water and extracted with ethyl acetate. The organic extracts were washed with aqueous sodium bicarbonate and aqueous sodium chloride solutions, dried over magnesium sulphate and concentrated under reduced pressure. The residue was purified by column chromatography on silica gel using a mixture of cyclohexane and ethyl acetate (4:1) as eluent to give 5.2 g. of the 15α-hydroxy compound, 6.2 g. of the 15β-hydroxy compound and 3.3 g. of a mixture thereof, having the following physical characteristics:

TLC (developing solvent benzene - ethyl acetate = 2:1); 15α-hydroxy compound : Rf = 0.31 15β-hydroxy compound : Rf = 0.42;

IR (liquid film); ν: 3430, 2930, 2850, 1730, 1580, 1435, 1370, 1250, 1025, 975, 920, 870 cm$^{-1}$; NMR (CDCl$_3$ solution); δ: 7.7–7.2 (5H, m), 5.9–5.6 (2H, m), 5.6–5.3 (2H, m), 5.3–4.9 (1H,m), 4.9–4.5 (1H, m), 4.5–3.3 (5H, m), 3.73 (3H, s), 3.12 (2H, d), 2.33 (2H, t), 2.1 (3H, s).

(2) 9α, 15α-Dihydroxy-11α-(2-tetrahydropyranyloxy)-16-phenylthio-ω-tetranorprosta-cis-5,trans-13-dienaldehyde 500 mg. of methyl 9α-acetoxy-11α-(2-tetrahydropyranyloxy)-15α-hydroxy-16-phenylthio-ω-tetranorprosta-cis-5,trans-13-dienoate (prepared as described in (1) above) were dissolved in 12 ml. of toluene and, after cooling to −70°C., 1.14 ml. of a 25(w/v)% solution of diisobutylaluminium hydride in toluene were added dropwise under an atmosphere of nitrogen with stirring. After subjecting the ester to reduction for 30 minutes at −60°C., the reaction mixture was treated with methanol in order to decompose the unreacted diisobutylaluminium hydride. The reaction mixture was warmed to 0° to 5°C. and 15 ml. of water were added to the mixture which was then stirred for 30 minutes. The resulting precipitate was filtered off and the filtrate was separated into two layers. The organic layer was washed with an aqueous sodium chloride solution, dried over magnesium sulphate and concentrated under reduced pressure. The residue was purified by column chromatography on silica gel using a mixture of ethyl acetate and cyclohexane (1:3) as eluent to give 150 mg. of the title compound having the following physical characteristics:

TLC (developing solvent benzene - ethyl acetate = 1:1); Rf = 0.44; IR (liquid film); ν: 3410, 2940, 2850, 1720, 1580, 1480, 1440, 1380, 1360, 1330, 1255, 1205 cm$^{-1}$; NMR (CDCl$_3$ solution); δ: 7.70–7.05 (5H, m), 5.90–5.20 (4H, m), 4.85–4.45 (1H,m).

(3) 9α,11α,15α-Trihydroxy-16-phenylthio-ω-tetranorprosta-cis-5,-trans-13-dienaldehyde 150 mg. of 9α,15α-dihydroxy-11α-(2-tetrahydropyranyloxy)-16-phenylthio-ω-tetranorprosta-cis-5,trans-13-dienaldehyde (prepared as described in (2) above) were dissolved in a mixture of 1.51 ml. of tetrahydrofuran, 0.66 ml. of water and 0.089 ml. of 12N hydrochloric acid and the reaction mixture was stirred at room temperature for 1.5 hours. 69 mg. of sodium bicarbonate were added to the reaction mixture, which was then extracted with ethyl acetate. The organic extracts were washed with an aqueous sodium chloride solution, dried over magnesium sulphate and concentrated under reduced pressure. The residue was purified by column chromatography on silica gel using a mixture of ethyl acetate and cyclohexane (1:1) as eluent to give 97 mg. of the title compound having the following physical characteristics:

TLC (developing solent chloroform-tetrahydrofuranacetic acid = 10:2:1); Rf = 0.32; IR (liquid film); ν: 3350, 2920, 2720, 1720, 1670, 1590, 1480, 1440, 1030, 975 cm$^{-1}$; NMR (CDCl$_3$ solution); δ: 7.48–7.06 (5H, m), 5.60–5.10 (4H, m), 4.30–3.70 (3H, m), 3.60–2.50 (5H, m).

PROCEDURE O

Synthesis of 16-(3-trifluoromethylphenoxy)-9α,11α,15α-trihydroxy-ω-tetranorprosta-cis-5,trans-13-dienaldehyde (1) Dimethyl 2-oxo-3-(3-trifluoromethylphenoxy)propylphosphonate 24 g. of 3-trifluoromethylphenol, 19.2 g. of ethyl chloroacetate, 22.5 g. of sodium iodide and 20.8 g. of potassium carbonate were added to 75 ml. of dry acetone and the reaction mixture was refluxed for 16 hours. Then the reaction mixture was poured into cold aqueous hydrochloric acid and extracted with ethyl acetate. The organic extracts were washed with water and an aqueous sodium chloride solution, dried over magnesium sulphate and concentrated under reduced pressure. The residue was purified by distillation in vacuo to give 29.5 g. of ethyl (3-trifluoromethylphenoxy)acetate having the following physical characteristics:

boiling point: 122° to 125°C./19 mm.Hg; IR (liquid film); ν: 1750, 1590, 1330, 1130 cm$^{-1}$; NMR (CCl$_4$ solution); δ: 7.65–6.90 (4H, m), 4.64 (2H, s), 4.25 (2H, q), 1.25 (3H, t).

33.0 g. of dimethyl methylphosphonate were dissolved in 260 ml. of anhydrous tetrahydrofuran, and 131 ml. of a solution of 2N n-butyllithium in n-hexane were added dropwise whilst maintaining the temperature from −60° to −55°C. After stirring for 30 minutes, 29.5 g. of ethyl (3-trifluoromethylphenoxy)- acetate (obtained as described above) in 100 ml. of anhydrous tetrahydrofuran were added to the solution. The mixture was stirred at the same temperature for 1.5 hours and then at 0°C. for 18 hours. The reaction mixture was neutralized with acetic acid and concentrated under reduced pressure. The residue was dissolved in a small amount of water and extracted with diethyl ether. The ethereal extracts were washed with an aqueous sodium chloride solution, dried over magnesium sulphate and concentrated under reduced pressure. The residue was distilled at 160°C. under a pressure of 0.7 mm.Hg to remove the non-reacted impurities. The resulting residue was purified by column chromatography on silica gel using a mixture of ethyl acetate and cyclohexane (5:1) as eluent to give 26 g. of the title compound having the following physical characteristics:

IR (liquid film); ν: 1730, 1590, 1450, 1050–1030, 750 cm$^{-1}$; NMR (CCl$_4$ solution); δ: 7.50–6.70 (4H, m), 4.70 (2H, s), 3.65 (6H, d), 3.10 (2H, d).

(2) Methyl 9α-acetoxy-11α-(2-tetrahydropyranyloxy)-15-oxo-16-(3-trifluoromethylphenoxy)-ω-tetranorprosta-cis-5,-trans-13-dienoate 760 mg. of sodium hydride (65.1% content) were suspended in 100 ml. of anhydrous tetrahydrofuran. With stirring under an atmosphere of nitrogen, 9.3 g. of dimethyl 2-oxo-3-(3-trifluoromethylphenoxy)propylphosphonate (prepared as described in (1) above) in 40 ml. of tetrahydrofuran were added to the suspension at 30°C. and the mixture stirred for 30 minutes.

4.5 g. of 1α-acetoxy-2α-(6-methoxycarbonylhex-cis-2-enyl)-3β-formyl-4α-(2-tetrahydropyranyloxy)cyclopentane (prepared as described hereafter) in 15 ml. of tetrahydrofuran were added and the mixture stirred at 40°C. for 5 hours. The reaction mixture was then acidified with acetic acid, and silica gel was added to the mixture. The mixture was filtered, and the filtrate concentrated under reduced pressure. The residue was purified by column chromatography on silica gel using a mixture of ethyl acetate and benzene (1:8) as eluent to give 2.66 g. of the title compound having the following physical characteristics:

TLC (developing solvent ethyl acetate - benzene = 1:8); Rf = 0.21; IR (liquid film); ν: 1730, 1690, 1620, 1590, 980 cm$^{-1}$; NMR (CCl$_4$ solution); δ: 7.50–6.20 (6H, m), 5.50–4.75 (3H, m), 4.62 (2H, s), 4.55–4.3 (1H, m), 3.55 (3H, s), 1.99 (3H, s).

1α-Acetoxy-2α-(6-methoxycarbonylhex-cis-2-enyl)-3β-formyl-4α-(2-tetrahydropyranyloxy)-cyclopentane, used as a starting material in the above procedure, was prepared from 2-oxa-3-oxo-6-syn-hydroxymethyl-7-anti-acetoxy-cis-bicyclo[3,3,0]octane, [prepared as described by E. J. Corey et al, J. Am. Chem. Soc., 92 397, (1970)], as follows:

190 g. of 2-oxa-3-oxo-6-syn-hydroxymethyl-7-anti-acetoxy-cis-bicyclo[3,3,0]octane in 1.5 litres of absolute methanol and 130 g. of potassium hydroxide were stirred at room temperature for 1 hour, and then successively cooled in an ice-bath, and neutralized with hydrochloric acid. The precipitate was filtered off and the filtrate was concentrated under reduced pressure. The residue was washed with ethanol, and then with ethyl acetate, and dried to give 124 g. of 2-oxa-3-oxo-6-syn-hydroxymethyl-7-anti-hydroxy-cis-bicyclo[3,3,-0]octane as white crystallites having the following physical characteristics:

m.p. 119°C.; IR (KBr tablet); ν: 3350, 2970–2880, 1740, 1480, 1440, 1410, 1380, 1335, 1305, 1270, 1205, 1100, 1080, 1060, 1040, 1020, 1000, 975 cm$^{-1}$; NMR (CDCl$_3$ + deutero dimethyl sulphoxide solution); δ: 5.10–4.60 (1H, m), 4.29 (2H, s), 4.13–3.77 (1H, m) and 3.38 (2H, d); TLC (developing solvent methylene chloride - methanol = 20:1); Rf = 0.27.

124 g. of 2-oxa-3-oxo-6-syn-hydroxymethyl-7anti-hydroxy-cis-bicyclo[3,3,0]octane obtained above were dissolved in absolute pyridine (1.4 litres) and cooled to −40°C. 74 g. of acetic anhydride were added dropwise and the mixture stirred for 5 hours at −40° to −20°C. and then for 16 hours at 0°C. The pyridine was evaporated off under reduced pressure and the residue was dissolved in 1 litre of ethyl acetate. 200 g. of sodium bisulphate were added, stirred vigorously and filtered. The filtrate was concentrated under reduced pressure and the residue was purified by column chromatography on silica gel using a benzene-ethyl acetate mixture (1:3) as eluent to give 112 g. of 2-oxa-3-oxo-6-syn-acetoxymethyl-7-anti-hydroxy-cis-bicyclo[3,3,0]octane as colourless needles having the following physical characteristics:

m.p. 36° to 37°C.; IR (KBr tablet); $\nu$: 3450, 2960, 2850, 1775, 1740, 1420, 1370, 1250, 1190, 1120, 1090, 1040, 980 cm$^{-1}$; NMR (CDCl$_3$ solution); $\delta$: 5.15–4.60 (1H, m), 4.3–3.75 (3H, m), 3.50 (1H, s) and 2.02 (3H, s); TLC (developing solvent methylene chloride - methanol = 20:1); Rf = 0.50.

43 g. of 2-oxa-3-oxo-6-syn-acetoxymethyl-7-antihydroxy-cis-bicyclo[3,3,0]octane, obtained above, were dissolved in 520 ml. of methylene chloride. 25 g. of dihydropyran and 0.52 g. of p-toluenesulphonic acid were added and the mixture stirred for 20 minutes at room temperature. The reaction mixture was neutralized with an aqueous solution of sodium bicarbonate, diluted with ethyl acetate, washed with water, dried and concentrated under reduced pressure to give 56 g. of 2-oxa-3-oxo-6-syn-acetoxymethyl-7-anti-(2-tetrahydropyranyloxy)-cis-bicyclo[3,3,0]octane as a colourless oil having the following physical characteristics:

IR (liquid film); $\nu$: 2950–2840, 1775, 1740, 1465, 1440, 1390–1340, 1240, 1180, 1140–1120, 1080, 1040, 980 cm$^{-1}$; NMR (CDCl$_3$ solution); $\delta$: 5.2–4.72 (1H, m), 4.72–4.30 (1H, m), 4.2–3.2 (5H, m) and 2.01 (3H, s); TLC (developing solvent methylene chloride - methanol = 20:1); Rf = 0.74.

56 g. of the acetyl ether, prepared above, were dissolved in 900 ml. of toluene and cooled to −60°C. 456 ml. of a 25 (w/v)% toluene solution of diisobutylaluminium hydride were added and the mixture stirred for 20 minutes at the same temperature; methanol was added in order to decompose the excess of diisobutylaluminium hydride and water was added. The resulting precipitate was filtered off and the filtrate was dried and concentrated under reduced pressure to give 35.2 g. of 2-oxa-3-hydroxy-6-syn-hydroxymethyl-7-anti-(2-tetrahydropyranyloxy)-cis-bicyclo[3,3,0]octane as a colourless oil having the following physical characteristics:

IR (liquid film); $\nu$: 3400, 2940–2860, 1465–1440, 1380, 1355, 1325, 1260, 1200, 1140, 1120, 1075, 1020 cm$^{-1}$; TLC (developing solvent ethyl acetate); Rf = 0.25.

37.6 g. of sodium hydride (content 63.5%) were suspended in 400 ml. of dimethyl sulphoxide and stirred at 70°C. for 1.5 hours to obtain sodiomethylsulphinylcarbanide. The reaction mixture was allowed to cool to room temperature and then added dropwise to a solution of 226 g. of 4-carboxy-n-butyltriphenylphosphonium bromide in 460 ml. of dimethyl sulphoxide, the reaction temperature being kept within the range 20° to 25°C.

A solution of 35.2 g. of 2-oxa-3-hydroxy-6-syn-hydroxymethyl-7-anti-(2-tetrahydropyranyloxy)-cis-bicyclo[3,3,0]octane, prepared above, in 90 ml. of dimethyl sulphoxide was added to the above reaction mixture and stirred at 35° to 40°C. for 1.5 hours. The reaction mixture was poured into 6 liters of ice-water and the neutral substances were removed by extraction with an ethyl acetate-diethyl ether mixture (1:1). The aqueous layer was acidified to pH 2 with saturated aqueous oxalic acid solution and extracted with a diethyl ether-n-pentane mixture (1:1). The organic layer was washed with water, dried over sodium sulphate and concentrated under reduced pressure. The residue was subjected to column chromatography on silica gel using a benzene-methanol mixture (10:1) as eluent to give 35 g. of 2α-(6-carboxyhex-cis-2-enyl)-3β-hydroxymethyl-4α-(2-tetrahydropyranyloxy)-cyclopentan-1α-ol as a colourless oil having the following physical characteristics:

IR (liquid film); $\nu$: 3400, 2940–2860, −2300, 1710, 1450, 1435, 1400, 1355, 1245, 1200, 1140, 1120, 1075, 1025 cm$^{-1}$; NMR (CDCl$_3$ solution); $\delta$: 6.20 (3H, s), 5.50–5.10 (2H, m), 4.75–4.36 (1H, m), 4.24–3.85 (2H, m) and 3.85–3.0 (4H, m); TLC (developing solvent chloroform - tetrahydrofuran - acetic acid = 10:2:1); Rf = 0.53.

To a solution of 18.8 g. 2α-(6-carboxyhex-cis-2-enyl)-3β-hydroxymethyl-4α-(2-tetrahydropyranyloxy)cyclopentan-1α-ol, obtained above, in 130 ml. of diethyl ether, a freshly prepared ethereal solution of diazomethane was added with cooling in an ice-bath until the reaction mixture showed a pale yellow colour. The reaction mixture was concentrated in vacuo, and the residue was subjected to column chromatography on silica gel using a cyclohexane-ethyl acetate mixture (2:1) as eluent to give 15.4 g. of 2α-(6-methoxycarbonylhex-cis-2-enyl)-3β-hydroxymethyl-4α-(2-tetrahydropyranyloxy)-cyclopentan-1α-ol as a colourless oil having the following physical characteristics:

IR (liquid film); $\nu$: 3450, 2950–2870, 1740, 1440, 1360, 1325, 1250, 1200, 1140, 1120, 1080, 1025 cm$^{-1}$; NMR (CDCl$_3$ solution); $\delta$: 5.55–5.00 (2H, m), 4.78–4.30 (1H, m), 4.20–3.06 (6H, m), 3.55 (3H, s) and 2.97 (2H, s); TLC (developing solvent methylene chloride-methanol = 19:1); Rf = 0.43.

13.1 g. of 2α-(6-methoxycarbonylhex-cis-2-enyl)-3β-hydroxymethyl-4α-(2-tetrahydropyranyloxy)cyclopentan-1α-ol, obtained above, were dissolved in 250 ml. of absolute methylene chloride, and 25 ml. of pyridine were added. The air in the apparatus was replaced with nitrogen and the contents cooled to −20°C. To the reaction mixture was added dropwise a solution of 5.1 ml. of trimethylchlorosilane in 30 ml. of methylene chloride with stirring and the mixture stirred at the same temperature for 30 minutes. A sample of the product thus obtained had the following physical characteristic:

TLC (developing solvent benzene-ethyl acetate = 2:1); Rf = 0.61.

A solution of 2.9 ml. of acetyl chloride in 20 ml. of methylene chloride was added dropwise to the above reaction mixture and stirred at room temperature for 30 minutes. Then 2 ml. of ethanol were added to decompose the excess of acetyl chloride. Pyridine in the reaction mixture was neutralized by the addition of 50 g. of sodium bisulphate, and the resulting precipitate was filtered off. The filtrate was concentrated under reduced pressure to give a residue having the following physical characteristics:

TLC (developing solvent benzene-ethyl acetate = 2:1); Rf = 0.82.

The residue was dissolved in 300 ml. of ethyl acetate and to the solution 100 ml. of aqueous oxalic acid solution were added and the mixture stirred vigorously at room temperature. The organic layer was separated, washed successively with water, aqueous sodium bisulphate solution, water and saturated aqueous sodium chloride solution, dried with sodium sulphate and concentrated under reduced pressure to give 13.7 g. of crude product. The crude product was subjected to column chromatography on silica gel using a benzene-ethyl acetate mixture (3:1) as eluent to give 7.45 g. of 1α-acetoxy-2α-(6-methoxycarbonylhex-cis-2-enyl)-3β-hydroxymethyl-4α-(2-tetrahydropyranyloxy)- cyclopentane, 2.40 g. of 1α-hydroxy-2α-(6-methoxycarbonylhex-cis-2-enyl)-3β-hydroxymethyl-4α-(2-tetrahydropyranyloxy)cyclopentane, 720 mg. of 1α-hydroxy-2α-(6-methoxycarbonylhex-cis-2-enyl)3β-acetoxymethyl-4α-(2-tetrahydropyranyloxy)-cyclopentane, and 1.45 g. of 1α-acetoxy-2α-(6-methoxycarbonylhex-cis-2-enyl)-3β-acetoxymethyl-4α(2-tetrahydropyranyloxy)-cyclopentane.

1α-Acetoxy-2α-(6-methoxycarbonylhex-cis-2-enyl)-3β-hydroxymethyl-4α-(2-tetrahydropyranyloxy)cyclopentane had the following physical characteristics:

IR (liquid film); ν: 3450, 3000, 2950, 2870, 1740, 1440, 1380, 1330, 1250, 1200, 1160, 1140, 1080, 1030, 980, 920, 875, 815 cm$^{-1}$; NMR (CDCl$_3$ solution); δ: 5.45–5.27 (2H, m), 5.16–4.92 (1H, m), 4.76–4.46 (1H, m), 4.27–3.96 (1H, m), 3.67 (3H, s), 2.98–2.64 (1H, m) and 2.05 (3H, s); TLC (developing solvent benzene-ethyl acetate = 2:1); Rf= 0.27.

Under an atmosphere of nitrogen, 4.4 ml. of pyridine were dissolved in 80 ml. of dichloromethane; 2.88 g. of chromium trioxide were added with stirring and the mixture then stirred for 15 minutes. 12 g. of infusorial earth were added to the reaction mixture, and then there was added a solution of 956 mg. of 1α-acetoxy-2α-(6-methoxycarbonylhex-cis-2-enyl)-3β-hydroxymethyl-4α-(2-tetrahydropyranyloxy)-cyclopentane (prepared as described above) in 20 ml. of dichloromethane. After stirring for 10 minutes, 20 g. of sodium bisulphate was added to the reaction mixture and stirring continued for a further 10 minutes. The resulting precipitate was filtered off and the filtrate was concentrated under reduced pressure. The residue was subjected to silica gel column chromatography using a benzene-ethyl acetate mixture (5:1) as eluent to give 1α-acetoxy-2α-(6-methoxycarbonylhex-cis-2-enyl)-3βformyl-4α-(2-tetrahydropyranyloxy)-cyclopentane as a colourless oil having the following physical characteristics:

IR (liquid film); ν: 3000, 2950, 2860, 2725, 1740, 1440, 1380, 1325, 1255, 1200, 1165, 1140, 1085, 1030, 980, 920, 880, 820 cm$^{-1}$; NMR (CDCl$_3$ solution); δ: 9.85–9.68 (1H, m), 5.45–4.96 (1H, m), 4.68–4.48 (1H, m), 4.48–4.25 (1H, m), 3.67 (3H, s), and 2.08 (3H, s); TLC (developing solvent benzene-ethyl acetate = 2:1); Rf = 0.66.

(3) Methyl 9α-acetoxy-11α-(2-tetrahydropyranyloxy)-15α-hydroxy-16-(3-trifluoromethylphenoxy)-ω-tetranorprosta-cis-5-trans-13-dienoate and its 15β-hydroxy isomer To a solution of 1.04 g. of methyl 9α-acetoxy-11α-(2-tetrahydropyranyloxy)-15-oxo-16-(3-trifluoromethylphenoxy)-ω-tetranorprosta-cis-5,trans-13-dienotate (prepared as described in (2) above) in 20 ml. of methanol, there were added carefully 195 mg. of sodium borohydride whilst keeping the temperature at −50°C. After 20 minutes, the mixture was neutralized with acetic acid and the methanol was evaporated under reduced pressure. The resulting mixture was extracted with ethyl acetate. The organic extracts were washed with an aqueous sodium bicarbonate solution, water and an aqueous sodium chloride solution, dried over magnesium sulphate and concentrated under reduced pressure. The residue was purified by column chromatography on silica gel using a mixture of ethyl acetate and benzene (1:4) as eluent to give 247 mg. of the 15α-hydroxy compound, 288 mg. of the 15β-hydroxy compound and 370 mg. of a mixture thereof, having the following physical characteristics:

TLC (developing solvent ethyl acetate - benzene = 1:2); 15α-hydroxy compound : Rf = 0.42; 15β-hydroxy compound : Rf = 0.47; IR (liquid film); ν: 3420, 1730, 1570, 1440, 980 cm$^{-1}$; MNR (CDCl$_3$solution); δ: 7.60–7.00 (4H, m), 5.95–5.65 (2H, m), 5.60–5.25 (2H, m), 5.25–4.95 (1H, m), 4.80–4.40 (2H, m), 4.02 (2H, d), 3.68 (3H, s), 2.08 (3H, s).

(4) 9α,15α-Dihydroxy-11α-(2-tetrahydropyranyloxy)-16-(3-trifluoromethylphenoxy)-ω-tetranorprosta-cis-5,trans-13-dienaldehyde 247 mg. of methyl 9α-acetoxy-11α-(2-tetrahydropyranyloxy)-15α-hydroxy-16-(3-trifluoromethylphenoxy)-ω-tetranorprosta-cis-5,trans-13-dienoate (prepared as described in (3) above) were dissolved in 15 ml. of toluene and, after cooling to −70°C., 0.94 ml. of a 25(w/v)% solution of diisobutylaluminium hydride in toluene was added dropwise under an atmosphere of nitrogen with stirring. After subjecting the ester to reduction for 15 minutes, the reaction mixture was treated with methanol in order to decompose the unreacted diisobutylaluminium hydride. The reaction mixture was warmed to −20°C. and water was then added to the mixture. The resulting precipitate was filtered off and the filtrate was concentrated under reduced pressure to give 190 mg. of the title compound having the following physical characteristics:

TLC (developing solvent ethyl acetate); Rf = 0.67; IR (liquid film); ν: 3400, 1720, 1590, 1330, 980 cm$^{-1}$; NMR (CDCl$_3$ solution); δ: 9.90–9.75 (1H, m), 7.70–6.80 (4H, m), 5.95–5.30 (4H, m), 4.80–4.30 (2H, m).

(5) 16-(3-Trifluoromethylphenoxy)-9α,11α,15α-trihydroxy-ω-tetranorprosta-cis-5,trans-13-dienaldehyde 160 mg. of 9α,15α-dihydroxy-11α-(2-tetrahydropyranyloxy)-16-(3-trifluoromethylphenoxy)-ω-tetranorprosta-cis-5,trans-13-dienaldehyde (prepared as described in (4) above) were dissolved in a mixture of 3 ml. of tetrahydrofuran and 1 ml. of 1N hydrochloric acid and the reaction mixture was stirred at 45°C. for 1 hour. The reaction mixture was extracted with ethyl acetate and the organic extracts were washed with water and an aqueous sodium chloride solution, dried over magnesium sulphate and concentrated under reduced pressure. The residue was purified by column chromatography on silica gel using a mixture of ethyl acetate and benzene as eluent to give 90 mg. of the title compound having the following physical characteristics:

TLC (developing solvent chloroform - tetrahydrofuran - acetic acid = 10:2:1); Rf = 0.21; IR (liquid film); ν: 3360, 1725, 1590, 1450, 980 cm$^{-1}$; NMR (CDCl$_3$ solution); δ: 9.69 (1H, t), 7.50–6.95 (4H, m), 5.75–5.15 (4H, m), 4.65–4.35 (1H, m), 4.25–3.80 (4H, m), 3.23 (3H, broad s).

PROCEDURE P

Synthesis of 9α,11α,15α-trihydroxy-16-phenoxy-ω-tetranorprosta-cis-5,trans-13-dienaldehyde (1) Dimethyl 2-oxo-3-phenoxypropylphosphonate 40.1 g. of dimethyl methylphosphonate were dissolved in 200 ml. of anhydrous tetrahydrofuran, to which 154 ml. of a 2N n-butyllithium solution in n-hexane were added dropwise whilst maintaining the temperature from −60°C. to −70°C. After stirring for 20 minutes, 15 g. of ethyl phenoxyacetate in 80 ml. of tetrahydrofuran were added to the solution. The mixture was stirred at the same temperature for 2 hours and then at room temperature overnight. The reaction mixture was neutralized with acetic acid and concentrated under reduced pressure. The residue was dissolved in a small amount of water and extracted with diethyl ether. The ethereal extracts were washed with an aqueous sodium chloride solution, dried over magnesium sulphate and concentrated under reduced pressure. The residue was purified by distillation in vacuo to give 18.9 g. of the title compound having the following characteristics:

boiling point: 145° to 150°C./0.1 mm.Hg; IR (liquid film); $\nu$: 2950, 1740, 1600, 1500, 1250, 1040 cm$^{-1}$; NMR (CDCl$_3$ solution); $\delta$: 7.60–6.50 (5H, m), 5.00–4.40 (2H, broad s), 4.10–3.55 (6H, d), 3.55–2.80 (2H, d).

(2) Methyl 9α-acetoxy-11α-(2-tetrahydropyranyloxy)-15-oxo-16-phenoxy-ω-tetranorprosta-cis-5,trans-13-dienoate 1.1 g. of sodium hydride (65.1% content) were suspended in 200 ml. of anhydrous tetrahydrofuran. With stirring under an atmosphere of nitrogen, 7.83 g. of dimethyl 2-oxo-3-phenoxypropylphosphonate (prepared as described in (1) above) in 100 ml. of tetrahydrofuran were added to the suspension at 30°C. and the mixture stirred for 30 minutes.

4.0 g. of 1α-acetoxy-2α-(6-methoxycarbonylhex-cis-2-enyl)-3β-formyl-4α-(2-tetrahydropyranyloxy)cyclopentane (prepared as described in Procedure O) in 200 ml. of tetrahydrofuran were added and the mixture stirred at 40°C. for 3.5 hours. The reaction mixture was then acidified with acetic acid, and silica gel was added to the mixture. The mixture was filtered, and the filtrate concentrated under reduced pressure. The residue was purified by column chromatography on silica gel using a mixture of benzene and ethyl acetate (6:1) as eluent to give 3.82 g. of the title compound having the following physical characteristics:

TLC (developing solvent benzene - ethyl acetate = 2:1); Rf = 0.71; IR (liquid film); $\nu$: 2950, 1740, 1600, 1500, 1380, 1250 cm$^{-1}$; NMR (CDCl$_3$ solution); $\delta$: 7.90–6.20 (7H, m), 5.80–4.90 (3H, m), 4.90–4.35 (3H, m), 4.35–3.10 (6H, m).

(3) Methyl 9α-acetoxy-11α-(2-tetrahydropyranyloxy)-15α-hydroxy-16-phenoxy-ω-tetranorprosta-cis-5,trans-13-dienoate and its 15β-hydroxy isomer To a solution of 3.82 g. of methyl 9α-acetoxy-11α-(2-tetrahydropyranyloxy)-15-oxo-16-phenoxy-ω-tetranorprosta-cis-5,trans-13-dienoate (prepared as described in (2) above) in 50 ml. of methanol, there was added carefully 825 mg. of sodium borohydride whilst keeping the temperature at −40° to −30°C. After 30 minutes, the mixture was neutralized with acetic acid and the methanol was evaporated under reduced pressure. The resulting mixture was extracted with ethyl acetate. The organic extracts were washed with an aqueous sodium bicarbonate solution, water and an aqueous sodium chloride solution, dried over magnesium sulphate and concentrated under reduced pressure. The residue was purified by column chromatography on silica gel using a mixture of ethyl acetate and benzene (1:4) as eluent to give 1.42 g. of the 15α-hydroxy compound, 1.26 g. of the 15β-hydroxy compound an 870 mg. of a mixture thereof, having the following physical characteristics:

TLC (developing solvent ethyl acetate - benzene = 1:2); 15α-hydroxy compound: Rf = 0.42; 15β-hydroxy compound: Rf = 0.51; IR (liquid film); $\nu$: 3420, 1735, 1570, 1440, 980 cm$^{-1}$; NMR (CDCl$_3$ solution); $\delta$: 7.65–7.00 (5H, m), 5.95–5.62 (2H, m), 5.60–5.23 (2H, m), 5.23–4.94 (1H, m), 4.85–4.40 (1H, m), 4.40–3.25 (5H, m), 3.70 (3H, s), 3.12 (2H, d), 2.08 (3H, s).

(4) 9α,15α-Dihydroxy-11α-(2-tetrahydropyranyloxy)-16-phenoxy-ω-tetranorprosta-cis-5,trans-13-dienaldehyde 1.42 g. of methyl 9α-acetoxy-11α-(2-tetrahydropyranyloxy)-15α-hydroxy-16-phenoxy-ω-tetranorprosta-cis-5,trans-13-dienoate (prepared as described in (3) above) were dissolved in 35 ml. of toluene and, after cooling to −70°C., 3.22 ml. of a 25(w/v)% solution of diisobutylaluminium hydride in toluene were added dropwise under an atmosphere of nitrogen with stirring. After subjecting the ester to reduction for 15 minutes, the reaction mixture was treated with methanol in order to decompose the unreacted diisobutylaluminium hydride. The reaction mixture was warmed to −20°C. and water was added to the mixture. The resulting precipitate was filtered off and the filtrate was concentrated under reduced pressure to give 950 mg. of the title compound having the following physical characteristics:

TLC (developing solvent ethyl acetate); Rf = 0.69; IR (liquid film); $\nu$: 3420, 1720, 1600, 1335, 980 cm$^{-1}$; NMR (CDCl$_3$ solution); $\delta$: 9.90–9.70 (1H, m), 7.70–7.00 (5H, m), 5.95–5.32 (4H, m), 4.80–4.30 (1H, m).

(5) 9α,11α,15α-Trihydroxy-16-phenoxy-ω-tetranorprosta-cis-5,trans-13-dienaldehyde 480 mg. of 9α,15α-dihydroxy-11α-(2-tetrahydropyranyloxy)-16-phenoxy-ω-tetranorprosta-cis-5,trans-13-dienaldehyde (prepared as described in (4) above) were dissolved in a mixture of 9 ml. of tetrahydrofuran and 3 ml. of 1N hydrochloric acid and the reaction mixture was stirred at 45°C. for 1 hour. The reaction mixture was extracted with ethyl acetate and the organic extracts were washed with water and an aqueous sodium chloride solution, dried over magnesium sulphate and concentrated under reduced pressure. The residue was purified by column chromatography on silica gel using a mixture of ethyl acetate and benzene (1:2) as eluent to give 278 mg. of the title compound having the following physical characteristics:

TLC (developing solvent chloroform - tetrahydrofuran - acetic acid = 10:2:1); Rf = 0.23; IR (liquid film); $\nu$: 3350, 2940, 1725, 1595, 1450, 980 cm$^{-1}$; NMR (CDCl$_3$ solution); $\delta$: 9.68 (1H, t), 7.50–6.90 (5H, m), 5.72–5.15 (4H, m), 4.65–4.33 (1H, m), 4.24–3.80 (4H, m), 3.20 (3H, broad s).

PROCEDURE Q

Synthesis of 9α,11α,15α-trihydroxy-16-(3-trifluoromethylphenoxy)-ω-tetranorprost-cis-5-enaldehyde (1) 2-Oxa-3-oxo-6-syn-[3-oxo-4-(3-trifluoromethylphenoxy)-but-trans-1-enyl]-7-anti-acetoxy-cis-bicyclo[3,3,0]octane 2.2 g. of sodium hydride (3% content) were suspended in 380 ml. of tetrahydrofuran, and a solution of 20 g. of dimethyl 2-oxo-3-(3-trifluoromethylphenoxy)-propylphosphonate (prepared as described in Procedure O) in 50 ml. of tetrahydrofuran was added. Hydrogen was vigorously generated and the solution became a clear yellow. To the solution obtained a solution of 17 g. of 2-oxa-3-oxo-6-syn-formyl-7-anti-acetoxy-cis-bicyclo[3,3,0]octane (prepared as described in Procedure M) in 40 ml. of tetrahydrofuran was added and the reaction mixture was stirred at 0° to −5°C. for 2.5 hours. It was then neutralized with acetic acid and the resulting precipitate removed by filtration. The filtrate was concentrated under reduced pressure, and the residue was purified by column chromatography on silica gel using a mixture of ethyl acetate and benzene (1:4) as eluent to give 14.2 g. of the title compound having the following physical characteristics:

TLC (developing solvent ethyl acetate - benzene = 1:4); Rf = 0.52; NMR (CDCl$_3$ and CCl$_4$ solution); δ: 7.65–6.15 (6H, m), 5.35–4.50 (4H, m), 1.97 (3H, s).

(2) 2-Oxa-3-oxo-6-syn-[3($\xi$)-hydroxy-4-(3-trifluoromethylphenoxy)-but-trans-1-enyl]-7-anti-acetoxy-cis-bicyclo[3,3,0]octane 13.9 g. of 2-oxo-3-oxo-6-syn-[3-oxo-4-(3-trifluoromethylphenoxy)-but-trans-1-enyl]-7-anti-acetoxy-cis-bicyclo[3,3,0]octane (prepared as described in (1) above) were dissolved in 150 ml. of methanol, and 3.2 g. of sodium borohydride were added whilst maintaining the internal temperature at −40°C. After stirring at −40°C. to −30°C. for 15 minutes, the mixture was neutralized with acetic acid and then concentrated under reduced pressure. The resulting residue was dissolved in ethyl acetate, and the solution was washed successively with an aqueous solution of sodium bicarbonate and an aqueous solution of sodium chloride and then dried over magnesium sulphate. The solvent was distilled off and the residue was purified by column chromatography on silica gel using a mixture of benzene and ethyl acetate (10 to 7:1) as eluent to give 12.8 g. of the title compound having the following physical characteristics:

IR (liquid film); ν: 3450, 2930, 2855, 1775, 1740, 1600, 1500, 1450, 1340, 1250, 1170, 1030, 1075, 980 cm$^{-1}$; NMR (CDCl$_3$ solution); δ: 7.65–6.90 (4H, m), 5.90–5.55 (2H, s), 5.25–4.72 (2H, m), 4.72–4.30 (1H, m), 3.98 (2H, s), 3.20–2.70 (1H, broad s), 2.02 (3H, s); TLC (developing solvent methylene chloride - methanol = 20:1); Rf = 0.43.

(3) 2-Oxa-3-oxo-6-syn-[3($\xi$)-hydroxy-4-(3-trifluoromethylphenoxy)-but-trans-1-enyl]-7-anti-hydroxy-cis-bicyclo[3,3,0]octane 8.3 g. of 2-oxa-3-oxo-6-syn[3($\xi$)-hydroxy-4-(3-trifluoromethylphenoxy)-but-trans-1-enyl]-7-anti-acetoxy-cis-bicyclo[3,3,0]octane (prepared as described in (2) above), 2.764 g. of potassium carbonate and 70 ml. of methanol were mixed and stirred at room temperature for 30 minutes. The reaction mixture was neutralized with 1N hydrochloric acid and extracted with ethyl acetate. The extracts were washed with an aqueous solution of sodium chloride, dried over magnesium sulphate and concentrated under reduced pressure. The residue was purified by column chromatography on silica gel using a mixture of benzene and ethyl acetate (1:3) as eluent to give 5.9 g. of the title compound having the following physical characteristics:

IR (liquid film); ν: 3400, 3060, 2940, 2860, 1770, 1600, 1500, 1455, 1380, 1340, 1250, 1170, 1130, 1075, 1045, 980 cm$^{-1}$; NMR (CDCl$_3$ solution); δ: 7.60–6.80 (4H, m), 5.85–5.48 (2H, m), 5.10–4.65 (1H, m), 4.65–4.20 (1H, m), 4.20–3.10 (5H, m); TLC (developing solvent ethyl acetate - benzene = 3:1, twice); Rf = 0.42.

(4) 2-Oxa-3-oxo-6-syn-[3($\xi$)-hydroxy-4-(3-trifluoromethylphenoxy)-butyl]-7-anti-hydroxy-cis-bicyclo[3,3,0]octane 300 mg. of palladium on charcoal were suspended in 30 ml. of methanol. Air in the apparatus was replaced by hydrogen and a solution of 3.254 g. of 2-oxa-3-oxo-6-syn[3($\xi$)-hydroxy-4-(3trifluoromethylphenoxy)-but-trans-1-enyl]-7-anti-hydroxy-cis-bicyclo[3,3,0]octane (prepared as described in (3) above) in 20 ml. of methanol were added. Catalytic reduction of the compound was carried out at room temperature under ambient pressure for one hour. After completion of the reaction, the catalyst was separated by filtration and the filtrate was evaporated to dryness under reduced pressure to give 3.02 g. of the title compound having the following physical characteristics:

IR (liquid film); ν3370, 3060, 2920, 2850, 1760, 1600, 1495, 1450, 1335, 1300, 1240, 1170, 1125, 1070, 1040 cm$^{-1}$; NMR (CDCl$_3$ solution); δ: 7.50–6.82 (4H, m), 5.10–4.75 (1H, m), 4.30–3.58 (4H, m), 3.25–2.80 (2H, broad s).

(5) 2Oxa-3-oxo-6-syn-[3($\xi$)-(2-tetrahydropyranyloxy)-4-(3-trifluoromethylphenoxy)-butyl]-7-anti-(2-tetrahydropyranyloxy)-cis-bicyclo[3,3,0]octane 3.02 g. of 2-oxa-3-oxo-6-syn-[3($\xi$)-hydroxy-4-(3-trifluoromethylphenoxy)-butyl]-7-anti-hydroxy-cis-bicyclo[3,3,0]octane (prepared as described in (4) above) were dissolved in 9.3 ml. of methylene chloride, and the solution was reacted with 2.0 ml. of dihydropyran and 17.3 mg. of p-toluenesulphonic acid at 18° to 25°C. for 15 minutes to give 4.7 g. of the title compound having the following physical characteristics:

IR (liquid film); ν: 2940, 2850, 1770, 1595, 1495, 1440, 1330, 1240, 1200, 1170, 1135, 1075, 1035 cm$^{-1}$; NMR (CDCl$_3$ solution); δ: 7.60–6.90 (4H, m), 5.20–4.40 (3H, m), 4.40–3.20 (8H, m); TLC (developing solvent methylene chloride - methanol = 19:1); Rf = 0.90.

(6) 2-Oxa-3-hydroxy-6-syn-[3($\xi$)-(2-tetrahydropyranyloxy)-4-(3-trifluromethylphenoxy)-butyl]-7-anti-(2-tetrahydropyranyloxy)-cis-bicyclo[3,3,0]octane 4.7 g. of 2-oxa-3-oxo-6-syn-[3($\xi$)-(2-tetrahydropyranyloxy)-4-(3-trifluoromethylphenoxy)-butyl]-7-anti-(2-tetrahydropyranyloxy)-cis-bicyclo[3,3,0]octane (prepared as described in (5) above) were reduced at −50° to −60°C. for 30 minutes using 12.5 ml. of a 25(w/v)% solution of diisobutylaluminium hydride in toluene to give 4.4 g. of the title compound having the following physical characteristics:

IR (liquid film); ν: 3400, 2920, 2850, 1590, 1490, 1440, 1330, 1285, 1235, 1200, 1165, 1130, 1070, 1030 cm$^{-1}$; NMR (CDCL$_3$ solution); δ: 7.60–6.90 (4H, m), 5.70–5.30 (1H, broad s), 5.00–4.30 (3H, m), 4.30–3.0 (9H, m); TLC (developing solvent methylene chloride - methanol = 19:1); Rf = 0.43.

(7) Methyl 9α-hydroxy-11α,15($\xi$)-bis-(2-tetrahydropyranyloxy)-16-(3-trifluromethylphenoxy)-ω-tetranorprost-cis-5-enoate A solution of 21.5 g. of 4-carboxy-n-butyltriphenylphosphonium bromide in 40 ml. of dimethyl sulphoxide were mixed with a solution of sodiomethylsulphinylcarbamide [prepared from 3.6 g. of sodium hydride (63% content) and 50 ml. of dimethyl sulphoxide] whilst maintaining the temprature below 25°C. The solution became scarlet about half way through the addition. A solution of 4.4 g. of 2-oxa-3-hydroxy-6-syn-[3($\xi$)-(2-tetrahydropyranyloxy)-4-(3-trifluoromethylphenoxy)-butyl]-7-anti-(2-tetrahydropyranyloxy)-cis-bicyclo[3,3,0]octane (prepared as described in (6) above)

in 20 ml. of dimethyl sulphoxide were added, and the mixture stirred vigorously at room temperature for one hour. The reaction mixture was poured into 800 ml. of ice-water and neutral substances were removed by extraction with a mixture of ethyl acetate and diethyl ether (1:1). The aqueous layer was acidified to pH 2 with a saturated aqueous oxalic acid solution and extracted with a mixture of diethyl ether and n-pentane (1:1). The extracts were washed with water, dried over magnesium sulphate and concentrated under reduced pressure to give crude 9α-hydroxy-11α,15(ξ)-bis-(2-tetrahydropyranyloxy)-16-(3-trifluoromethylphenoxy)-ω-tetranorprost-cis-5-enoic acid having the following physical characteristics:

TLC (developing solvent methylene chloride - methanol = 19:1); Rf = 0.40.

To a solution of the crude acid, obtained above, in 40 ml. of diethyl ether, a freshly prepared ethereal solution of diazomethane was added with cooling in an ice bath until the reaction mixture showed a pale yellow colour. The reaction mixture was concentrated in vacuo, and the residue was subjected to column chromatography on silica gel using a mixture of cyclohexane and ethyl acetate (2:1) as eluent to give 3.984 g. of the title compound having the following physical characteristics:

IR (liquid film); ν: 3500, 2940, 2850, 1740, 1595, 1495, 1450, 1335, 1250, 1205, 1170, 1130, 1080, 1070, 1035 cm$^{-1}$; NMR (CCl$_4$ solution); δ: 7.50–6.80 (4H, m), 5.75–5.00 (2H, m), 5.00–4.40 (2H, m), 4.40–3.00 (9H, m), 3.60 (3H, s). TLC (developing solvent methylene chloride - methanol = 19:1); Rf = 0.67.

(8)  9α-Hydroxy-11α,15(ξ)-bis-(2-tetrahydropyranyloxy)-16-(3-trifluoromethylphenoxy)-ω-tetranorprost-cis-5-enaldehyde 500 mg. of methyl 9α-hydroxy-11α,15(ξ)-bis(2-tetrahydropyranyloxy)-16-(3-trifluoromethylphenoxy)-ω-tetranorprost-cis-5-enoate (prepared as described in (7) above) were dissolved in 15 ml. of toluene and, after cooling to −60°C. to −55°C., 1.0 ml. of a 25(w/v)% solution of diisobutylaluminium hydride in toluene was added dropwise under an atmosphere of nitrogen with stirring. After subjecting the ester to reduction for 15 minutes, the reaction mixture was treated with methanol in order to decompose the unreacted diisobutylaluminium hydride. The reaction mixture was warmed to −20°C. and water was then added to the mixture. The resulting precipitate was filtered off and the filtrate was concentrated under reduced pressure to give 460 mg. of the title compound having the following physical characteristics:

IR (liquid film); ν: 3450, 2930, 1725, 1595, 1490, 1445, 1330, 1240, 1200, 1180, 1130, 1080, 1035 cm$^{-1}$;

NMR (CDCl$_3$ solution); δ: 9.80 (1H, s), 7.70–6.80 (4H, m), 5.75–5.00 (2H, m), 5.00–4.50 (2H, m), 4.50–3.20 (9H, m); TLC (developing solvent methylene chloride - methanol = 19:1); Rf = 0.48.

(9) 9α,11α,15(ξ)-Trihydroxy-16-(3-trifluoromethylphenoxy)-ω-tetranorprost-cis-5-enaldehyde 460 mg. of 9α-hydroxy-11α,15(ξ)-bis-(2-tetrahydropyranyloxy)-16-(3-trifluoromethylphenoxy)-ω-tetranorprost-cis-5-enaldehyde (prepared as described in (8) above) were dissolved in a mixture of 5 ml. of tetrahydrofuran and 2 ml. of 1N hydrochloric acid, and the reaction mixture was stirred at 40° to 45°C. for one hour. The reaction mixture was then extracted with ethyl acetate and the organic extracts were washed with water and an aqueous solution of sodium chloride, dried over magnesium sulphate and concentrated under reduced pressure. The residue was purified by column chromatography on silica gel using a mixture of ethyl acetate and cyclohexane (1:1) as eluent to give 290 mg. of the title compound having the following physical characteristics:

IR (liquid film); ν: 3400, 2850, 2720, 1595, 1495, 1450, 1380, 1335, 1250, 1175, 1130, 1070, 1050 cm$^{-1}$; NMR (CDCl$_3$ solution); δ: 9.745 (1H, t), 7.50–6.90 (4H, m), 5.70–5.00 (2H, m), 4.30–3.55 (5H, m), 3.55–2.83 (3H, broad s), 2.45 (2H, t-d); TLC (developing solvent chloroform - tetrahydrofuran - acetic acid = 10:2:1); Rf = 0.29.

PROCEDURE R

Synthesis of
15-(2-benzo[b]thienyl)-ω-pentanor-PGE$_{2α}$ methyl ester (1) 1α,4α-Diacetoxy-2α-(6-methoxycarbonylhex-cis-2-enyl)-3β-(2-formyleth-trans-1-enyl)-cyclopentane 11 ml. of acetic anhydride were added to a solution of 4.0 g. of 2α-(6-methoxycarbonylhex-cis-2-enyl)-3β-(2-formyleth-trans-1-enyl)-cyclopentan-1α,4α-diol in 50 ml. of pyridine with ice-cooling and then the reaction mixture was stirred at room temperature overnight. The reaction mixture was then poured into chilled dilute hydrochloric acid and extracted with ethyl acetate. The extracts were washed with an aqueous sodium bicarbonate solution and an aqueous sodium chloride solution, dried over sodium sulphate and concentrated under reduced pressure. The residue was purified by column chromatography on silica gel using a mixture of benzene and ethyl acetate (4:1) as eluent to give 4.12 g. of the title compound having the following physical characteristics:

TLC (developing solvent benzene - ethyl acetate = 2:1); Rf = 0.56; NMR (CDCl$_3$ solution); δ: 9.62 (1H, d), 7.12–6.58 (1H, q), 6.50–5.95 (1H, q), 5.85–4.85 (4H, m), 3.70 (3H, s), 2.12 (3H, s), 2.07 (3H, s); IR (liquid film); ν: 3000, 2940, 2850, 2720, 1730, 1680, 1630, 1430, 1370, 1240, 1170, 1155, 1130, 1050, 1025, 980, 950 cm$^{-1}$.

2α-(6-Methoxycarbonylhex-cis-2-enyl)-3β-(2-formyleth-trans-1-enyl)-cyclopentan-1α,4α-diol, used as starting material in the procedure described above, was prepared as follows:

A solution of freshly prepared diazomethane in diethyl ether was added dropwise to a solution of 1.0 g. of 2α-(6-carboxyhex-cis-2-enyl)-3β-(2-formyleth-trans-1-enyl)-cyclopentan-1α,4α-diol in 100 ml. of ethyl acetate at 0°C. and stirred at the same temperature for 10 minutes. The reaction mixture was then concentrated under reduced pressure and the residue was purified by column chromatography on silica gel using a mixture of benzene and ethyl acetate (1:2) as eluent to give 820 mg. of 2α-(6-methoxycarbonylhex-cis-2-enyl)-3β-(2-formyleth-trans-1-enyl)-cyclopentan-1α,-4α-diol having the following physical characteristics:

NMR (CDCl$_3$ solution); δ: 3.66 (3H, s), 4.00–4.32 (2H, m), 5.25–5.55 (2H, m), 6.17 (1H, d—d), 6.78 (1H, d—d), 9.51 (1H, d); IR (liquid film); ν: 3400, 1730, 1690, 1630, 980 cm$^{-1}$.

2α-(6-Carboxyhex-cis-2-enyl)-3β-(2-formyleth-trans-1-enyl)-cyclopentan-1α,4α-diol, used as a starting material in the procedure described above, was prepared as follows:

28 g. of 2-oxa-3-oxo-6-syn-(2-methoxycarbonyleth-trans-1-enyl)-7-anti-acetoxy-cis-bicyclo[3,3,0]octane (prepared by the procedure described in Procedure M) were dissolved in 1.6 liters of toluene and the solution cooled to −55°C. To that solution, 340 ml. of a 25(w/v)% solution of diisobutylaluminium hydride in toluene were added and the mixture stirred at −40°C. for 20 minutes. Methanol was then added to the reaction mixture in order to decompose excess diisobutylaluminium hydride, and then water was added to the reaction mixture. The precipitate was filtered off and washed throughly with ethanol. The filtrate and the washings were combined and concentrated under reduced pressure to dryness. The residue was washed with acetone to give 13.3 g. of 2-oxa-3-hydroxy-6-syn(3-hydroxyprop-trans-1-enyl)-7-anti-hydroxy-cis-bicyclo[3,3,0]octane as a white powder having the following physical characteristics:

m.p. 131.5 to 132.5°C.; IR (KBr tablet); $\nu$: 3370, 3250, 990, 950 cm$^{-1}$; NMR (dimethyl sulphoxide-d$_6$ solution); $\delta$: 5.98 (1H, d), 5.65–5.30 (3H, m), 4.90–4.50 (2H, m), 4.50–4.20 (1H, m), 3.96 (2H, m) and 3.80–3.40 (1H, m); TLC (developing solvent methylene chloride - methanol = 9:1); Rf = 0.17.

1.84 g. of sodium hydride (65% content) were suspended in 25 ml. of dimethyl sulphoxide and stirred with heating at 65°C. for 40 minutes to obtain sodiomethylsulphinylcarbanide. The reaction mixture was allowed to cool to room temperature and then added dropwise to a solution of 11.1 g. of 4-carboxy-n-butyl-triphenylphosphonium bromide in 16 ml. of dimethyl sulphoxide, the reaction temperature being kept at 25°C.

A solution of 1.0 g. of 2-oxa-3-hydroxy-6-syn(3-hydroxyprop-trans-1-enyl)-7-anti-hydroxy-cis-bicyclo[3,3,0]octane in 15 ml. of dimethyl sulphoxide was added, and the mixture stirred vigorously at 25°C. for 30 minutes and then at 40°C. for 45 minutes. The reaction mixture was then poured into 250 ml. of ice-water and neutral substances were removed by extraction with ethyl acetate. The aqueous layer was acidified with oxalic acid to pH 3 to 4 and extracted thoroughly with ethyl acetate. The extracts were concentrated under reduced pressure. In the course of the concentration, the resulting precipitate was filtered off. The residue was purified by column chromatography on silica gel using a mixture of chloroform and tetrahydrofuran (5:1) and then a mixture of ethyl acetate and ethanol (30:1) as eluents to give 840 mg. of 2$\alpha$-(6-carboxyhex-cis-2-enyl)-3$\beta$-(3-hydroxyprop-trans-1-enyl)-cyclopentan-1$\alpha$,-4$\alpha$-diol as an oil having the following physical characteristics:

IR (liquid film); $\nu$: 3400, 1710, 980, 760 cm$^{-1}$; NMR (CDCl$_3$ - dimethyl sulphoxide-d$_6$ solution); $\delta$: 5.90–4.80 (8H, m), 4.20–3.75 (4H, m), 2.50–1.75 (8H, m) and 1.75–1.30 (4H, m); TLC (developing solvent methylene chloride - methanol = 4:1); Rf = 0.30.

6 g. of active manganese dioxide were added to a solution of 334 mg. of 2$\alpha$-(6-carboxyhex-cis-2-enyl)-3$\beta$-(3-hydroxyprop-trans-1-enyl)-cyclopentan-1$\alpha$,4$\alpha$-diol in 60 ml. of acetone and the mixture stirred at room temperature for 25 hours. The precipitate was filtered off, washed with acetone thoroughly, and the filtrate and the washings were combined and concentrated under reduced pressure.

The residue was purified by column chromatography on silica gel using ethyl acetate as eluent to give 188 mg. of 2$\alpha$-(6-carboxyhex-cis-2-enyl)-3$\beta$-(2-formyleth-trans-1-enyl)-cyclopentan-1$\alpha$,4$\alpha$-diol having the following physical characteristics:

IR (liquid film); $\nu$: 3400, 1720–1680, 980 cm$^{-1}$; NMR (CDCl$_3$ - dimethyl sulphoxide-d$_6$ solution); $\delta$: 9.52 (1H, d), 6.82 (1H, d—d), 6.17 (1H, d—d), 6.00–4.50 (5H, m), 4.25–3.90 (2H, m) and 3.55–2.85 (1H, m); TLC (developing solvent ethyl acetate - formic acid = 400:5); Rf = 0.21.

(2) Methyl 9$\alpha$,11$\alpha$-diacetoxy-15$\alpha$-hydroxy-15-(2-benzo[b]thienyl)-$\omega$-pentanorprosta-cis-5,trans-13-dienoate and its 15$\beta$-hydroxy epimer 1.25 ml. of 1.2N sec-butyllithium in n-pentane were added dropwise to a solution of 200 mg. of benzothiophene in 6 ml. of dry tetrahydrofuran under an atmosphere of nitrogen at −40°C. and the reaction mixture was stirred at −30°C. for one hour and then cooled to −70°C. This solution was then added dropwise at −70°C. to a solution of 380 mg. of 1$\alpha$,4$\alpha$-diacetoxy-2$\alpha$-(6-methoxycarbonylhex-cis-2-enyl)-3$\beta$-(2-formyleth-trans-1-enyl)cyclopentane (prepared as described in (1) above) and the reaction mixture was stirred for 30 minutes at −70°C. and for 30 minutes at −30°C.

An aqueous ammonium chloride solution was added to the reaction mixture, which was then extracted with ethyl acetate. The extracts were washed with water and an aqueous sodium chloride solution, dried over magnesium sulphate and concentrated under reduced pressure. The residue was purified by column chromatography on silica gel using a mixture of benzene and ethyl acetate (5:1) as eluent to give 130 mg. of the title compound, 211 mg. of its 15$\beta$-hydroxy epimer and 121 mg. of a mixture of them, having the following physical characteristics:

TLC (title compound) (developing solvent benzene - ethyl acetate = 2:1); Rf = 0.54; [The Rf value of the 15$\beta$-hydroxy epimer of the title compound was 0.63] NMR (CDCl$_3$ solution); $\delta$: 8.0–7.55 (2H, m), 7.50–7.05 (3H, m), 5.95–5.65 (2H, m), 5.60–4.70 (5H, m), 3.63 (3H, s), 2.06 (3H, s), 2.02 (3H, s); IR (liquid film); $\nu$: 3440, 1740, 1440, 1380, 1250, 1180, 1160, 980 cm$^{-1}$;

(3) 15-(2-Benzo[b]thienyl)-$\omega$-pentanor-PGF$_{2\alpha}$ methyl ester 130 mg. of methyl 9$\alpha$,11$\alpha$-diacetoxy-15$\alpha$-hydroxy-15-(2-benzo[b]thienyl)-$\omega$-pentanorprosta-cis-5,-trans-13-dienoate (prepared as described in (2) above) and 70 mg. of potassium carbonate were added to 2.5 ml. of methanol. The reaction mixture was stirred for 30 minutes at 50°C., neutralized with acetic acid, diluted with water and extracted with ethyl acetate. The extracts were washed with an aqueous sodium bicarbonate solution and an aqueous sodium chloride solution, dried over magnesium sulphate and concentrated under reduced pressure. The residue was purified by column chromatography on silica gel using a mixture of cyclohexane and ethyl acetate (2:3) as eluent to give 96 mg. of the title compound having the following physical characteristics:

TLC (developing solvent chloroform - tetrahydrofuran - acetic acid = 10:2:1); Rf = 0.36; NMR (CDCl$_3$ solution); $\delta$: 7.8–7.5 (2H, m), 7.4–7.0 (3H, m), 6.05–5.52 (2H, m), 5.52–5.0 (3H, m), 4.22–4.01 (1H, m), 4.01–3.8 (1H, m), 3.62 (3H, s), 3.3–2.7 (3H, broad s); IR (liquid film; $\nu$: 3380, 1735, 1440, 980 cm$^{-1}$;

PROCEDURE S

Synthesis of 15-(2-benzofuranyl)-ω-pentanor-PGF$_{2\alpha}$ methyl ester (1) Methyl 9α,11α-diacetoxy-15α-hydroxy-15-(2-benzofuranyl)-ω-pentanorprosta-cis-5,trans-13-dienoate and its 15β-hydroxy epimer 1.25 ml. of 1.2N sec-butyllithium in n-pentane were added dropwise to a solution of 177 mg. of benzofuran in 6 ml. of tetrahydrofuran under an atmosphere of nitrogen at −40°C. and the reaction mixture was stirred at −30°C. for 1 hour and then cooled to −70°C. This solution was then added dropwise at −70°C. to a solution of 380 mg. of 1α,4α-diacetoxy-2α-(6-methoxycarbonylhexcis-2-enyl)-3β-(2-formyleth-trans-1-enyl)-cyclopentane (prepared as described in Procedure R) and the reaction mixture was stirred for 30 minutes at −70°C. and for 30 minutes at −30°C. An aqueous ammonium chloride solution was added to the reaction mixture, which was extracted with ethyl acetate. The extracts were washed with water and an aqueous sodium chloride solution, dried over magnesium sulphate and concentrated under reduced pressure. The residue was purified by column chromatography on silica gel using a mixture of benzene and ethyl acetate (5:1) as eluent to give 153 mg. of the title compound, 171 mg. of its 15β-hydroxy epimer and 126 mg. of a mixture of them, having the following physical characteristics:

TLC (title compound) (developing solvent benzene - ethyl acetate = 2:1); Rf = 0.48; [The Rf value of the 15β-hydroxy epimer of the title compound was 0.55] NMR (CDCl$_3$ solution); δ: 7.75–7.15 (4H, m), 6.69 (1H, s), 6.05–5.75 (2H, m), 5.60–4.75 (5H, m), 3.67 (3H, s), 2.09 (3H, s), 2.06 (3H, s); IR (liquid film); ν: 3410, 1740, 1450, 1438, 1370, 1245, 975 cm$^{-1}$.

(2) 15-(2-Benzofuranyl)-ω-pentanor-PGF$_2$ methyl ester 90 mg. of methyl 9α,11α-diacetoxy-15α-hydroxy-15-(2-benzofuranyl)-ω-pentanorprosta-cis-5,trans-13-dienoate (prepared as described in (1) above) and 50 mg. of potassium carbonate were added to 1.8 ml. of methanol. The reaction mixture was stirred for 30 minutes at 50°C., neutralized with acetic acid, diluted with water and extracted with ethyl acetate. The extracts were washed with an aqueous sodium bicarbonate solution and an aqueous sodium chloride solution, dried over magnesium sulphate and concentrated under reduced pressure. The residue was purified by column chromatography on silica gel using a mixture of cyclohexane and ethyl acetate (1:1) as eluent to give 85 mg. of the title compound having the following physical characteristics:

TLC (developing solvent chloroform - tetrahydrofuran - acetic acid = 10:2:1); Rf = 0.33; NMR (CDCl$_3$ solution) δ: 7.60–7.30 (2H, m), 7.30–7.15 (2H, m), 6.63 (1H, s), 5.95–5.60 (2H, m), 5.50–5.20 (3H, m), 4.25–4.05 (1H, m), 4.05–3.85 (1H, m), 3.64 (3H, s); IR (liquid film); ν: 3350, 1740, 1455, 1440, 1260, 975 cm$^{-1}$;

PROCEDURE T

Synthesis of 9α,11α,15α-Trihydroxy-15-(2-benzo[b]thienyl)-ω-pentanorprosta-cis-5,trans-13-dienaldehyde 162 mg. of methyl 9α,11α-diacetoxy-15α-hydroxy-15-(2-benzo[b]thienyl)-ω-pentanorprosta-cis-5,trans-13-dienoate (prepared as described in Procedure R) were dissolved in 16 ml. of toluene and, after cooling to −70°C., 1.8 ml. of a diisobutylaluminium hydride solution in toluene (25%w/v) were added dropwise under an atmosphere of nitrogen with stirring. After subjecting the said ester to reduction for 15 minutes at the same temperature, the reaction mixture was treated with methanol in order to decompose the unreacted diisobutylaluminium hydride. The reaction mixture was then warmed to 0°C. and 0.5 ml. of water was added to the mixture, which was then stirred for 30 minutes at 25°C. The resulting precipitate was filtered off and the filtrate was washed with aqueous sodium bicarbonate and sodium chloride solutions, dried over magnesium sulphate and concentrated under reduced pressure. The residue was purified by column chromatography on silica gel using a mixture of ethyl acetate and cyclohexane (3:1) as eluent to give 87 mg. of the title compound having the following physical characteristics:

TLC (developing solvent chloroform - tetrahydrofuran - acetic acid = 10:2:1); Rf = 0.16; IR (liquid film); ν: 3380, 1730, 1440, 1375, 1245, 1050, 975 cm$^{-1}$; NMR (CDCl$_3$ solution); δ: 9.64 (1H, t), 7.90–7.50 (2H, m), 7.45–7.10 (3H, m), 5.95–5.57 (2H, m), 5.57–5.20 (3H, m), 4.25–4.05 (1H, m), 4.05–3.85 (1H, m), 3.80–2.60 (3H, broad s).

PROCEDURE U

Synthesis of 9α,11α,15α-trihydroxy-15-(2-benzofuranyl)-ω-pentanorprosta-cis-5,-trans-13-dienaldehyde 160 mg. of methyl 9α,11α-diacetoxy-15α-hydroxy-15-(2-benzofuranyl)-ω-pentanorprosta-cis-5,-trans-13-dienoate (prepared as described in Procedure S) were dissolved in 16 ml. of toluene and, after cooling to −70°C., 1.83 ml. of a diisobutylaluminium hydride solution in toluene (25% w/v) were added dropwise under an atmosphere of nitrogen with stirring. After subjecting the said ester to reduction for 15 minutes at the same temperature, the reaction mixture was treated with methanol in order to decompose the unreacted diisobutylaluminium hydride. The reaction mixture was then warmed to 0°C. and 0.5 ml. of water was added to the mixture, which was then stirred for 30 minutes at 25°C. The resulting precipitate was filtered off and the filtrate was washed with aqueous sodium bicarbonate and sodium chloride solutions, dried over magnesium sulphate and concentrated under reduced pressure. The residue was purified by column chromatography on silica gel using a mixture of ethyl acetate and cyclohexane (3:1) as eluent to give 107 mg. of the title compound having the following physical characteristics:

TLC (developing solvent chloroform - tetrahydrofuran - acetic acid = 10:2:1); Rf = 0.20; IR (liquid film); ν: 3350, 1715, 1445, 1373, 1250, 1045, 975 cm$^{-1}$; NMR (CDCl$_3$ solution); δ: 9.63 (1H, t), 7.60–7.30 (2H, m), 7.30–7.06 (2H, m), 6.63 (1H, s), 6.10–5.50 (2H, m), 5.50–5.10 (3H, m), 4.25–4.05 (1H, m), 4.05–3.80 (1H, m), 3.65–2.80 (3H, broad s).

PROCEDURE V

Synthesis of 15-(2-Benzofuranyl)-ω-pentanor-PGF$_{2\alpha}$ alcohol 140 mg. of methyl 9α,11α-diacetoxy-15α-hydroxy-15-(2-benzofuranyl)-ω-pentanorprosta-cis-5,trans-13-dienoate (prepared as described in Procedure S) were dissolved in 5.6 ml. of tetrahydrofuran and, after cooling to 0°C., 1.6 ml. of a diisobutylaluminium hydride solution in toluene (25% w/v) were added dropwise under an atmosphere of nitrogen with stirring. After subjecting the said ester to reduction for 15 minutes at the same temperature, the reaction mixture was treated with methanol in order to decompose the unreacted diisobutylaluminium hydride. 0.5 ml. of water was then added to the mixture which was then stirred at 25°C. for 30 minutes. The resulting precipitate was filtered off and the filtrate was diluted with ethyl acetate, washed with aqueous sodium bicarbonate and sodium chloride solutions, dried over magnesium sulphate and concentrated under reduced pressure. The residue was purified by column chromatography on silica gel using ethyl acetate as eluent to give 99 mg. of the title compound having the following physical characteristics:

TLC (developing solvent chloroform - tetrahydrofuran - acetic acid = 10:2:1); Rf = 0.091; IR (liquid film); $\nu$: 3350, 1450, 1375, 1250, 1050, 975 cm$^{-1}$; NMR (CDCl$_3$ solution); $\delta$: 7.60–7.35 (2H, m), 7.32–7.05 (2H, m), 6.62 (1H, s), 6.00–5.60 (2H, m), 5.50–5.15 (3H, m), 4.30–4.05 (1H, m), 4.05–3.80 (1H, m), 3.55 (2H, t), 3.45–2.90 (4H, broad s).

PROCEDURE W

Synthesis of 16,16-ethano-PGE$_2$ methyl ester (1) Ethyl 2,2-ethanohexanoate
Method A.

To a suspension of 55 g. (1.48 mol) of sodium hydride in 1000 ml. of dimethyl sulphoxide (dried and distilled from calcium hydride) was added in small portions solid trimethyloxosulphonium iodide (330 g., 1.48 mol) at 20° to 30°C. An exothermic reaction took place with evolution of hydrogen. The flask was surrounded by a water bath and the mixture was stirred for 45 minutes, by which time the evolution of hydrogen had ceased. 100 g. (0.45 mol) of ethyl 2-bromohexanoate (Beil. 2, 325) in 200 ml. of dimethyl sulphoxide were added dropwise to the resulting methylide at 20° to 30°C. Stirring was continued for another 2.5 hours. The mixture was then poured into water (5 l.), extracted with diethyl ether, the ethereal extract washed with water, dried (MgSO$_4$) and concentrated to give crude ethyl 2,2-ethanohexanoate (61 g.). The product was then distilled under reduced pressure. The fraction boiling at 90° to 94°C./25 mm.Hg. was collected. The yield of ethyl 2,2-ethanohexanoate was 19 g. (25%). The compound had the following physical characteristics:

TLC (developing solvent toluene); ethyl 2-bromohexanoate: Rf = 0.71; ethyl 2,2-ethanohexanoate: Rf = 0.59; NMR (CDCl$_3$ solution); $\delta$: 4.02 (2H, q), 1.89–1.23 (2H, m), 1.20–1.05 (2H, dd), 0.95 (3H, t), 0.63–0.55 (2H, dd); IR (neat); $\nu$: 3100, 2950, 2850, 1730, 1470, 1380, 1350, 1220, 1180, 1160, 1100, 1040, 870 cm$^{-1}$.

Method B.

To a suspension of 55 g. (1.48 mol) of sodium hydride in 1000 ml. of dimethyl sulphoxide (dried and distilled from calcium hydride) was added in small portions solid trimethyloxosulphonium iodide (330 g., 1.48 mol) at 20°C. to 30°C. An exothermic reaction took place with evolution of hydrogen. The flask was surrounded by a water bath and the mixture was stirred for 45 minutes, by which time the evolution of hydrogen had ceased. 230 g. (1.48 mol) of ethyl 2-methylenehexanoate [J. Org. Chem., 37, 1257 (1972)] in 500 ml. of dimethyl sulphoxide were added dropwise to the resulting methylide at 20°C. to 30°C. Stirring was continued for another 2.5 hours. The mixture was then poured into water (5 liters), extracted with diethyl ether, the ethereal extract washed with water, dried (MgSO$_4$) and concentrated to give crude ethyl 2,2-ethanohexanoate. The crude product was then distilled under reduced pressure to give 70 g. of the pure title compound having the following physical characteristics:

b.p. 91° to 94°C./25 mm.Hg; TLC (developing solvent toluene); Rf = 0.56; NMR (CDCl$_3$ solution); $\delta$: 4.02 (2H, q), 1.89–1.23 (2H, m), 1.20–1.05 (2H, dd), 0.95(3H, t), 0.63–0.55 (2H, dd); IR (neat); $\nu$: 3100, 2950, 2850, 1730, 1470, 1380, 1350, 1220, 1180, 1160, 1100, 1040, 870 cm$^{-1}$.

(2) Dimethyl 2-oxo-3,3-ethano-n-heptylphosphonate

To 34 g. (0.27 mol) of dimethyl methylphosphonate in 200 ml. of dry tetrahydrofuran, cooled to $-60°C.$, was added dropwise 210 ml. (0.27 mol) of a 1.45M solution of n-butyllithium in diethyl ether. The mixture was stirred at $-60°C.$ for 15 minutes. 20 g. (0.12 mol) of ethyl 2,2-ethanohexanoate (prepared as described in (1) above) in 80 ml. of dry tetrahydrofuran were added at $-60°C.$, and the mixture stirred at $-60°C.$ for 2 hours and then at 0°C. overnight. After warming to room temperature, the mixture was acidified to pH 4 with acetic acid. The formed solid was removed by filtration and the filtrate was evaporated under reduced pressure. The residue was dissolved in 500 ml. of diethyl ether and the insoluble inorganic material was dissolved in 100 ml. of water and separated. The aqueous phase was extracted with diethyl ether and the combined organic phases were washed with saturated aqueous sodium chloride solution, dried (MgSO$_4$) and concentrated. The product was distilled under reduced pressure. The fraction boiling at 100° to 115°C./0.05 mm.Hg was collected. 19 g. of dimethyl 2-oxo-3,3-ethano-n-heptylphosphonate were obtained having the following physical characteristics:

NMR (CDCl$_3$ solution; $\delta$: 3.62 (6H, d), 2.80 (2H, d), 1.70–1.10 (8H, m), 0.95 (3H, t), 0.80–0.70 (2H, dd); IR (neat); $\nu$: 3080, 2950, 2850, 1690, 1460, 1360, 1260, 1040, 880, 810 cm$^{-1}$.

(3) 2-Oxa-3-oxo-6-syn-(3-oxo-4,4-ethano-oct-trans-1-enyl)-7-anti-acetoxy-cis-bicyclo[3,3,0]octane 2.5 g. (0.106 mol) of sodium hydride were suspended in 800 ml. of dry tetrahydrofuran and 27 g. (0.109 mol) of dimethyl 2-oxo-3,3-ethano-n-heptylphosphonate (prepared as described in (2) above) in 50 ml. of dry tetrahydrofuran were added dropwise at 30°C. The mixture was stirred at room temperature for 30 minutes, after which time no further hydrogen was evolved. 23 g. (0.109 mol) of 2-oxa-3-oxo-6-syn-formyl-7-anti-acetoxy-cis-bicyclo[3,3,0]octane (prepared as described in Procedure M) in 100 ml. of dry tetrahydrofuran were added in one portion, and stirring at room temperature was continued for 1 hour. Glacial acetic acid was then added to neutralise (pH 7) the excess base and the solvent was removed in vacuo. The residue was subjected to column chromatography on 1 kg. of silica gel and the product was eluted with benzene-ethyl acetate (3:1) to give 18.8 g. (51%) of the title compound having the following physical characteristics:

TLC (developing solvent 20% ethyl acetate/benzene); Rf = 0.55; NMR (CDCl$_3$ solution); $\delta$: 6.75–6.45 (1H, dd), 6.40–6.15 (1H, d), 5.06 (2H, m), 3.10–3.06 (complex), 2.03 (3H, s), 2.00–1.03 (complex), 0.95

(3H, t), 0.85–0.65 (2H, m); IR (neat); ν: 3100, 2950, 2850, 1780, 1740, 1680, 1630, 1380, 1250, 1180, 1080, 980 cm⁻¹.

(4) 2-Oxa-3-oxo-6-syn-(3-hydroxy-4,4-ethano-oct-trans-1-enyl)-7-anti-acetoxy-cis-bicyclo[3,3,0]octane To a solution cooled to −30°C. of 9.0 g. (0.027 mol) of 2-oxa-3-oxo-6-syn-(3-oxo-4,4-ethano-oct-trans-1-enyl)-7-anti-acetoxy-cis-bicyclo[3,3,0]octane (prepared as described in (3) above) in methanol (100 ml.) were added in small portions 3.2 g. (0.081 mol) of sodium borohydride. The mixture was stirred at −30°C. for 1.5 hours and then acetic acid was added until the pH was 3. The solvent was distilled off in vacuo, and the residue was dissolved in 100 ml. of ethyl acetate. The solution was washed with a saturated aqueous sodium bicarbonate solution, dried (MgSO₄) and concentrated in vacuo to give 8.9 g. of the title compound having the following physical characteristics:

TLC (developing solvent methylene chloride-methanol = 19:1); Rf of bicyclo-octane starting material = 0.84, Rf of bicyclo-octane product = 0.62; NMR (CDCl₃ solution); δ: 5.13 (2H, m), 5.05–4.87 (2H, m), 3.75 (1H, m), 2.83–2.16 (complex), 2.03 (3H, s), 1.77 (1H, m), 1.45–1.11 (complex), 0.96 (3H, t), 0.45–0.30 (4H, m); IR (neat); ν: 3450, 3100, 2950, 2850, 1780, 1740, 1380, 1250, 1180, 1030, 980 cm⁻¹.

(5) 2-Oxa-3-hydroxy-6-syn-(3-hydroxy-4,4-ethano-oct-trans-1-enyl)-7-anti-hydroxy-cis-bicyclo[3,3,0]octane A solution of 1.69 g. (0.199 mol) of diisobutylaluminium hydride in toluene (25 g./100 ml.) was added dropwise to a stirred solution of 8.0 g. (0.024 mol) of 2-oxa-3-oxo-6-syn-(3-hydroxy-4,4-ethano-oct-trans-1-enyl)-7-anti-acetoxy-cis-bicyclo[3,3,0]octane (prepared as described in (4) above) in 100 ml. of toluene and 50 ml. of dry tetrahydrofuran cooled to −60°C. The homogeneous solution was stirred for 15 minutes at −60°C., and then 40 ml. of methanol were added. After warming up to 0°C. and stirring, 70 ml. of water were added, and the solution was stirred for 1 hour at room temperature. The resulting solid was removed by filtration and the filtrate concentrated in vacuo. The residue was dissolved in 100 ml. of ethyl acetate, washed with saturated aqueous sodium chloride solution, dried (MgSO₄) and concentrated to give 6.8 g. of the title compound having the following physical characteristics:

TLC (developing solvent ethyl acetate); Rf of bicyclo-octane starting material =0.82, Rf of bicyclo-octane product = 0.39 and 0.35; (The less polar product on TLC was the C-15 epimer); NMR (CDCl₃ solution); δ: 5.75–5.40 (3H, m), 4.75–4.40 (1H, m), 4.10–3.75 (2H, m), 2.95–1.10 (complex), 0.95 (3H, s), 0.05–0.35 (4H, m); IR (neat); ν: 3450, 3100, 2950, 2850, 1450, 980 cm⁻¹;

(6) 16,16-Ethano-PGF$_{2\alpha}$

A mixture of 8.3 g. (0.345 mol) of sodium hydride and 150 ml. of dry dimethyl sulphoxide was stirred at 75°C. until gas evolution ceased (ca. 1.5 hours). After cooling to room temperature, the solution of sodiomethylsulphinylcarbanide was ready for use.

76 g. (0.175 mol) of 4-carboxy-n-butyl-triphenylphosphonium bromide were dissolved in 150 ml. of dry dimethyl sulphoxide and the solution cooled to 25°C. Then 150 ml. (0.345 mol) of the solution of sodiomethylsulphinylcarbanide (prepared as described above) were added with stirring at 20° to 30°C. to give a red solution. 6.8 g. (0.023 mol) of 2-oxa-3-hydroxy-6-syn-(3-hydroxy-4,4-ethano-oct-trans-1-enyl)-7-anti-hydroxy-cis-bicyclo[3,3,0]-octane (prepared as described in (5) above) in 20 ml. of dimethyl sulphoxide were added in one portion. The mixture was stirred at room temperature for 1 hour and then poured into 1000 ml. of ice-water. The solution was adjusted to pH 9–10 with solid potassium carbonate. Extraction with ethyl acetate-diethyl ether (1:1) removed the neutral components. The aqueous phase was then acidified to pH3 with solid oxalic acid and extracted with ethyl acetate. The acidic extracts were washed with water and saturated aqueous sodium chloride solution, dried (MgSO₄) and concentrated. The product was purified by column chromatography on 360 g. of silica gel using ethyl acetate-cyclohexane (3:1) as eluent to give pure 16,16-ethano-PGF$_{2\alpha}$ (350 mg.) having the following physical characteristics:

TLC (developing solvent chloroform-tetrahydrofuran-ethyl acetate = 10:2:1); Rf = 0.18; The Rf value of the C-15 epimer was 0.29; NMR (CDCl₃ solution); δ: 5.65–5.20 (4H, m), 5.20–4.80 (4H, m), 4.25–3.75 (3H, m), 2.50–1.06 (complex), 0.95 (3H, t), 0.65–0.15 (4H, m); IR (neat); ν: 3350, 3100, 2950, 2850, −2600, 1710, 1420, 1240, 1220, 1100, 1010, 980, 910 cm⁻¹.

(7) 16,16-Ethano-PGF$_{2\alpha}$ methyl ester 300 mg. of 16,16-ethano-PGF$_{2\alpha}$ (prepared as described in (6) above) were dissolved in 40 ml. of diethyl ether and the solution cooled to 0°C. An ethereal solution of 0.24M diazomethane was added until the reaction mixture became pale yellow colour and the evolution of nitrogen ceased. Concentration of the reaction mixture gave 310 mg. of the title compound as a pale yellow oil having the following physical characteristics:

TLC (developing solvent chloroform-tetrahydrofuran-acetic acid = 10:2:1); Rf = 0.30; NMR (CDCl₃ solution); δ: 5.62–5.30 (4H, m), 4.23–4.05 (1H, m), 3.96–3.85 (2H, m), 3.65 (3H, s), 2.50–1.06 (complex), 0.95 (3H, t), 0.65–0.17 (4H, m); IR (neat); ν: 3450, 3010, 2950, 2850, 1740, 1440, 1380, 1320, 1250, 1180, 1110, 1060, 1020, 980 cm⁻¹.

(8) 16,16-Ethano-PGE₂ methyl ester

A mixture of 80 mg. (0.218 mmol) of 16,16-ethano-PGF$_{2\alpha}$ methyl ester (prepared as described in (7) above), 0.6 ml. (0.0031 mol) of N-trimethylsilyldiethylamine and 4 ml. of dry acetone was stirred at room temperature for 2.5 hours. The solution was concentrated in Vacuo to give 11,15-bis-trimethylsilyloxy-16,16-ethano-PGF$_{2\alpha}$ methyl ester as an oil.

290 mg. (0.0029 mol) of chromium trioxide were added in small portions to a mixture of 0.44 ml. (0.0058 mol) of pyridine and 8 ml. of methylene chloride on a water bath. Infusorial earth (1.2 g., dried overnight at 100°C.) was added and the mechanically stirred solution was cooled to 10°C. The silyl ether (obtained as described above) was dissolved in 3 ml. of methylene chloride and the solution added rapidly to the above chromic acid reagent. After 30 minutes stirring at 10°C., the excess chromic acid reagent was destroyed by the addition of 1 ml. of allyl alcohol in 3 ml. of methylene chloride at 0°C., and stirring was continued for 10 minutes at room temperature. Sodium hydrogen sulphate monohydrate (3 g., 0.022 mol) was added at 0°C. and stirring was continued for 10 minutes at room temperature. The mixture was then filtered through a pad of magnesium sulphate. The filtrate was concentrated in vacuo and the residue dissolved in 10 ml. of ethyl acetate. The solution was stirred with 10 ml. of saturated aqueous oxalic acid solution at room temperature for 5 minutes. The aqueous phase was separated and extracted with ethyl acetate. The combined organic phase was washed with water, dried (MgSO$_4$) and concentrated to give the crude 16,16-ethano-PGE$_2$ methyl ester. The product was purified by column chromatography on silica gel using cyclohexane-ethyl acetate (3:2) as eluent to give 10 mg. of the pure title compound having the following physical characteristics:

TLC (developing solvent ethyl acetate-benzene = 2:1); Rf = 0.33; NMR (CDCl$_3$ solution); δ: 5.70–5.52 (2H, m), 5.49–5.25 (2H, m), 4.24–3.80 (2H, m), 3.65 (3H, s), 2.90–1.11 (complex), 0.90 (3H, t), 0.55–0.34 (4H, m); IR (neat); ν: 3400, 3010, 2950, 2850, 1745, 1460, 1440, 1375, 1320, 1255, 1210, 1160, 1080, 980 cm$^{-1}$.

PROCEDURE X

Synthesis of 16(ξ)-methyl-20-hydroxy-PGE$_2$ (1) Ethyl 6-(2-tetrahydropyranyloxy)hexanoate 66 g. (0.412 mol) of ethyl 6-hydroxyhexanoate [prepared as described by S. R. Sandler and W. Karo, in 'Organic Functional Group Preparation', Academic Press, New York, and London, vol. 1, page 262. (cf. G. B. Hatch and H. Adkins, J. Am. Chem. Soc., 59 1694 (1937))] were dissolved in 400 ml. of methylene chloride, and the mixture was reacted with 45 g. of dihydropyran and 1 g. of p-toluenesulphonic acid at 25°C. for 20 minutes. The reaction mixture was washed with an aqueous sodium bicarbonate solution, dried and concentrated. The residue was distilled in vacuo to obtain 77 g. of the title compound having the following physical characteristics:

b.p. 135°C./3 mm.Hg; IR (liquid film); ν: 2940, 2860, 1740, 1445, 1370, 1350, 1325, 1260, 1160, 1140, 1120, 1080, 1040, 985, 910, 870, 820 cm$^{-1}$; NMR (CDCl$_3$ solution); δ: 4.70–4.35 (1H, m), 4.05 (2H, q), 4.00–3.00 (4H, m), 2.24 (2H, t), 1.20 (3H, t).

(2) Ethyl 2(ξ)-methyl-6-(2-tetrahydropyranyloxy)-hexanoate

A solution of 6.2 ml. of diisopropylamine in 50 ml. of tetrahydrofuran was cooled to −70°C., and to it 36 ml. of a solution of n-butyllithium in n-hexane (1.37 molar concentration) were added dropwise and stirred for 15 minutes at −70°C. to give lithium diisopropylamide.

To the lithium diisopropylamide solution 9.0 g. of ethyl 6-(2-tetrahydropyranyloxy)-hexanoate (prepared as described in (1) above) in 20 ml. of tetrahydrofuran were added dropwise at −70°C. and the reaction mixture was stirred for 30 minutes at the same temperature. A solution of 3 ml. of methyl iodide in 20 ml. of tetrahydrofuran was added dropwise to the reaction mixture at −70°C. and stirring was continued for 10 minutes at the same temperature and then for one hour at room temperature. The reaction mixture was then poured into water and extracted with ethyl acetate. The organic extracts were washed with water, dried over magnesium sulphate and concentrated under reduced pressure. The residue was distilled in vacuo to give 6.2 g. of the title compound having the following physical characteristics:

boiling point 129°C. to 132°C./4 mm.Hg; IR (liquid film); ν: 2920, 2850, 1735, 1460, 1380, 1355, 1265, 1205, 1080, 1040 cm$^{-1}$; NMR (CCl$_4$ solution); δ: 4.70–4.50 (1H, m), 4.42 (2H, q), 4.40–3.15 (4H, m), 1.25 (3H, t).

(3) Dimethyl 2-oxo-3(ξ)-methyl-7-(2-tetrahydropyranyloxy)-heptylphosphonate 12 g. of dimethyl methylphosphonate were dissolved in 140 ml. of absolute tetrahydrofuran and 71 ml. of a solution of 1.37M n-butyllithium in n-hexane were added dropwise whilst maintaining the temperature below −50°C. Ten minutes later 12.4 g. of ethyl 2(ξ)-methyl-6-(2-tetrahydropyranyloxy)-hexanoate (prepared as described in (2) above) in 70 ml. of absolute tetrahydrofuran were added dropwise to the solution at −70°C. and the reaction mixture was stirred at the same temperature for 2 hours and then for 16 hours at 4°C.

The reaction mixture was acidified with acetic acid and concentrated under reduced pressure. The residue was dissolved in a small amount of water and extracted with diethyl ether. The ethereal extracts were dried over magnesium sulphate and concentrated under reduced pressure. The residue was distilled at 45° to 59°C. at a pressure of 2 to 4 mm.Hg. The resulting residue was purified by column chromatography on silica gel using ethyl acetate as eluent to give 14.0 g. of the title compound having the following physical characteristics:

IR (liquid film); ν : 2930, 2850, 1715, 1455, 1445, 1375, 1365, 1330, 1260, 1200, 1180, 1140, 1120, 1035, 990 cm$^{-1}$; NMR (CDCl$_3$ solution); δ: 4.70–4.40 (1H, m), 4.15–3.10 (4H, m), 3.77 (6H, d), 3.10 (2H, d).

(4) Methyl 9α-acetoxy-11α,20-bis-(2-tetrahydropyranyloxy)-15-oxo-16(ξ)-methylprosta-cis-5,trans-13-dienoate 1.79 g. of sodium hydride (55% content) were suspended in 240 ml. of absolute tetrahydrofuran. With stirring under an atmosphere of nitrogen at room temperature, 14.0 g. of dimethyl 2-oxo-3(ξ)-methyl-7-(2-tetrahydropyranyloxy)-heptylphosphonate (prepared as described in (3) above) in 130 ml. of tetrahydrofuran were added to the solution, and the mixture stirred for 20 minutes.

14.4 g. of 1α-acetoxy-2α-(6-methoxycarbonylhex-cis-2-enyl)-3β-formyl-4α-(2-tetrahydropyranyloxy)-cyclopentane (prepared as described in Procedure O) in 65 ml. of tetrahydrofuran were added and the mixture stirred for 1 hour at room temperature. The reaction mixture was then neutralized with acetic acid and filtered and th filtrate was concentrated under reduced pressure. The residue was purified by column chromatography on silica gel using a mixture of benzene and ethyl acetate (4:1) as eluent to give 19.8 g. of the title compound having the following physical characteristics:

IR (liquid film); ν: 2960, 2870, 1740, 1700, 1675, 1630, 1455, 1440, 1380, 1360, 1330, 1250, 1200, 1190 – 1150, 1140, 1125, 1080, 1045, 980 cm$^{-1}$; NMR (CDCl$_3$ solution); δ: 6.64 (1H, q), 6.15 (1H, d), 5.60–5.12 (2H, m), 5.10-4.83 (1H, m), 4.83–4.35 (2H, m), 4.35–3.10 (6H, m), 3.62 (3H, s), 2.02 (3H, s); TLC (developing solvent benzene - ethyl acetate = 2:1); Rf = 0.56.

(5) Methyl 9α-acetoxy-11α, 20-bis-(2-tetrahydropyranyloxy)-15α-hydroxy-16(ξ)-methylprosta-cis-5,trans-13-dienoate and the 15β-hydroxy epimer 19.8 g. of methyl 9α-acetoxy-11α,20-bis-(2-tetrahydropyranyloxy)-15-oxo-16(ξ)-methylprosta-cis-5,trans-13-dienoate (prepared as described in (4) above) in 320 ml. of methanol were cooled to −30°C. to −40°C. with stirring. 4.28 g. of sodium borohydride were added in portions. The reaction mixture was then stirred at the same temperature for 30 minutes, and then neutralized with acetic acid. The solvent was removed and the residue was extracted with ethyl acetate. The extracts were washed with an aqueous sodium bicarbonate solution, dried over magnesium sulphate and concentrated under reduced pressure. The residue was purified by column chromatography on silica gel using a mixture of benzene and ethyl acetate (5:1) as eluent to give 7.80 g. of the title compound, 7.13 g. of the 15$\beta$-hydroxy epimer and 4.1 g. of a mixture of them. TLC of the title compound and 15$\beta$-hydroxy epimer gave the following results:

TLC (developing solvent benzene - ethyl acetate = 1:1); the 15$\alpha$-hydroxy compound : Rf = 0.54, the 15$\beta$-hydroxy compound : Rf = 0.64.

The title compound had the following physical characteristics:

IR (liquid film); $\nu$: 3450, 2950, 2860, 1740, 1455, 1380, 1355, 1330, 1250, 1200, 1145, 1125, 1080, 1035, 980 cm$^{-1}$; NMR (CDCl$_3$ solution); $\delta$: 5.65–5.12 (4H, m), 5.12–4.80 (1H, m), 4.75–4.30 (2H, m), 4.30–3.10 (8H, m), 3.60 (3H, s), 2.02 (3H, s).

(6) Methyl 9$\alpha$-acetoxy-11$\alpha$, 15$\alpha$,20-tri-(2-tetrahydropyranyloxy)-16($\xi$)-methylprosta-cis-5,trans-13-dienoate 7.90 g. of methyl 9$\alpha$-acetoxy-11$\alpha$,20-bis-(2-tetrahydropyranyloxy)-15$\alpha$-hydroxy-16($\xi$)-methylprosta-cis-5,trans-13-dienoate (prepared as described in (5) above) were dissolved in 80 ml. of methylene chloride and the solution was reacted with 2.0 ml. of dihydropyran and 37 mg. of p-toluenesulphonic acid at 25°C. for 30 minutes to give 7.2 g. of the title compound having the following physical characteristics:

IR (liquid film); $\nu$: 2950, 2860, 1745, 1460, 1445, 1380, 1340, 1250, 1200, 1190, 1165, 1140, 1080, 1045, 1030, 980 cm$^{-1}$; NMR (CDCl$_3$ solution); $\delta$: 5.65–5.10 (4H, m), 5.10–4.80 (1H, m), 4.80–4.32 (3H, m), 4.24–3.10 (10H, m), 3.60 (3H, s), 2.00 (3H, s); TLC (developing solvent benzene - ethyl acetate = 1:1); Rf = 0.79.

(7) 9$\alpha$-Hydroxy-11$\alpha$,15$\alpha$,20-tri-(2-tetrahydropyranyloxy)-16($\xi$)-methylprosta-cis-5,trans-13-dienoic acid 7.2 g. of methyl 9$\alpha$-acetoxy-11$\alpha$,15$\alpha$,20-tri-(2-tetrahydropyranyloxy)-16($\xi$)-methylprosta-cis-5,trans-13-dienoate (prepared as described in (6) above) were dissolved in a solution of 4.2 g. of potassium hydroxide in a mixture of 7.0 ml. of water and 28 ml. of methanol and stirred at room temperature for 2 hours. The reaction mixture was then neutralized with oxalic acid, extracted with ethyl acetate, washed with water, dried over magnesium sulphate and concentrated under reduced pressure. The residue was purified by column chromatography on silica gel using a mixture of benzene and ethyl acetate (1:2) as eluent to give 5.2 g. of the title compound having the following physical characteristics:

IR (liquid film); $\nu$: 3450, 2950, 2860, −2300, 1740, 1715, 1455, 1380, 1360, 1330, 1250, 1200, 1185, 1140, 1125, 1080, 1040, 980 cm$^{-1}$; NMR (CDCl$_3$ solution); $\delta$: 6.35 (2H, broad s), 5.70–5.14 (4H, m), 4.85–4.30 (4H, m), 4.30–3.00 (11H, m); TLC (developing solvent benzene - ethyl acetate = 1:2); Rf = 0.14.

(8) 9-Oxo-11$\alpha$,15$\alpha$,20-tri-(2-tetrahydropyranyloxy)-16($\xi$)-methylprosta-cis-5,trans-13-dienoic acid 2.14 g. of 9$\alpha$-hydroxy-11$\alpha$,15$\alpha$,20-tri-(2-tetrahydropyranyloxy)-16($\xi$)-methylprosta-cis-5,trans-13-dienoic acid (prepared as described in (7) above) were dissolved in 70 ml. of diethyl ether. The solution was cooled to 0° to 5°C. and then a chromic acid solution (prepared by dissolving 12.4 g. of chromium trioxide, 41 g. of manganese sulphate and 3.0 ml. of sulphuric acid in 51 ml. of water) was added and the reaction mixture was stirred vigorously at 0° to 5°C. for 40 minutes.

The reaction mixture was diluted with diethyl ether and the aqueous layer was separated. The aqueous layer was extracted with diethyl ether. The combined extracts were washed sufficiently with water until the washing was not coloured yellow, dried over sodium sulphate and then concentrated under reduced pressure. The residue was purified by column chromatography on silica gel using a mixture of benzene and ethyl acetate (2:1) as eluent to give 1.73 g. of the title compound having the following physical characteristics:

IR (liquid film); $\nu$: 2940, 2870, −2300, 1745, 1715, 1455, 1445, 1390, 1360, 1325, 1270, 1210, 1195, 1080, 1040, 1025, 908 cm$^{-1}$; NMR (CDCl$_3$ solution); $\delta$: 8.68 (1H, s), 5.75–5.10 (4H, m), 4.90–4.40 (3H, m), 4.35–3.15 (10H, m); TLC (developing solvent benzene - ethyl acetate = 2:3); Rf = 0.53.

(9) 16($\xi$)-Methyl-20-hydroxy-PGE$_2$ 1.73 g. of 9-oxo-11$\alpha$,15$\alpha$,20-tri-(2-tetrahydropyranyloxy)-16($\xi$)-methylprosta-cis-5,trans-13-dienoic acid (prepared as described in (8) above) were dissolved in 55 ml. of a mixture of acetic acid, water and tetrahydrofuran (65:35:10) and stirred at 40°C. for 1 hour. The reaction mixture was then mixed with toluene, and acetic acid was removed by azeotropic distillation. The residue was purified by column chromatography on silica gel using a mixture of ethyl acetate and ethanol (40:1) as eluent to give 690 mg. of the title compound having the following physical characteristics:

IR (liquid film);$\nu$: 3360, 2925, 2855, 1710, 1415, 1382, 1250, 1080, 1040, 978 cm$^{-1}$; NMR (CDCl$_3$ solution); $\delta$: 5.70–5.20 (4H, m), 4.57 (4H, broad s), 4.15–3.80 (2H, m), 3.61 (2H, t), 1.0–0.75 (3H, m); TLC (developing solvent chloroform - tetrahydrofuran - acetic acid = 10:2:1); Rf = 0.05.

PROCEDURE Y

Synthesis of 16,16-propano-$\omega$-nor-PGE$_2$ (1) 2,2-Propanopentanoic acid

To a solution of tetrahydrofuran (285 ml.) and diisopropylamine (56 g., 0.55 mol) in a dry, nitrogenflushed flask, under an atmosphere of nitrogen, was added n-butyllithium (0.55 mol) in hexane and the mixture was magnetically stirred at such a rate as to maintain the temperature below 0°C. To the cold basic solution, cyclobutane carboxylic acid (30.0 g.) was added. After stirring for 30 minutes below 0°C., the reaction mixture was treated with n-propyl bromide (44.2 g.) and, after stirring for a further 2 hours at room temperature, was worked up in the following manner:

The reaction mixture was acidified to about pH 1 with dilute hydrochloric acid (10%) at 0°C. and extracted with petroleum ether. The extract was washed with dilute hydrochloric acid (100 ml. × 5), water, and a saturated aqueous solution of sodium chloride. After drying over sodium sulphate, the extract was concentrated and distilled in vacuo to give 35.0 g. of 2,2-propanopentanoic acid (yield 82.2%) having the following physical characteristics:

b.p. 102° – 108°C./3.0 – 3.5 mm.Hg; NMR (CDCl₃ solution); δ: 11.08 (1H, broad s), 2.41–2.25 (2H, m), 0.89 (3H, broad t); IR (liquid film); ν: 3500 - 2300, 1705 cm⁻¹; Mass spectrum: m/e = 143 (M⁺+1), 142 (M⁺), 125 (M⁺−17), 113 (M⁺−29).

(2) 2,2-Propanopentanoyl chloride

Freshly distilled thionyl chloride was added to 2,2-propanopentanoic acid (35.0 g., prepared as described in (1) above). After stirring for 1.5 hours at room temperature, the temperature of the reaction mixture was raised to 75°C., and kept at that temperature for 2 hours. After removal of thionyl chloride under reduced pressure, the oily residue was distilled in vacuo to give 36.3 g. (yield 92%) of the title compound having the following physical characteristics:

b.p. 30° – 35°C./3 mm.Hg; IR (liquid film);ν: 1800 cm⁻¹.

(3) Dimethyl 2-oxo-3,3-propanohexylphosphonate

A solution of dimethyl methylphosphonate (54 g.) in tetrahydrofuran (300 ml.) was treated with n-butyllithium in hexane (2.3 equivalents relative to the phosphonate) for 30 minutes at −70°C. under an atmosphere of nitrogen. The reaction mixture was further treated with 2,2-propanopentanoyl chloride (32.4 g., prepared as described in (2) above) in tetrahydrofuran (300 ml.) for 5 minutes at −70°C. After stirring for 30 minutes at −70°C. and for 1 hour at room temperature, the reaction mixture was worked up in the following manner:

The reaction mixture was acidified with glacial acetic acid (25ml.), and then concentrated under reduced pressure. The residue was dissolved in water (50 ml.) and extracted with diethyl ether (100 ml. × 5). The aqueous layer was concentrated under reduced pressure, and extracted again with diethyl ether (50 ml. × 3). The combined organic layers were dried over magnesium sulphate, concentrated and distilled in vacuo to yield 39.2 g. (yield 78%) of the title compound having the following physical characteristics:

b.p. 117°–122°C./2 mm.Hg; NMR (CDCl₃ solution); δ: 3.70 (6H, d, J=11.0 Hz), 2.97 (2H, d, J=22.0 Hz), 2.52–2.20 (2H, m), 1.90 –1.60 (6H, m), 1.26–1.00 (2H, m), 0.90 (3H, t, J=6.5 Hz); IR (liquid film); ν: 3450, 1705, 1260, 1060, 1040 cm⁻¹; Mass spectrum: m/e = 248 (M⁺), 206 (M⁺−42), 151 (M⁺−97), 124 (M⁺−124), 94 (M⁺−154).

(4) 1S-2-Oxa-3-oxo-6R-(3-oxo-4,4-propanohept-trans-1-enyl)-7R-acetoxy-cis-bicyclo[3,3,0]octane Anhydrous pyridine (19.1 ml.) and chromium trioxide (11.6 g., 116 mmol) were added to methylene chloride (310 ml.) at 10°–20°C. and stirred for 15 minutes. The reaction mixture was treated with Celite 545 (22 g.) and cooled to 0°C.

1S-2-Oxa-3-oxo-6R-hydroxymethyl-7R-acetoxy-cis-bicyclo[3,3,0]octane (4.7 g., 21.8 mmol) [prepared as described in J. Amer. Chem. Soc. 92, 397 (1970)] in methylene chloride (20 ml.) was oxidized using the chromium trioxide solution prepared as described above with stirring for 15 minutes at 0°C. After addition of sodium bisulphate monohydrate (85.5 g.), the mixture was stirred for an additional 10 minutes and then filtered through a pad of magnesium sulphate at 0°C. After washing the solids with cold methylene chloride, the solution was concentrated using a rotary evaporator (0°C.) to afford the crude aldehyde, which was used immediately in the next step.

To a suspension of sodium hydride (592 mg., 24.6 mmol) in 1,2-dimethoxyethane was added a soluton of dimethyl 2-oxo-3,3-propanohexylphosphonate (6.4 g., 24.4 mmol, prepared as described in (1) above) in 1,2-dimethoxyethane (117 ml.). The mixture was stirred at room temperature for 30 minutes, by which time no further hydrogen was evolved. To the reaction mixture was added the crude aldehyde (obtained as described above) in 1,2-dimethoxyethane (117 ml.) at 3°–5°C., and the mixture was stirred at room temperature for 40 minutes. After neutralizing excess base with glacial acetic acid, the solvent was removed under reduced pressure (<30°C.). The residue was dissolved in water and extracted with ethyl acetate. The organic layer was washed with water, dried over magnesium sulphate, and concentrated to give an oily product. The oily product was chromatographed on silica gel (100 g.) to yield 3.62 g. of the title compound (yield 29.4% based on 1S-2-oxa-3-oxo-6R-hydroxymethyl-7R-acetoxy-cis-bicyclo[3,3,0]octane by elution with benzene:ethyl acetate, 8:1) having the following physical characteristics:

NMR (CDCl₃ solution); δ: 6.71 (1H, double d, J=15.5 Hz, J=8.0 Hz), 6.31 (1H, d, J=15.5 Hz), 5.14–4.88 (2H, m), 2.04 (3H, s), 0.88 (3H, broad t); IR (CHCl₃); ν: 1775, 1740, 1690, 1630, 985 cm⁻¹; UV: $\lambda_{max}^{MeOH}$ = 227 mμ (ε 13,100); Mass spectrum: m/e = 275 (M⁺−59), 274 (M⁺−60); m.p. 71°–72°C.

(5) 1S-2-Oxa-3-oxo-6R-(3R (and 3S)-hydroxy-4,4,-propano-hept-trans-1-enyl)-7R-acetoxy-cis-bicyclo[3,3,0]octane To a solution of 1S-2-oxa-3-oxo-6R-(3-oxo-4,4-propanohept-trans-1-enyl)-7R-acetoxy-cis-bicyclo[3,3,0]octane (6.40 g., prepared as described in (4) above) in absolute methanol (57 ml.) and anhydrous tetrahydrofuran (29 ml.) was gradually added sodium borohydride (1.54 g., 40.6 mmol) at −30°C. After stirring for 15 minutes, the reaction mixture was quenched by addition of glacial acetic acid (5.1 ml.), and concentrated. The residue was dissolved in water and the solution extracted with chloroform. The extract was dried over sodium sulphate and concentrated to yield an oily product. After removal of excess acetic acid in vacuo, the crude residue was purified by column chromatography on silica gel (300 g.) using a mixture of diethyl ether and hexane (8:2) as eluent. The following fractions were collected.

3R-alcohol 2.59 g.
3R- and 3S-alcohols mixture 2.51 g.
3S-alcohol 2.48 g.

(i) 3R-alcohol has the following physical characteristics:

NMR (CDCl₃ solution); δ: 5.68–5.52 (2H, m), 5.09–4.85 (2H, m), 4.03 (1H, d, J=5.0 Hz), 2.03 (3H, s), 1.00–0.80 (3H, m); IR (CHCl₃); ν: 3500, 1770, 1740, 1240, 980 cm⁻¹;

Mass spectrum: m/e = 276 (M⁺−60); Optical rotation: [α]$_D^{22}$ = −14.8° (C = 0.91, CHCl₃).

(ii) 3S-alcohol has the following physical characteristics:

NMR (CDCl₃ solution); δ: 5.82–5.40 (2H, m), 5.09–4.87 (2H, m), 4.03 (1H, d, J=5.0 Hz), 2.04 (3H, s), 1.00–0.82 (3H, m); IR (CHCl₃); ν: 3500, 1770, 1735, 1240, 980 cm⁻¹; Mass spectrum: m/e = 337 (M⁺+1), 336 (M⁺), 276 (M⁺−60); Optical rotation: [α]$_D^{17}$ = −21.7° (C = 1.19, CHCl₃).

(6) 1S-2-Oxa-3-oxo-6R-(3R-hydroxy-4,4-propanohept-trans-1-enyl)-7R-hydroxy-cis-bicyclo[3,3,0]octane A heterogeneous mixture of 1S-2-oxa-3-oxo-6R-(3R-hydroxy-4,4-propanohept-trans-1enyl)-7R-acetoxy-cis-bicyclo[3,3,0]octane (5.0 g., prepared as described in (5) above), finely powdered anhydrous potassium carbonate (0.555 g., 4.02 mmol), and methanol (12 ml.) was vigorously stirred at room temperature for 15 minutes and then cooled in an ice bath. After addition of 1.0N hydrochloric acid (7.1 ml.), the reaction mixture was extracted with chloroform. The organic layer was washed with a saturated aqueous solution of sodium bicarbonate, dried over sodium sulphate, and concentrated by rotary evaporation to afford an oily product. The crude product was crystallized using diisopropyl ether to give 4.3 g. (yield 98%) of the title compound as a pale yellow oil having the following physical characteristics:

NMR (CDCl$_3$ solution); δ: 5.82–5.34 (2H, m), 5.02–4.80 (1H, m), 4.09–3.87 (2H, m), 1.02–0.80 (3H, m); IR (CHCl$_3$):ν: 3400, 1770, 1170, 1045, 980 cm$^{-1}$; Mass spectrum: m/e = 295 (M$^+$+1), 294 (M$^+$), 277 (M$^+$–17), 276 (M$^+$–18); Optical rotation: $[\alpha]_D^{17}$ = –7.90° (C = 1.03, CHCl$_3$).

(7) 1S-2-Oxa-3-oxo-6R-[3R-(2-tetrahydropyranyloxy)-4,4-propanohept-trans-1-enyl]-7R-(2-tetrahydropyranyloxy)-cis bicyclo[3,3,0]octane A solution of 1S-2-oxa-3-oxo-6R-(3R-hydroxy-4,4-propanohept-trans-1-enyl)-7R-hydroxy-cis-bicyclo[3,3,0]octane (3.70 g., prepared as described in (6) above), p-toluenesulphonic acid (10 mg.) and freshly distilled 2,3-dihydropyran (3.0 ml.) in methylene chloride (11.0 ml.) was stirred for 15 minutes at room temperature. The reaction was quenched by addition of 7 drops of pyridine and the mixture diluted with chloroform. After washing with a saturated aqueous solution of sodium chloride, the organic layer was dried over sodium sulphate and concentrated to yield a crude product which was partially purified by column chromatography on silica gel (110 g.), using a mixture of benzene and ethyl acetate (1:1) as eluent, to yield the title compound (6.26 g.) as a pale yellow oil (containing a small amount of dihydropyran polymers) having the following physical characteristics:

NMR (CDCl$_3$ solution); δ: 5.70–5.35 (2H, m), 5.10–4.80 (1H, m), 4.78–4.52 (2H, m), 4.25–3.26 (6H, m), 0.89 (3H, broad t); IR (CHCl$_3$); ν: 1770, 1140, 1080, 1030, 980 cm$^{-1}$;

Mass spectrum: m/e = 377 (M$^+$–85), 360 (M$^+$–102). Optical rotation: $[\alpha]_D^{18}$ = 46.2° (C = 1.57, CHCl$_3$).

(8) 1S-2-Oxa-3(ε)-hydroxy-6R-[3R-(2-tetrahydropyranyloxy)-4,4-propanohept-trans-1-enyl]-7R-(2-tetrahydropyranyloxy)-cis-bicyclo[3,3,0]octane To a stirred cold solution (–70°C.) of the crude 1S-2-oxa-3-oxo-6R-[3R-(2-tetrahydropyranyloxy)-4,4-propanohept-trans-1-enyl]-7R-(2-tetrahydropyranyloxy)-cis-bicyclo[3,3,0]octane (1.36 g.) (prepared as described in (7) above) in toluene (8.0 ml.) was added dropwise 2.0 ml. of a solution (25 g./100 ml.) in toluene of diisobutylaluminum hydride (0.500 g., 3.52 mmol). The homogenous solution was stirred for 20 minutes at –70°C., and then quenched by addition of methanol (5.0 ml.). After stirring for 15 minutes at room temperature, and then dilution with diethyl ether, the ethereal solution was washed with a saturaed aqueous solution of sodium chloride. After removal of gelled substances by suction filtration through Celite 545, the ethereal solution was dried over magnesium sulphate and concentrated to yield the title compound in almost quantitative yield as a pale yellow oil, which was used immediately without purification in (9) described hereinafter.

(9) 9α-Hydroxy-11α, 15R-bis-(2-tetrahydropyranyloxy)-16,16-propano-ω-norprosta-cis-5,trans-13-dienoic acid Sodiomethylsulphinylcarbanide was prepared as follows: A mixture of sodium hydride (242 mg.) and anhydrous dimethyl sulphoxide (5.0 ml.) was stirred at 60°C. until gas evolution ceased (ca. 2–3 hours). After cooling to room temperature, the solution was ready for use. The anhydrous dimethyl sulphoxide was prepared by drying and distilling over calcium hydride.

To a solution of 4-carboxy-n-butyltriphenyl-phosphonium bromide in anhydrous dimethyl sulphoxide (3.0 ml.) was added 3.66 ml. (7.38 mmol) of sodiomethylsulphinylcarbanide with stirring to give a red solution, to which, after a further 5 minutes stirring, a solution of 1.36 g. of 1S-2-oxa-3(ε)-hydroxy-6R-[3R-(2-tetrahydro-pyranyloxy)-4,4-propanohept-trans-1-enyl]-7R-(2-tetrahydro-pyranyloxy)-cis-bicyclo[3,3,0]octane (prepared as described in (8) above) in dimethyl sulphoxide (3.0 ml.) was added. The reaction mixture was stirred at 25°C. ± 1° for 2 hours, at 50°C. for an additional 30 minutes, and then quenched with ice-water. The reaction mixture was diluted with a mixture of ethyl acetate and diethyl ether (1:1), and then shaken with an aqueous solution of potassium carbonate, after which the pH of the solution was about 10. After confirming by TLC that no product was present in the organic layer, the aqueous layer was acidified to pH 2–3 with 1.0N hydrochloric acid and extracted with a mixture of pentane and diethyl ether (1:1). The acidic extracts were dried over magnesium sulphate and concentrated to yield an oily product. The oily product was purified by preparative TLC [using as developing solvent a mixture of chloroform and methanol (20:2) and as eluent a mixture of chloroform and methanol (4:1)] to give 770 mg. [yield 46.8% based on 1S-2-oxa-3-oxo-6R-[3R-(2-tetrahydropyranyloxy)-4,4-propanohept-trans-1-enyl]-7R-(2-tetrahydropranyloxy)-cis-bicyclo[3,3,0]octane] of the title compound having the following physical characteristics:

NMR (CDCl$_3$ solution); δ: 5.65–5.26 (4H, m), 4.76–4.45 (2H, m), 4.20–3.66 (4H, m), 3.60–3.43 (2H, m), 0.98–0.76 (3H, m); IR (CHCl$_3$); ν: 3600–2400, 1715, 1140, 1120, 1080, 1030, 980 cm$^{-1}$; Mass spectrum: m/e = 446 (M$^+$–102), 344 (M$^+$–204).

(10) 9-Oxo-11α,15R-bis-(2-tetrahydropropyanyloxy)-16,16-propano-ω-norprosta-cis-5,trans-13-dienoic acid A solution of manganese sulphate (5.7 g.) in water (28 ml.) was trapped with 1.36 ml. of concentrated sulphuric acid followed by chromium trioxide (1.24 g.) at 0°C. After stirring for 5 minutes at 0°C., the solution of oxidizing agent was ready for use.

To a solution of 668 mg. of 9α-hydroxy-11α,15R-bis-(2-tetrahydropyranyloxy)-16,16-propano-ω-norprosta-cis-5,trans-13-dienoic acid (prepared as described in (9) above) in diethyl ether (2.0 ml.) was added the previously prepared oxidizing agent at 0°C. After stirring for 2.5 hours at 0°C. the two phase reaction mixture was diluted with ethyl acetate. The organic layer was washed with a saturated aqueous solution of sodium chloride, dried over magnesium sulphate and concentrated to yield an oil product. The product was purified by column chromatography on silica gel (23 g.) using a mixture of methylene chloride and methanol (20:1) as eluent to give 650 mg. (yield 98%) of the title compound having the following physical characteristics:

NMR (CDCl₃ solution); δ; 9.50–8.50 (1H, D₂O exchanged), 5.75–5.25 (4H, m), 4.83–4.55 (2H, m), 4.30–3.65 (4H, m), 3.60–3.30 (2H, m), 0.95–0.75 (3H, m); IR (CHCl₃); ν: 3600–2300, 1740, 1710, 1140, 1080, 1040, 1030, 980 cm⁻¹; Mass spectrum: m/e = 362, 361, 344 (M⁺−202), 264, 263, 85; Optical rotation: [α]$_D^{23}$ = +94.6° (C = 1.44, CHCl₃).

(11) 16,16-Propano-ω-nor-PGE₂

A mixture of 631 mg. of 9-oxo-11α,15R-bis-(2-tetrahydropyranyloxy)-16,16-propano-ω-norprosta-cis-5,trans-13-dienoic acid (210 mg.) (prepared as described in (10) above), 7.5 ml. of aqueous acetic acid (65% v/v) and tetrahydrofuran (0.7 ml.) was stirred at 37°C. for 2.5 hours. The mixture was concentrated using a rotary evaporator to give an oil containing acetic acid which was removed azeotropically with toluene under reduced pressure. The residue was purified by preparative TLC [using as developing solvent a mixture of chloroform and ethanol (20:3) and as eluent a mixture of chloroform and methanol (4:1)] to give 291 mg. (yield 66%) of the title compound having the following physical characteristics:

TLC (developing solvent chloroform - methanol = 20:2); Rf = 0.30; NMR (CDCl₃ solution); δ: 6.40–5.75 (3H, D₂O exchanged), 5.73–5.50 (2H, m), 5.45–5.25 (2H, m), 4.20–3.35 (2H, m), 1.00–0.80 (3H, m); IR (CHCl₃); ν: 3700–2300, 3400, 1740, 1710, 980 cm⁻¹; Mass spectrum: m/e = 360 (M⁺−18), 342 (M⁺−36), 264, 263 (M⁺−115), 246; Optical rotation: [α]$_D^{28}$ = −56.0° (C = 1.72, CHCl₃).

PROCEDURE Z

Synthesis of 16,16-propano-ω-nor-PGE₂ methyl ester

A solution of 16,16-propano-ω-nor-PGE₂ (120 mg.) (prepared as described in Procedure Y) in methanol (5.0 ml.) was treated with excess diazomethane in diethyl ether. After stirring for a few minutes, the reaction mixture was concentrated. The residue was purified by preparative TLC [three developments using as developing solvent a mixture of chloroform and methanol (20:1) and as eluent a mixture of chloroform and methanol (4:1)] to give 110 mg. (yield 88%) of the title compound having the following physical characteristics:

TLC (developing solvent chloroform - methanol = 20:1); Rf = 0.37; IR (CHCl₃); ν: 3400, 1740, 1300–1200, 1160, 1080, 980 cm⁻¹.

PROCEDURE AA

Synthesis of 16,16-propano-ω-dihomo-PGE₂

(1) 2,2-Propanooctanoic acid

Proceeding as described in Procedure Y(1) using 9.00 g. of cyclobutane carboxylic acid and 16.0 g. of n-hexyl bromide, there were obtained 22.0 g. of crude product which was purified by column chromatography on silica gel using benzene as eluent to obtain the title compound (15.6 g.; quantitative yield) as a yellow liquid having the following physical characteristics:

NMR (CDCl₃ solution); δ: 9.47 (1H, broad s, D₂O exchanged), 2.60–2.25 (2H, m), 2.10–1.60 (6H, m), 1.47–1.10 (8H, m), 0.89 (3H, broad t); IR (liquid film); ν: 3400–2300, 1700 cm⁻¹; Mass spectrum: m/e = 184 (M⁺), 155, 141, 113, 100, 87, 70, 55, 41.

(2) 2,2-Propanooctanoyl chloride

Proceeding as described in Procedure Y(2) using 16.1 g. of 2,2-proanooctanoic acid (prepared as described in (1) above), there were obtained 15.7 g. (yield 95%) of the title compound having the following physical characteristics:

b.p. 100°–101°C./2 mm.Hg; IR (liquid film); ν: 1800 cm⁻¹.

(3) Dimethyl 2-oxo-3,3-propanononylphosphonate

Proceeding as described in Procedure Y(3) using 15.7 g. of 2,2-propanooctanoyl chloride (prepared as described in (2) above) and purifying the crude product by column chromatography on silica gel (200 g.) using a mixture of ethyl acetate and benzene (1:2) as eluent, there were obtained 21.7 g. (yield 90%) of the title compound (a yellow liquid) having the following physical characteristics:

NMR (CCl₄ solution); δ: 3.74 (6H, d, J=11.0 Hz), 2.92 (2H, d, J=22.0 Hz), 2.54–2.23 (2H, m), 2.00–1.55 (6H, m), 1.37–1.10 (8H, m), 0.88 (3H, broad t); IR (liquid film); ν: 1705, 1260, 1040 cm⁻¹; Mass spectrum: m/e = 291 (M⁺+1), 290 (M⁺), 127, 126, 125, 124, 110, 109.

(4) 1S-2-Oxa-3-oxo-6R-(3-oxo-4,4-propanodec-trans-1-enyl)-7R-acetoxy-cis-bicyclo[3,3,0]octane Proceeding as described in Procedure Y(4) using 12.1 g. of dimethyl 2-oxo-3,3-propanononylphosphonate (prepared as described in (3) above), there were obtained 5.0 g. (yield 35% based on 1S-2-oxa-3-oxo-6R-hydroxy-methyl-7R-acetoxy-cis-bicyclo[3,3,0]octane) of the title compound as a yellow oil, which was purified by recrystallization from diisopropyl ether to yield 3.4 g. of white crystals having the following physical characteristics:

NMR (CDCl₃ solution); δ: 6.72 (1H, double d, J=15.0 Hz, J=7.5 Hz), 6.31 (1H, d, J=15.0 Hz), 5.14–4.90 (2H, m), 2.63–2.15 (6H, m), 2.03 (3H, s), 1.97–1.65 (6H, m), 1.35–1.10 (8H, m), 0.95–0.75 (3H, broad t); IR (CHCl₃); ν: 1780, 1745, 1690, 1630, 1240, 980 cm⁻¹; Mass spectrum: m/e = 376 (M⁺), 317, 316, 292, 288, 232; UV: λ$_{max}^{MeOH}$ = 229 mμ (ε 6320); Optical rotation: [α]$_D^{22}$ = −11.1° (C = 1.74, CHCl₃); m.p. 92°–93°C.

(5) 1S-2-Oxa-3-oxo-6R-(3R (and 3S)-hydroxy-4,4-propanodec-trans-1-enyl)-7R-acetoxy-cis-bicyclo[3,3,-0]octane Proceeding as described in Procedure Y(5) using 3.4 g. of 1S-2-oxa-3-oxo-6R-(3-oxo-4,4-propanodec-trans-1-enyl)-7R-acetoxy-cis-bicyclo[3,3,0]octane (prepared as described in (4) above), the title compounds were obtained in the following yields (1.60 g. of enone compound were recovered):

3R-alcohol 900 mg.
3R- and 3S-alcohols mixture 550 mg.
3S-alcohol 350 mg.

(i) 3R-alcohol has the following physical characteristics:

NMR (CDCl₃ solution); δ: 5.81–5.42 (2H, m), 4.59–4.35 (2H, m), 4.01 (1H, d, J=5.0 Hz), 2.92–2.32 (6H, m), 2.02 (3H, s), 2.08 (1H, broad s, D₂O exchanged), 2.20–1.58 (6H, m), 1.43–1.15 (10H, m), 0.89 (3H, broad t); IR (CHCl₃); ν: 3500, 1775, 1740, 1240, 980 cm⁻¹; Mass spectrum: m/e = 378 (M⁺), 360 (M⁺−18), 318 (M⁺−60), 301, 300 (M⁺−78), 180; Optical rotation: [α]$_D^{20}$ = −12.0° (C = 2.13, CHCl₃).

(ii) 3S-alcohol has the following physical characteristics:

NMR (CDCl₃ solution); δ: 5.67–5.55 (2H, m), 5.10–4.85 (2H, m), 4.01 (1H, d, J=5.0 Hz), 2.90–2.35

(6H, m), 2.03 (3H, s), 1.94 (1H, broad s, D₂O exchanged), 2.18–1.55 (6H, m), 1.45–1.15 (10H, m), 0.90 (3H, broad t); IR (CHCl₃); $\nu$: 3450, 1775, 1740, 1240, 980 cm⁻¹; Mass spectrum: m/e = 378 (M⁺), 360 (M⁺−18), 318 (M⁺−60), 301, 300 (M⁺−78), 180; Optical rotation: $[\alpha]_D^{20}$ = −25.8° (C = 1.40, CHCl₃).

(6) 1S-2-Oxa-3-oxo-6R-(3R-hydroxy-4,4-propanodec-trans-1-enyl)-7R-hydroxy-cis-bicyclo[3,3,0]octane Proceeding as described in Procedure Y(6) using 1.34 g. of 1S-2-oxa-3-oxo-6R-(3R-hydroxy-4,4-propanodec-trans-1-enyl)-7R-acetoxy-cis-bicyclo[3,3,-0]octane (prepared as described in (5) above), there were obtained 939 mg. (yield 78%) of the title compound as white crystals having the following physical characteristics:

m.p. 97°–98°C.; NMR (CDCl₃ solution); δ: 5.80–5.34 (2H, m), 5.00–4.80 (1H, m), 4.08–3.70 (1H, m), 3.95 (1H, d, J=7.0 Hz), 3.70–3.65 (1H, D₂O exchanged), 2.90–2.70 (1H, D₂O exchanged), 2.90–2.15 (6H, m), 2.08–1.55 (6H, m), 1.50–1.13 (10H, m), 0.89 (3H, broad t); IR (CHCl₃); $\nu$: 3400, 1770, 980 cm⁻¹; Mass spectrum: m/e = 319, 318 (M⁺−18), 206, 181, 151, 150; Optical rotation: $[\alpha]_D^{17}$ = −0.0329° (C = 2.46, CHCl₃)..

(7) 1S-2-Oxa-3-oxo-6R-[3R-(2-tetrahydropyranyloxy)-4,4,-propanodec-trans-1-enyl]-7R-(2-tetrahydropyranyloxy)-cis-bicyclo[3,3,0]octane Proceeding as described in Procedure Y(7) using 939 mg. of 1S-2-oxa-3-oxo-6R-(3R-hydroxy-4,4-propanodec-trans-1-enyl)-7R-hydroxy-cis-bicyclo[3.3.0]octane (prepared as described in (6) above), the title compound was obtained in quantitative yield. It has the following physical characteristics:

NMR (CDCl₃ solution); δ: 5.60–5.34 (2H, m), 5.10–4.80 (1H, m), 4.75–4.55 (2H, m), 4.20–3.70 (4H, m), 3.62–3.30 (2H, m), 1.40–1.10 (10H, m), 0.89 (3H, broad t); IR (CHCl₃); $\nu$: 1770, 1190, 1140, 1120, 1080, 1040, 1030, 980 cm⁻¹; Mass spectrum: m/e = 420 (M⁺−84), 403 (M⁺−101), 365 (M⁺−139), 319, 318 (M⁺−186), 282, 281 (M⁺−223), 85; Optical rotation: $[\alpha]_D^{22}$ = −19.8° (C = 0.550, CHCl₃).

(8) 1S-2-Oxa-3(ξ)-hydroxy-6R-[3R-(2-tetrahydropyranyloxy)-4,4-propanodec-trans-1-enyl]-7R-(2-tetrahydropyranyloxy)-cis-bicyclo[3,3,0]octane Proceeding as described in Procedure Y(8) using 1.30 g. of 1S-2-oxa-3-oxo-6R-[3R-(2-tetrahydropyranyloxy)-4,4-propanodec-trans-1-enyl]-7R-(2-tetrahydropyranyloxy)-cis-bicyclo[3,3,0]octane (prepared as described in (7) above), the title compound was obtained in almost quantitative yield.

(9) 9α-Hydroxy-11α,15R-bis-(2-tetrahydropyranyloxy)-16,16-propano-ω-dihomoprosta-cis-5,trans-13-dienoic acid Proceeding as described in Procedure Y(9) using 1.30 g. of 1S-2-oxa-3(ξ)-hydroxy-6R-[3R-(2-tetraydro-pyranyloxy)-4,4-propanodec-trans-1-enyl]-7R-(2-tetrahydro-pyranyloxy)-cis-bicyclo[3,3,0]octane (prepared as described in (8) above), there were obtained 511 mg. (yield 34% based on 1S-2-oxa-3-oxo-6R-[3R-(2-tetrahydro-pyranyloxy)-4,4-propanodec-trans-1-enyl]-7R-(2-tetrahydro-pyranyloxy)-cis-bicyclo[3,3,-0]octane) of the title compound (827 mg. of the starting material were recovered) having the following physical characteristics:

NMR (CDCl₃ solution); δ: 5.70–5.25 (2H, m), 4.80–4.60 (2H, m), 4.30–3.65 (4H, m), 4.50–4.20 (2H, D₂O exchanged), 3.60–3.30 (2H, m), 1.35–1.10 (10H, m), 0.88 (3H, broad t); IR (CHCl₃); $\nu$: 3600–2300, 3500, 1710, 1140, 1120, 1080, 1040, 1025, 980 cm⁻¹; Mass spectrum: m/e = 405 (M⁺−185), 388, 334, 304, 285, 250, 201, 85; Optical rotation: $[\alpha]_D^{18}$ = −11.8° (C = 2.47, CHCl₃).

(10) 9-Oxo-11α,15R-bis-(2-tetrahydropyranyloxy)-16,16-propano-ω-dihomoprosta-cis-5,trans-13-dienoic acid Proceeding as described in Procedure Y(10) using 511 mg. of 9α-hydroxy-11α,15R-bis-(2-tetrahydropyranyloxy)-16,16-propano- ω-dihomoprosta-cis-5,trans-13-dienoic acid (prepared as described in (9) above), 313 mg. (yield 61%) of the title compound were obtained having the following physical characteristics:

NMR (CDClsolution); δ: 9.00–8.00 (1H, D₂O exchanged), 5.75–5.25 (4H, m), 4.85–4.55 (2H, m), 4.05–3.70 (4H, m), 1.36–1.19 (10H, m), 0.89 (3H, broad t); IR (CHCl₃); $\nu$: 3600–2300, 1740, 1710, 1140, 1120, 1080, 1040, 1025, 980 cm⁻¹; Mass spectrum: m/e = 486, 485 (M⁺−103), 402 (M⁺−186), 385 (M⁺−203), 384, 318, 264, 263 (M⁺−325), 245, 85; Optical rotation: $[\alpha]_D^{20}$ = −65.5° (C = 1.04, CHCl₃).

(11) 16,16-Propano-ω-dihomo-PGE₂

Proceeding as described in Procedure Y(11) using 313 mg. of 9-oxo-11α,15R-bis-(2-tetrahydropyranyloxy)-16,16-propano-ω-dihomoprosta-cis-5,trans-13-dienoic acid (prepared as described in (10) above), 152 mg. (yield 68%) of the title compound were obtained having the following physical characteristics:

TLC (developed twice with solvent chloroform - methanol = 20:1); Rf = 0.20; NMR (CDCl₃ solution); δ: 5.75–5.58 (2H, m), 5.50–5.30 (2H, m), 5.55–5.00 (3H, D₂O exchanged), 4.20–3.90 (2H, m), 1.40–1.20 (10H, m), 0.89 (3H, broad t); IR (CHCl₃); $\nu$: 3600–2300, 3355, 1740, 1710, 980 cm⁻¹; Mass spectrum: m/e = 402 (M⁺−18), 384 (M⁺−36), 264, 263 (402−139), 246, 245 (384−139), 137, 83, 69, 55; Optical rotation: $[\alpha]_D^{19}$ = −54.1° (C = 3.28, CHCl₃).

PROCEDURE BB

Synthesis of
17-phenyl-ω-trinor-16,16,17,17-tetradehydro-PGE₂α methyl ester (1) Methyl 9α,11α-diacetoxy-15(ξ)-hydroxy-17-phenyl-ω-trinor-16,16,17,1717-tetradehydro-prosta-cis-5,trans-13-dienoate 2.5 ml. of a 1.2M solution of n-butyllithium in n-hexane were added dropwise to a solution of 0.33 ml. of phenylacetylene in 5 ml. of anhydrous tetrahydrofuran under an atmosphere of nitrogen with stirring at −20°C., and the reaction mixture was stirred at the same temperature for 40 minutes to give a lithio-phenylacetylene solution. The lithio-phenylacetylene solution thus obtained was added dropwise under an atmosphere of nitrogen with stirring at −78°C. to a solution of 1.05 g. of 1α,4α-diacetoxy-2α-(6-methoxycarbonylhex-cis-2-enyl)-3β-(6-methoxycarbonylhex-cis-2-enyl)-3β-(2-formyleth-trans-1-enyl)-cyclopentane (prepared as described in Procedure R) in 10 ml. of anhydrous tetrahydrofuran and the reaction mixture was stirred at the same temperature for 2 hours. A saturated aqueous ammonium chloride solution was added to the reaction mixture, which was extracted with ethyl acetate. The extracts were washed with an aqueous sodium chloride solution, dried over sodium sulphate and concentrated under reduced pressure.

The residue was purified by column chromatography on silica gel using a mixture of benzene and ethyl acetate (5:1) as eluent to give 1.097 g. of the title compound having the following physical characteristics:

TLC (developing solvent benzene - ethyl acetate = 2:1); Rf = 0.47 and 0.50; NMR (CDCl$_3$ solution); δ: 7.60–7.00 (5H, m), 5.91–5.60 (2H, m), 5.60–5.17 (2H, m), 5.17–4.55 (3H, m), 3.63 (3H, s), 2.05 (3H, s), 2.01 (3H, s); IR (liquid film); ν: 3440, 3000, 2950, 2860, 2225, 1740, 1605, 1490, 1440, 1380, 1250, 1030, 975, 920, 770, 700 cm$^{-1}$.

(2) 17-Phenyl-ω-trinor-16,16,17,17-tetradehydro-PGF$_{2α}$ methyl ester 1.09 g. of methyl 9α,11α-diacetoxy-15(ξ)-hydroxy-17-phenyl-ω-trinor-16,16,17,17-tetradehydro-prosta-cis-5,trans-13-dienoate (prepared as described in (1) above) were dissolved in 10 ml. of absolute methanol and stirred with 640 mg. of potassium carbonate at 40° to 45°C. for 1 hour. The reaction mixture was cooled, acidified with acetic acid and extracted with ethyl acetate. The extracts were washed with water, an aqueous sodium bicarbonate solution and an aqueous sodium chloride solution, dried over sodium sulphate and concentrated under reduced pressure. The residue was purified by column chromatography on silica gel using a mixture of benzene and ethyl acetate (3:1) as eluent to give 477 mg. of the title compound and 381 mg. of the 15β-hydroxy isomer. The title compound showed the following physical characteristics:

TLC (developing solvent ethyl acetate); Rf = 0.30 (The Rf value of the 15β-hydroxy isomer was 0.35); NMR (CDCl$_3$ solution); δ: 7.60–7.10 (5H, m), 5.99–5.63 (2H, m), 5.63–5.22 (2H, m), 5.22–4.93 (1H, m), 4.40–3.76 (2H, m), 3.64 (3H, s); IR (liquid film); ν: 3350, 3000, 2940, 2220, 1740, 1605, 1575, 1490, 1440, 1380, 1250, 1180, 1035, 1020, 1000, 975, 765, 700 cm$^{-1}$; Optical rotation: [α]$_D^{18}$ = +6.3° (C = 1.5, CHCl$_3$).

PROCEDURE CC

Synthesis of 16-(cyclohex-1-enylthio)-ω-tetranor-PGF$_{2α}$ methyl ester (1) Methyl 9α-acetoxy-11α-(2-tetrahydropyranyloxy)-15α-hydroxy-16-(cyclohex-1-enylthio)-ω-tetranor-prosta-cis-5,-trans-13-dienoate 0.924 ml. of 1.4M n-butyllithium solution in n-hexane was added dropwise to a solution of 141 mg. of 1-methylthiocyclohexene [prepared as described in J. Chem. Soc., 5953 (1965)] in 2 ml. of tetrahydrofuran under an atmosphere of nitrogen at −64°C. The reaction mixture was stirred at −60°C. for 10 minutes, allowed to warm to 5°C. for 50 minutes, stirred at 5°C. for 3 hours and then warmed to 22°C. The reaction mixture thus obtained was added dropwise slowly over a period of 30 minutes to a solution of 422 mg. of 1α-acetoxy-2α-(6-methoxycarbonylhex-cis-2-enyl)-3β-(2-formyleth-trans-1-enyl)-4α-(2-tetrahydropyranyloxy)-cyclopentane (prepared as described in Procedure M) in 10 ml. of tetrahydrofuran at −66°C. and the reaction mixture was stirred at −66°C. for 1 hour, neutralized with 0.1 ml. of acetic acid, diluted with 0.5 ml. of water and concentrated slightly. The residue was diluted with 20 ml. of water and extracted with ethyl acetate. The extracts were washed with an aqueous sodium chloride solution, dried over magnesium sulphate and concentrated under reduced pressure. The residue was purified by column chromatography on silica gel using a mixture of ethyl acetate and benzene (1:3) as eluent to give 214 mg. of the title compound and 200 mg. of the 15β-hydroxy isomer. The title compound showed the following physical characteristics:

TLC (developing solvent ethyl acetate - benzene = 1:2); Rf = 0.50, (Rf of the 15β-hydroxy isomer = 0.55); IR (liquid film); ν: 3430, 2920, 1737, 1245, 1020, 970 cm$^{-1}$; NMR (CCl$_4$ solution); δ: 5.78–5.48 (3H, m), 5.45–5.15 (2H, m), 5.01 (1H, m), 4.67–4.47 (1H, m), 4.16–3.22 (4H, m), 3.62 (3H, s), 2.01 (3H, s).

(2) Methyl 9α-acetoxy-11α,15α-dihydroxy-16-(cyclohex-1-enylthio)-ω-tetranor-prosta-cis-5,trans-13-dienoate 550 mg. of methyl 9α-acetoxy-11α-(2-tetrahydropyranyloxy)-15α-hydroxy-16-(cyclohex-1-enylthio)-ω-tetranorprosta-cis-5,trans-13-dienoate (prepared as described in (1) above) were dissolved in a mixture of 6 ml. of acetic acid and 3.6 ml. of water and the reaction mixture was stirred at 40°C. for 50 minutes, neutralized with a solution of 10 g. of sodium bicarbonate in 15 ml. of water and extracted with ethyl acetate. The extracts were washed with an aqueous sodium chloride solution, dried over magnesium sulphate and concentrated under reduced pressure. The residue was purified by column chromatography on silica gel using a mixture of ethyl acetate and benzene (11:9) as eluent to give 326 mg. of the title compound having the following physical characteristics:

TLC (developing solvent ethyl acetate - benzene = 2:1); Rf = 0.28; IR (liquid film); ν: 3390, 2920, 1736, 1246 cm$^{-1}$; NMR (CCl$_4$ solution); δ: 5.82–5.17 (5H, m), 5.01 (1H, m), 4.35–3.40 (4H, m), 3.63 (3H, s).

(3) Methyl 9α,11α,15α-trihydroxy-16-(cyclohex-1-enylthio)-ω-tetranorprosta-cis-5,trans-13-dienoate [16-(Cyclohex-1-enylthio)-ω-tetranor-PGF$_{2α}$ -methyl ester]

500 mg. of potassium carbonate were added to a solution of 466 mg. of methyl 9α-acetoxy-11α,15α-dihydroxy-16-(cyclohex-1-enylthio)-ω-tetranorprosta-cis-5,trans-13-dienoate (prepared as described in (2) above) in 12 ml. of methanol. After stirring at 40°C. for 1 hour, the reaction mixture was acidified with 600 mg. of oxalic acid, diluted with 20 ml. of water and extracted with ethyl acetate. The extracts were washed with an aqueous sodium chloride solution, dried over magnesium sulphate and concentrated under reduced pressure. The residue was purified by column chromatography on silica gel using a mixture of ethyl acetate and benzene (4:3 and 3:2) as eluent to give 361 mg. of the title compound having the following physical characteristics:

TLC (developing solvent ethyl acetate); Rf = 0.42; IR (liquid film); ν: 3340, 2920, 1735, 1434, 1020, 970 cm$^{-1}$; NMR (CDCl$_3$ solution); δ: 5.79 (1H, m), 5.66–5.52 (2H, m), 5.52–5.20 (2H, m), 4.27–3.80 (3H, m), 3.68 (3H, s).

17(S)-Methyl-PGF$_{2α}$ , 17(R)-methyl-PGF$_{2α}$ , and 17(R)-methyl-PGE$_2$ may be prepared by the procedures described in our French Pat. Publication No. 2134673 (French Pat. Application No. 72.15314) utilizing as starting materials ethyl 3(S)-methyl-hexanoate and ethyl 3(R)-methylhexanoate. 15(S),16(R)-dimethyl-PGF$_{2α}$ may be prepared by the procedures described in our French Pat. Publication No. 2134673 (French Pat. Application No. 72.15314) utilising as starting material ethyl 2(R)-methylhexanoate and separating the 15(S)-compound from the 15(R)-compound by column chromatography of the final products.

The prostaglandin compounds 16(R)-methyl-PGF$_{2\alpha}$, 15,16-dimethyl-PGF$_{2\alpha}$, 16,16-dimethyl-PGF$_{2\alpha}$, 16(R)-methyl-PGE$_2$, 16,16-dimethyl-PGE$_2$ and 16-ethyl-PGE$_2$ may be prepared as described in our French Patent Publication No. 2134673 (French Pat. Application No. 72.15314). The prostaglandin compound 3,16(R)-dimethyl-PGE$_2$ may be prepared as described in our Belgian Pat. No. 804898. The prostaglandin compounds 13,14-dihydro-PGF$_{2\alpha}$, 15-methyl-13,14-dihydro-PGF$_{2\alpha}$, 13,14-dihydro-PGE$_2$, 15-methyl-13,14-dihydro-PGE$_2$, 16(R)-methyl-13,14-dihydro-PGE$_2$ and its methyl ester, 15,16(R)-dimethyl-13,14-dihydro-PGE$_2$ and 16-cyclohexyl-ω-trinor-13,14-dihydro-PGE$_2$ may be prepared as described in our Belgian Patent No. 805111. 15(S)-Methyl-PGF$_{2\alpha}$ may be prepared as described by G. L. Bundy, et al, Advances in the Biosciences, 9, 125 (1972).

The prostaglandin compounds 16-(3-trifluoromethylphenoxy)-ω-tetranor-PGF$_{2\alpha}$ and 16-phenoxy-ω-tetranor-PGF$_{2\alpha}$ may be prepared as described in Prostaglandins, 6, 87–90 (1974).

We claim:

1. A synergistic composition comprising as active ingredients a PGF$_{2\alpha}$ compound which is a member selected from the group consisting of PGF$_{2\alpha}$, ω-hexahomo-PGF$_{2\alpha}$, 15(S)-methyl-PGF$_{2\alpha}$, 16(R)-methyl-PGF$_{2\alpha}$, 17(S)-methyl-PGF$_{2\alpha}$, 17(R)-methyl-PGF$_{2\alpha}$, 18-methyl-PGF$_{2\alpha}$, 19-methyl-PGF$_{2\alpha}$, 15,16-dimethyl-PGF$_{2\alpha}$, 15(S),16(R)-dimethyl-PGF$_{2\alpha}$, 16,16-dimethyl-PGF$_{2\alpha}$, 17-ethyl-PGF$_{2\alpha}$, 16-cyclohexyl-ω-trinor-PGF$_{2\alpha}$, 13,14-dihydro-PGF$_{2\alpha}$, 15-methyl-13,14-dihydro-PGF$_{2\alpha}$, 16-methylene-PGF$_{2\alpha}$, 16-methylene-PGF$_{2\alpha}$ methyl ester, 16,16-ethano-PGF$_{2\alpha}$, trans-Δ$^{16}$-PGF$_{2\alpha}$ methyl ester, 16,17-methano-PGF$_{2\alpha}$, 15-methyl-16-phenylthio-ω-tetranor-PGF$_{2\alpha}$, 16-(3-trifluoromethylphenoxy)-9α,11α,15α-trihydroxy-ω-tetranorprosta-cis-5,trans-13-dienaldehyde, 9α,11α,15α-trihydroxy-16-phenylthio-ω-tetranorprosta-cis-5,trans-13-dienaldehyde, 9α,11α,15α-trihydroxy-16-phenoxy-ω-tetranorprosta-cis-5,trans-13-dienaldehyde, 9α,11α,15α-trihydroxy-16-(3-trifluoromethylphenoxy)-ω-tetranorprost-cis-5-enaldehyde, 15-(2-benzo[b]thienyl)-ω-pentanor-PGF$_{2\alpha}$ methyl ester, 15-(2-benzofuranyl)-ω-pentanor-PGF$_{2\alpha}$ methyl ester, 9α,11α,15α-trihydroxy-15-(2-benzofuranyl)-ω-pentanorprosta-cis-5,trans-13-dienaldehyde, 9α,11α,15α-trihydroxy-15-(2-benzo[b]-thienyl)-ω-pentanorprosta-cis-5,trans-13-dienaldehyde, 15-(2-benzofuranyl)-ω-pentanor-PGF$_{2\alpha}$ alcohol, 16-(cyclohex-1-enylthio)-ω-tetranor-PGF$_{2\alpha}$ methyl ester, 16-(3-trifluoromethylphenoxy)-ω-tetranor-PGF$_{2\alpha}$, 16-phenoxy-ω-tetranor-PGF$_{2\alpha}$ and 17-phenyl-ω-trinor-16,16,17,17-tetradehydro-PGF$_{2\alpha}$ -methyl ester, or its cyclodextrin clathrate thereof and a PGE$_2$ compound which is a member selected from the group consisting of PGE$_2$, ω-hexahomo-PGE$_2$, 16(R)-methyl-PGE$_2$, 17(R)-methyl-PGE$_2$, 18-methyl-PGE$_2$, 3,16(R)-dimethyl-PGE$_2$, 16,16-dimethyl-PGE$_2$, 16-ethyl-PGE$_2$, 17-ethyl-PGE$_2$, 13,14-dihydro-PGE$_2$, 15-methyl-13,14-dihydro-PGE$_2$, 16(R)-methyl-13,14-dihydro-PGE$_2$, 15,16(R)-dimethyl-13,14-dihydro-PGE$_2$, 16-cyclohexyl-ω-trinor-13,14-dihydro-PGE$_2$, 16-methylene-PGE$_2$ methyl ester, trans-Δ$^{16}$-PGE$_2$ methyl ester, 16(R)-methyl-13,14-dihydro-PGE$_2$ methyl ester, 16,16-ethano-PGE$_2$ methyl ester, 16(ξ)-methyl-20-hydroxy-PGE$_2$, 16,16-propano-ω-nor-PGE$_2$, 16,16-propano-ω-dihomo-PGE$_2$ and 16,16-propano-ω-nor-PGE$_2$ methyl ester, or its cyclodextrin clathrate thereof, at a weight ratio of from about 1:0.001 to about 1:2000.

2. A composition according to claim 1 wherein said PGE$_2$ compound is a member selected from the group consisting of PGE$_2$, ω-hexahomo-PGE$_2$, 16(R)-methyl-PGE$_2$, 17(R)-methyl-PGE$_2$, 18-methyl-PGE$_2$, 3,16(R)-dimethyl-PGE$_2$, 16,16-dimethyl-PGE$_2$, 16-ethyl-PGE$_2$, 17-ethyl-PGE$_2$, 13,14-dihydro-PGE$_2$, 15-methyl-13,14-dihydro-PGE$_2$, 16(R)-methyl-13,14-dihydro-PGE$_2$, 15,16(R)-dimethyl-13,14-dihydro-PGE$_2$, 16-cyclohexyl-ω-trinor-13,14-dihydro-PGE$_2$, 16-methylene-PGE$_2$ methyl ester, trans-Δ$^{16}$-PGE$_2$ methyl ester, 16(R)-methyl-13,14-dihydro-PGE$_2$ methyl ester, 16,16-ethano-PGE$_2$ methyl ester, 16(ξ)-methyl-20-hydroxy-PGE$_2$, 16,16-propano-ω-nor-PGE$_2$, 16,16-propano-ω-dihomo-PGE$_2$ and 16,16-propano-ω-nor-PGE$_2$ methyl ester.

3. A synergistic composition according to claim 1 in which said PGF$_{2\alpha}$ compound is PGF$_{2\alpha}$ and said PGE compound is PGE$_2$.

4. A synergistic composition according to claim 1 wherein said PGF compound is 15-methyl-13,14-dihydro-PGF$_{2\alpha}$ and said PGE compound is 16(R)-methyl-PGE$_2$.

5. A synergistic composition according to claim 1 wherein said PGF$_{2\alpha}$ compound is 16(R)-methyl-PGF$_{2\alpha}$ and said PGE compound is 16(R)-methyl-PGE$_2$.

6. A method for inducing an oxytocin effect in a female mammal which comprises administration of an effective amount of a composition according to claim 1.

7. A synergistic composition according to claim 1 wherein the weight ratio of said PGF$_{2\alpha}$ compound to said PGE$_2$ compound is from about 1:0.01 to about 1:1000.

8. A synergistic composition according to claim 1 wherein the weight ratio of said PGF$_{2\alpha}$ to PGE$_2$ compound is about 1:0.02 to about 1:500.

9. A method for producing a luteolytic effect in a female mammal which comprises the concomitant administration of about 1000 μg/kg of PGF$_{2\alpha}$ and 1000 μg/kg of PGE$_2$.

* * * * *